US012735456B2

(12) United States Patent
Wu et al.

(10) Patent No.: US 12,735,456 B2
(45) Date of Patent: Sep. 15, 2026

(54) CYCLIC PEPTIDE AND PREPARATION METHOD AND USE THEREOF

(71) Applicant: HANGZHOU HUIBO SCIENCE AND TECHNOLOGY CO., LTD, Hangzhou (CN)

(72) Inventors: Gang Wu, Hangzhou (CN); Yunyu Lu, Hangzhou (CN); Liyong Wu, Hangzhou (CN); Liuxingxing Cheng, Hangzhou (CN); Xiaoxuan Lei, Hangzhou (CN)

(73) Assignee: HANGZHOU HUIBO SCIENCE AND TECHNOLOGY CO., LTD., Hangzhou (CN)

( * ) Notice: Subject to any disclaimer, the term of this patent is extended or adjusted under 35 U.S.C. 154(b) by 412 days.

(21) Appl. No.: 18/579,276

(22) PCT Filed: Jul. 27, 2022

(86) PCT No.: PCT/CN2022/108058

§ 371 (c)(1),
(2) Date: Jan. 12, 2024

(87) PCT Pub. No.: WO2023/005945

PCT Pub. Date: Feb. 2, 2023

(65) Prior Publication Data

US 2024/0336658 A1 Oct. 10, 2024

(30) Foreign Application Priority Data

Jul. 27, 2021 (CN) ......................... 202110851741.0
Jul. 19, 2022 (CN) ......................... 202210852891.8
Jul. 19, 2022 (CN) ......................... 202210856468.5

(51) Int. Cl.

| | |
|---|---|
| ***C07K 7/56*** | (2006.01) |
| ***C07K 1/06*** | (2006.01) |
| ***C07K 1/113*** | (2006.01) |
| ***C07K 14/435*** | (2006.01) |

(52) U.S. Cl.

CPC ................ *C07K 7/56* (2013.01); *C07K 1/061* (2013.01); *C07K 1/113* (2013.01); *C07K 14/435* (2013.01)

(58) Field of Classification Search

CPC ....................................................... C07K 7/56
See application file for complete search history.

(56) References Cited

FOREIGN PATENT DOCUMENTS

| | | | |
|---|---|---|---|
| CN | 101492494 | A | 7/2009 |
| CN | 103249426 | A | 8/2013 |
| CN | 114344449 | A | 4/2022 |
| CN | 114774357 | A | 7/2022 |
| WO | WO2021/090855 | A1 | 5/2021 |

OTHER PUBLICATIONS

Khurshid, Z. et al., "*Histatin Peptides: Pharmacological Functions and their Applications in Dentistry.*", Saudi Pharmaceutical Journal., vol. 25, May 4, 2016 (May 4, 2016).

*Primary Examiner* — Amber D Steele
(74) *Attorney, Agent, or Firm* — MUNCY, GEISSLER, OLDS & LOWE, P.C.

(57) ABSTRACT

A cyclic peptide, and a preparation method and use thereof. The cyclic peptide is a series of head-to-tail cyclic peptides or N-terminal and C-terminal cyclized peptides with triazole rings, which are prepared by an azido-alkyne cycloaddition reaction of the whole sequence of linear histamine or the truncated sequence of a linear Hst1 under specific conditions. The biological activity of the full-sequence head-to-tail cyclic peptide or N-terminal and C-terminal cyclized peptide is increased by more than 1,000 times compared with that of the linear histamine, can significantly improve a dose-effect ratio and clinical efficacy of the histamine over the existing histamine cyclic peptide.

24 Claims, 22 Drawing Sheets

Specification includes a Sequence Listing.

(1) (2)

(1)

(2)

SEQUENCE LISTING

```
Sequence total quantity: 13
SEQ ID NO: 1            moltype = AA  length = 115
FEATURE                 Location/Qualifiers
source                  1..115
                        mol_type = protein
                        organism = synthetic construct
SEQUENCE: 1
ASPPSERHIS GLULYSARGH ISHISGLYTY RARGARGLYS PHEHISGLUL YSHISHISSE  60
RHISARGGLU PHEPROPHET YRGLYASPTY RGLYSERASN TYRLEUTYRA SPASN       115

SEQ ID NO: 2            moltype = AA  length = 81
FEATURE                 Location/Qualifiers
source                  1..81
                        mol_type = protein
                        organism = synthetic construct
SEQUENCE: 2
```

-continued

```
ARGLYSPHEH ISGLULYSHI SHISSERHIS ARGGLUPHEP ROPHETYRGL YASPTYRGLY  60
SERASNTYRL EUTYRASPAS N                                            81

SEQ ID NO: 3           moltype = AA  length = 96
FEATURE                Location/Qualifiers
source                 1..96
                       mol_type = protein
                       organism = synthetic construct
SEQUENCE: 3
ASPSERHISA LALYSARGHI SHISGLYTYR LYSARGLYSP HEHISGLULY SHISHISSER  60
HISARGGLYT YRARGSERAS NTYRLEUTYR ASPASN                            96

SEQ ID NO: 4           moltype = AA  length = 63
FEATURE                Location/Qualifiers
source                 1..63
                       mol_type = protein
                       organism = synthetic construct
SEQUENCE: 4
ARGLYSPHEH ISGLULYSHI SHISSERHIS ARGGLYTYRA RGSERASNTY RLEUTYRASP  60
ASN                                                                63

SEQ ID NO: 5           moltype = AA  length = 72
FEATURE                Location/Qualifiers
source                 1..72
                       mol_type = protein
                       organism = synthetic construct
SEQUENCE: 5
ASPSERHISA LALYSARGHI SHISGLYTYR LYSARGLYSP HEHISGLULY SHISHISSER  60
HISARGGLYT YR                                                      72

SEQ ID NO: 6           moltype = AA  length = 75
FEATURE                Location/Qualifiers
source                 1..75
                       mol_type = protein
                       organism = synthetic construct
SEQUENCE: 6
ASPSERHISA LALYSARGHI SHISGLYTYR LYSARGLYSP HEHISGLULY SHISHISSER  60
HISARGGLYT YRARG                                                   75

SEQ ID NO: 7           moltype = AA  length = 39
FEATURE                Location/Qualifiers
source                 1..39
                       mol_type = protein
                       organism = synthetic construct
SEQUENCE: 7
ARGLYSPHEH ISGLULYSHI SHISSERHIS ARGGLYTYR                         39

SEQ ID NO: 8           moltype = AA  length = 36
FEATURE                Location/Qualifiers
source                 1..36
                       mol_type = protein
                       organism = synthetic construct
SEQUENCE: 8
LYSPHEHISG LULYSHISHI SSERHISARG GLYTYR                            36

SEQ ID NO: 9           moltype = AA  length = 42
FEATURE                Location/Qualifiers
source                 1..42
                       mol_type = protein
                       organism = synthetic construct
SEQUENCE: 9
ARGLYSPHEH ISGLULYSHI SHISSERHIS ARGGLYTYRA RG                     42

SEQ ID NO: 10          moltype = AA  length = 39
FEATURE                Location/Qualifiers
source                 1..39
                       mol_type = protein
                       organism = synthetic construct
SEQUENCE: 10
LYSPHEHISG LULYSHISHI SSERHISARG GLYTYRARG                         39

SEQ ID NO: 11          moltype = AA  length = 24
FEATURE                Location/Qualifiers
source                 1..24
                       mol_type = protein
                       organism = synthetic construct
SEQUENCE: 11
LYSARGHISH ISGLYTYRLY SARG                                         24
```

-continued

```
SEQ ID NO: 12           moltype = AA  length = 21
FEATURE                 Location/Qualifiers
source                  1..21
                        mol_type = protein
                        organism = synthetic construct
SEQUENCE: 12
LYSARGHISH ISGLYTYRLY S                                          21

SEQ ID NO: 13           moltype = AA  length = 13
FEATURE                 Location/Qualifiers
source                  1..13
                        mol_type = protein
                        organism = synthetic construct
SEQUENCE: 13
SHREFPFYGD YGS                                                   13
```

CYCLIC PEPTIDE AND PREPARATION METHOD AND USE THEREOF

CROSS-REFERENCE TO RELATED APPLICATIONS

The present application claims priority of a Chinese earlier application Ser. No. 202110851741.0 filed on Jul. 27, 2021; priority of a Chinese earlier application Ser. No. 202210852891.8 filed on Jul. 19, 2022; and priority of a Chinese earlier application Ser. No. 202210856468.5 filed on Jul. 19, 2022; the entire contents of which are hereby incorporated by reference.

INCORPORATION-BY-REFERENCE OF SEQUENCE LISTING

The content of the electronic sequence listing (sequence listing.xml; Size: 12,951 bytes; and Date of Creation: Jan. 12, 2024) is herein incorporated by reference in its entirety.

BACKGROUND OF THE INVENTION

Field of the Invention

The present invention relates to the fields of biomedical technology and personal care, and specifically to a cyclic peptide and use thereof.

Description of the Related Art

Many linear peptides having very good biological activities and stability in vitro lose their activities very quickly after entering the body. Since an in vivo environment is complex, there are a variety of enzymes. The linear peptides are easily degraded and metabolized under action of the enzymes and in turn lose their activities. In order to obtain polypeptides with good biological activities, long half-life, and higher receptor selectivity, many polypeptide modification methods have been reported in the literature, including engineering the linear peptides into cyclic peptides. Such a macrocyclic molecule has a well-defined fixed conformation, can better fit a receptor, and has significantly reduced sensitivity to aminopeptidases and carboxypeptidases. Therefore, the metabolic stability and bioavailability of the cyclic peptides are much higher than those of the linear peptides.

The cyclic peptides are divided into head-to-tail cyclic peptides or N-terminal and C-terminal cyclized peptides, sidechain-to-sidechain cyclic peptides, sidechain-to-end cyclic peptides, disulfide-bridge-containing cyclic peptides, stapled peptides, and cyclic peptides containing other bridged structures, according to a cyclization manner. In terms of synthetic methods, the synthesis difficulty of the head-to-tail cyclic peptides or N-terminal and C-terminal cyclized peptides is the maximum. Because a peptide bond of the linear peptide has very strong p-bond features, the molecule prefers to form a trans conformation and is in a stretched state, causing the carboxyl and amino groups of the terminal groups belonging to a reaction center to be far apart in space, which is not conducive to occurrence of an intramolecular condensation reaction, but facilitates intermolecular condensation.

The head-to-tail cyclic peptide or N-terminal and C-terminal cyclized peptide is usually synthesized by forming an amido linkage from a carboxyl group and an amino group of a linear peptide having a free N-terminal and a free C-terminal in a dilute solution ($10^{-3}$-$10^{-4}$ M). The types and number of amino acids in a linear precursor play a crucial role in the case of cyclization and the yield of the cyclic peptides.

Since the number and types of amino acids contained in the linear peptide, the precursor of the cyclic peptide, are very different, the synthesis methods of the cyclic peptide are diversified. Reagents and methods that show high efficiency and a rapid condensation effect on a certain linear peptide may become inefficient or ineffective on another peptide chain. Therefore, long-term careful exploration and arduous efforts are required to find a corresponding cyclic peptide synthesis method based on the sequence of a target cyclic peptide.

Head-to-tail cyclization is an important method to improve the stiffness and stability of a peptide structure. Because an exoprotease, such as an aminopeptidase or carboxypeptidase, can recognize the N-terminal or C-terminal group of a linear peptide and in turn hydrolyze the linear peptide. Therefore, compared with the linear peptide, the cyclic peptide is more resistant to enzymatic proteolysis. The cyclic structure pre-limits the conformation of the cyclic peptide and blocks the exposed amino and carboxyl groups at both terminals, making the enzymatic cleavage effect worse and thus reducing the entropy cost in a receptor binding process. This feature increases their binding affinity and specificity for receptors and protein targets. Therefore, they are suitable for probing and modulating protein-protein interactions. With appropriate design, the cyclic peptide can mimic protein secondary structures (e.g., an α-helix and a β-hairpin) that are key modules for receptor recognition. All these favorable pharmacological features make the cyclic peptide be a potential drug candidate.

The synthesis methods of peptide chains mainly include liquid phase synthesis and solid phase synthesis. The liquid-phase synthesis uses fully-protected linear precursors (except for two cyclized terminals) that are directly coupled in the presence of a coupling reagent. However, this strategy suffers from several drawbacks, resulting in low synthesis efficiency. Firstly, cyclization must be carried out in a highly diluted solution to prevent/reduce oligomerization caused by intermolecular reactions, because peptide cyclization is an entropy-reducing process, resulting in a large waste of solvents, as well as cumbersome operation and post-processing processes. Secondly, an activated C-terminal carboxylic acid is prone to epimerization to produce a pair of cyclic isomers in turn, and the epimers may also be produced by enolizing an activated C-terminal carboxylic acid through deprotonation of an a proton under alkaline conditions, so the liquid phase synthesis has very high requirements on the purification process, resulting in reduced synthesis yield. Finally, some fully protected linear peptide precursors have poor solubility in organic solvents, which prevents their cyclization reactions. Therefore, a solid-phase polypeptide synthesis (SPPS) method is more competitive.

Currently, the existing head-to-tail cyclization methods mainly include: on-resin cyclization, chemical ligation, azide-alkyne cycloaddition, ring-closing metathesis and electrostatically-controlled macro-cyclization, etc.

There have been reports on the preparation of a cyclized Hst1 by a transpeptidase Sortase A method (Sortase A as a tool for high-yield histatin cyclization, Jan G. M. Bolscher, The FASEB Journal. Research Communication), and a high-activity Hst1 cyclic peptide is synthesized, but the solubility of the prepared cyclic peptide is poor because of the complicated steps, low catalytic efficiency (0.1-1 molar equivalent) and long reaction time (greater than 20 hours) of the adopted Sortase A enzymatic method. Furthermore, this method requires a large recognition unit, introduces redundant amino acid sequences at both ends of the head and the tail, unnecessarily increases the length and sequence complexity of the original polypeptide, has poor atom economy, and has a risk of generating polymers. Moreover, the mechanism of its transpeptidase reaction is reversible, which has the risk of leading to the cleavage of the generated cyclic peptide, and is especially unsuitable for the cyclization of small molecule oligopeptides. Meanwhile, because the Sortase A enzyme is expensive and belongs to a bacterial enzyme, it is easy to contain bacterial product residues, thereby causing process safety issues such as immunogens and pathogenic microorganisms. To sum up, it is difficult to prepare a high-purity Hst1 cyclic peptide that can be industrially produced on a large scale using the Sortase A enzymatic method. Moreover, CN103249426A discloses a histone-rich cyclic analog prepared by a disulfide bond method, but the disulfide bond method usually prepares cyclic peptides connected to side chains, is difficult to prepare stable head-to-tail cyclic peptides or N-terminal and C-terminal cyclized peptides, and is not applicable to peptide sequences that do not contain cysteine residues.

Therefore, there is an urgent need for a method of preparing a polypeptide of head-to-tail cyclic peptides or N-terminal and C-terminal cyclized peptides that is simpler, more efficient, has fewer side reactions, has high solubility of cyclization products, is safe and sterile, and can be produced on a large scale, so as to produce histatin head-to-tail cyclic peptides or N-terminal and C-terminal cyclized peptides with higher activity and better stability.

Additionally, the complete sequence of a linear Hst1 has been truncated to obtain a shortest sequence Hst1-MAD that can maintain Hst1 activity (see details in Structure-activity analysis of histatin, a potent wound healing peptide from human saliva: cyclization of histatin potentiates molar activity 1000-fold. The FASEB Journal. Research Communication), since the molecular weight of the truncated sequence is significantly reduced, the cost required to achieve the same activity will also be significantly reduced. If the head-to-tail cyclic peptides or N-terminal and C-terminal cyclized peptides of Hst1-MAD can be further prepared to improve their activity and stability, the production cost of unit activity will be further reduced.

BRIEF SUMMARY OF THE INVENTION

In view of the problems existed in the prior art, the present invention provides a cyclic peptide, and a preparation method and use thereof. The cyclic peptide is a series of head-to-tail cyclic peptides or N-terminal and C-terminal cyclized peptides with triazole rings, which are prepared by an azido-alkyne cycloaddition reaction of the whole sequence of linear histamine or the truncated sequence of linear Hst1 under specific conditions; where the biological activity of the head-to-tail cyclic peptides or N-terminal and C-terminal cyclized peptides of the full sequence of histamine is increased by more than 1.000 times compared with that of the linear histamine, can achieve the same effect as the linear histamine with the dosage of one thousandth of the linear histamine, which is higher than that of the existing histamine cyclic peptide, has significantly improved stability and anti-bio-metabolic degradation compared with disulfide bond cyclized peptides, has obviously improved solubility compared with the cyclized peptides prepared by the Sortase A enzymatic method, and has unique conformation; the head-to-tail cyclic peptides or N-terminal and C-terminal cyclized peptides of the truncated sequence of Hst1 has a molecular weight which is only 1/3 of that of the linear Hst1, biological activity that is 15 times that of the linear Hst1, and the cost for achieving the same activity that is only 1/100 of that of the linear Hst1, improved yield compared with cyclic peptides directly cyclized with amide bonds, and has significantly improved stability and anti-bio-metabolic degradation. The entire cyclization process is gentle, simple, convenient and efficient, and can produce high-purity head-to-tail cyclic peptides or N-terminal and C-terminal cyclized peptides, which can significantly improve the biological activity and clinical efficacy of histamine, can be used for preparing anti-aging and repairing skin care products, health care products, or medicines, and has very good industrialization prospects.

In a first aspect, the present invention provides a cyclic peptide, the structural formula of which is shown in Formula 1 or Formula 2:

Formula 1

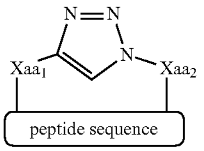

Formula 2

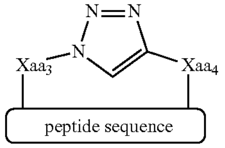

wherein, $Xaa_1$, $Xaa_2$, $Xaa_3$, and $Xaa_4$ are any amino acid, a peptide sequence is the sequence of any one of Hst1-Hst12 or Hst1-MAD, or a sequence and a fragment thereof having more than 80% homology with the sequence of any one of Hst1-Hst12 or Hst1-MAD, or a derivative modified peptide segment of any sequence of Hst1-Hst12 or Hst1-MAD and a fragment thereof; the Hst1-Hst12 respectively have amino acid sequences as shown in SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, SEQ ID NO.10, SEQ ID NO.11 and SEQ ID NO.12; and the Hst1-MAD has the amino acid sequence as shown in SEQ ID NO. 13 in the sequence listing.

In some embodiments, the $Xaa_1$, $Xaa_2$, $Xaa_3$ and $Xaa_4$ may be amino acids that are the same or different from each other.

The construction of a head-to-tail cyclic peptide or N-terminal and C-terminal cyclized peptide of histamine is very difficult, has high requirements on reaction conditions, and is prone to a side reaction phenomenon. The present invention creatively produces a series of histamine cyclic peptides containing triazole rings through an azide-alkynyl cycloaddition reaction and through the screening of a large number of reaction reagents and the exploration of process conditions, the activity of which is more than 1,000 times that of linear histamine.

The Hst1-MAD is obtained by truncating a complete Hst1 (histamine 1) sequence. The shortest sequence that can maintain the activity of the Hst1 is Hst1 (20-32), which is a sequence of the 20th to 32nd amino acids in the sequence of the histamine 1.

The construction of the head-to-tail cyclic peptide or N-terminal and C-terminal cyclized peptide of Hst1-MAD is also very difficult and prone to a side reaction phenomenon. In the present invention, through the azide-alkynyl cycloaddition reaction and through the screening of a large number of reaction reagents and the exploration of process conditions, a triazole ring-containing cyclic peptide of Hst1-MAD oligopeptides has also been successfully produced, the activity of which can reach about 15 times that of the linear Hst1 (histamine 1).

The triazole ring-containing cyclic peptide provided by the present invention can improve the biological activity and clinical efficacy of the histamine. The stability of histamine is improved through cyclization by locking the spatial conformation of polypeptide molecules, thereby improving the therapeutic effect and in vivo half-life. Various types of histamine cyclic peptides are prepared through the azide-alkyne cycloaddition reaction by introducing azide and alkyne groups into the head and the tail of the peptide chain and binding with resin at the same time.

The triazole ring-containing cyclic peptide of Hst1-MAD oligopeptides provided by the present invention can improve the biological activity and clinical efficacy of the Hst1, and can significantly reduce the cost. The molecular weight of the cyclic peptide of Hst1-MAD oligopeptides is only 1/3 of that of the linear histamine. When the concentration of it is only 1/10 of that of the linear Hst1, the biological activity of it is increased by 1.5 times compared with that of the linear Hst1. It can be seen that its activity can reach about 15 times that of the linear Hst1, but its mass concentration is reduced by 4/5. When it reaches the same activity, the cost of the head-to-tail cyclic peptide or N-terminal and C-terminal cyclized peptide of oligopeptides is only 1/100 of that of the linear Hst1.

Due to the construction of the triazole ring, the cyclic peptide provided by the present invention can resist the biological metabolic degradation, has excellent metabolic stability, can form hydrogen bond binding with biomolecule targets, can simulate a secondary structure such as a trans structure of peptide bonds of a natural polypeptide, improve solubility, can also resist the degradation of enzymes, and show excellent stability against hydrolysis and oxidation reactions.

Further, the derivatization modification includes one or more of alkylation, acylation, esterification, phosphorylation, sulfonation, glycosidation, PEGylation, biotinylation, fluorescent labeling, isotope labeling. D-type, a linking linker, carrier protein coupling or a special amino acid.

In some embodiments, the special amino acid includes derived amino acids of 20 basic amino acids that make up natural proteins, and special amino acids that make up certain special proteins, such as 4-hydroxyproline, 5-hydroxylysine, N-methyllysine, N-formylmethionine, γ-carboxyglutamic acid, selenocysteine, pyrrolysine, desmosine, isodesmosine, and β, γ, and δ-amino acids, etc.

In some embodiments, for the derivative modified peptide segment of any one of Hst1-Hst12 or Hst1-MAD, the derivatized modification includes but is not limited to methylation, alkylation, acylation, esterification, phosphorylation, sulfonation, glycosidation, PEGylation, biotinylation, fluorescent labeling or isotope labeling, D-type, linking various linkers, carrier protein coupling or a special amino acid, etc.

In some embodiments, the derivative modified peptide segment of any one of Hst1-Hst12 or Hst1-MAD includes peptide segments obtained by adding/deleting several amino acids from the head and the tail of the peptide segment of any one of Hst1-Hst12 or Hst1-MAD, modifying a L-type amino acid into a D-type amino acid, or derivative modification methods such as phosphorylation, acylation, glycosylation, methylation, hydroxylation, ubiquitination, lipidation, adding an aliphatic hydrocarbon group, an alicyclic hydrocarbon group, an aromatic hydrocarbon group, a heterocyclic group or halogenation and the like of amino acid groups.

In some embodiments, the derivative modified peptide fragment of any one of Hst1-Hst12 or Hst1-MAD includes N-terminal modification (e.g., Ac acetylation, etc.) of the peptide fragment of any one of the Hst1-Hst12 or the Hst1-MAD; N-terminal fatty acid modification (Myr myristic acid, Pal palmitic acid, Ste stearic acid, lauric acid, capric acid, caprylic acid modification, etc.); and C-terminal modification (—NH2 amidation, -PNA, -AMC, -OME, -OET, etc.).

In some embodiments, the derivative modified peptide fragment of any one of the Hst1-Hst12 or the Hst1-MAD includes fluorescent-labelling modification of the peptide fragment of any one of the Hst1-Hst12 or the Hst1-MAD, and the fluorescent label is for example Cy3, Cy5, Cy5.5, Cy7, FAM, FITC, Rhodamine B, TAMRA, etc.

In some embodiments, the derivative modified peptide fragment of any one of the Hst1-Hst12 or the Hst1-MAD includes biotinylation modification (e.g. BIOTIN, etc.), or PEGylation modification (the modification sites being at the N-terminal, C-terminal, Lys side chain and Cys thiol group, etc. of a polypeptide), or phosphorylation modification (e.g. p-Ser, p-Thr, p-Tyr, etc.), and methylation modification (e.g. Lys(Me), Arg(Me), etc.) of the peptide fragment of any one of the Hst1-Hst12 or the Hst1-MAD.

Further, the structural formula of the cyclic peptide is as shown in Formula 3 or Formula 4:

Formula 3

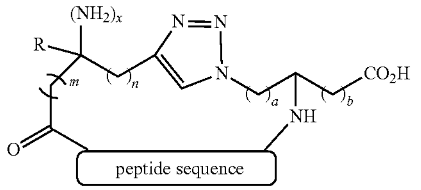

Formula 4

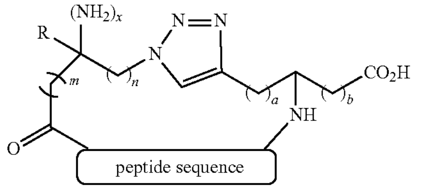

wherein, n=1-6, m=0-3, x=0 or 1, a=1-6, b=0-2, and the R group is the R group of any amino acid.

The R group is the R group of any amino acid, including natural amino acids and unnatural amino acids, essential amino acids and non-essential amino acids, L-type amino acids, special amino acids (D-type amino acids, beta amino acids, homo amino acids), and various other side chain-modified amino acids, etc.

In some embodiments, the R group includes but is not limited to H, an aliphatic hydrocarbon group, an alicyclic hydrocarbon group, an aromatic hydrocarbon group, a heterocyclic group, a halo group, etc.

In some embodiments, the R group is the fourth group of 20 natural amino acids connected to a C atom. Depending on the difference in the amino acid, the R group is also different, mainly including: —H, —$CH_3$, —$CH_2OH$, —$CH_2SH$, —$CH(OH)CH_3$, —$CH(CH_3)_2$, —$CH_2CH(CH_3)_2$, —$CH(CH_3)CH_2CH_3$, —$CH_2CH_2SCH_3$, —$C_7H_7$

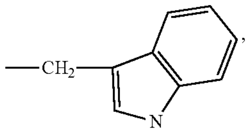

—$CH_2$-phenyl ring —OH, —$CH_2COOH$, —$CH_2CONH_2$, —$CH_2CH_2COOH$, —$CH_2CH_2CONH_2$, —CH—$CH_2CH_2CH_2NH_2$, —$CH_2CH_2NHCNH_2$,

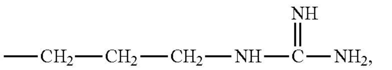

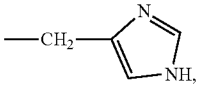
etc.

Further, the R group includes a (substituted) aliphatic hydrocarbon group, an alicyclic hydrocarbon group, an aromatic hydrocarbon group, a heterocyclic group or halogenation, etc.

Further, the R group includes —H or any one of methyl, ethyl and phenyl.

Further, the amino group and/or carboxyl group in Formula 3 or Formula 4 can be further derivatized, thereby obtaining a cyclic peptide in which —$NH_2$ and/or —COOH is derivatized.

Further, the derivatization of an amino group in the Formula 3 or Formula 4 includes any one or more of acylation, alkylation, PEGylation, biotinylation or fluorescent labeling of the amino group; and the derivatization of the carboxyl group in the Formula 3 or Formula 4 includes any one or more of amidation, esterification, glycosidation, PEGylation, etc. of the carboxyl group.

The derivative modification of the amino group includes but is not limited to acylation, alkylation, PEGylation, biotinylation, fluorescent labeling, etc.; and the carboxyl derivative modification includes but is not limited to amidation, esterification, glycosidation, PEGylation, etc.

Modified derivatives obtained by —$NH_2$ derivatization of the amino group, such as amidation, etc.; and modified derivatives obtained by —COOH derivatization of the carboxyl group, such as acylation, palmitoylation, myristoylation, acetylation, etc.

Further, the peptide sequence is the sequence of the Hst1, or a derivative modified peptide segment of the Hst1 sequence and a fragment thereof, or the amino acid sequence of the Hst1-MAD.

In some embodiments, a natural Hst1 amino acid sequence can be adopted as the Hst1 sequence.

In some embodiments, the amino acid sequence of the Hst1 in which the second AA is subjected to Ser phosphorylation can be adopted as the Hst1 sequence.

In some embodiments, the amino acid sequence of the Hst1 in which the second AA is not subjected to Ser phosphorylation can be adopted as the Hst1 sequence.

In some embodiments, a derivative modified peptide segment of the Hst1 or the Hst1-MAD, such as a sequence obtained after phosphorylation, acylation, glycosylation, methylation, hydroxylation, ubiquitination and lipidation of the amino acid sequence of the Hst1 or the Hst1-MAD, can be adopted as the sequence of the Hst1 or the Hst1-MAD.

In some embodiments, the N-terminal modified (e.g., Ac acetylation, etc.) amino acid sequence of the Hst1 or the Hst1-MAD, can be adopted as the sequence of the Hst1 or the Hst1-MAD.

In some embodiments, the amino acid sequence modified with a fatty acid (e.g. Myr myristic acid, Pal palmitic acid, Ste stearic acid, lauric acid, capric acid, caprylic acid modification, etc.) at the N-terminal of the Hst1 or the Hst1-MAD, can be adopted as the sequence of the Hst1 or the Hst1-MAD.

In some embodiments, the C-terminal modified (e.g. —NH2 amidation, -PNA, -AMC, -OME, -OET, etc.) amino acid sequence of the Hst1 or the Hst1-MAD, can be adopted as the sequence of the Hst1 or the Hst1-MAD.

In some embodiments, the amino acid sequence modified by a fluorescent label (Cy3, Cy5, Cy5.5, Cy7, FAM, FITC, Rhodamine B, TAMRA, etc.) of the Hst1 or the Hst1-MAD, can be adopted as the sequence of the Hst1 or the Hst1-MAD.

In some embodiments, the amino acid sequence modified by biotinylation (BIOTIN, etc.) of the Hst1 or the Hst1-MAD, can be adopted as the sequence of the Hst1 or the Hst1-MAD.

In some embodiments, the amino acid sequence modified by PEGylation of the Hst1 or the Hst1-MAD (the modification sites being at the N-terminal, C-terminal, Lys side chain and Cys thiol group of the polypeptide, etc.), can be adopted as the sequence of the Hst1 or the Hst1-MAD.

In some embodiments, the amino acid sequence modified by phosphorylation (e.g., p-Ser, p-Thr, p-Tyr, etc.) of the Hst1 or the Hst1-MAD, can be adopted as the sequence of the Hst1 or the Hst1-MAD.

In some embodiments, the amino acid sequence modified by methylation (e.g., Lys (Me), Arg (Me), etc.) of the Hst1 or the Hst1-MAD, can be adopted as the sequence of the Hst1 or the Hst1-MAD.

Further, the R group is —H. In this case, the structural formula of the cyclic peptide is as shown in Formula 5, Formula 6, Formula 25 or Formula 26:

Formula 5

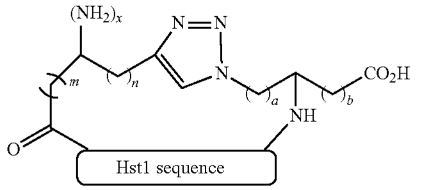

Formula 6

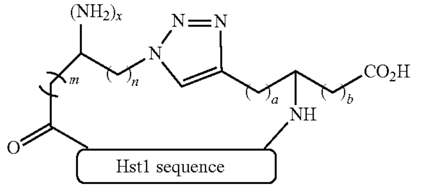

-continued

Formula 25

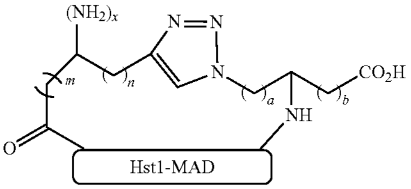

Formula 26

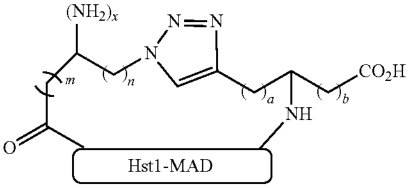

where, n=1-6, m=0-3, x=0 or 1, a=1-6, and b=0-3.

Further, the structural formula of the cyclic peptide is as shown in Formula 7, Formula 8, Formula 27 or Formula 28:

Formula 7

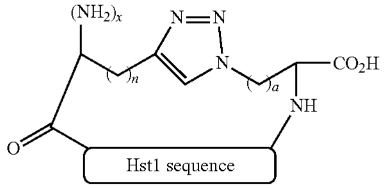

Formula 8

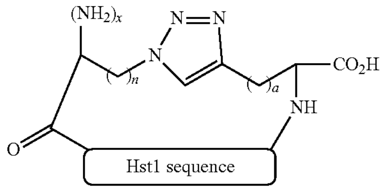

Formula 27

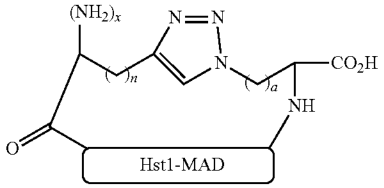

Formula 28

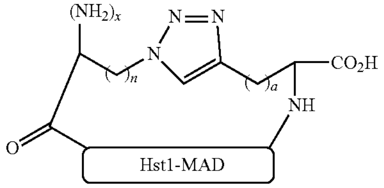

where, n=1-3, a=4, and x=0 or 1.

Further, a carbon chain in which the $Xaa_1$, $Xaa_2$, $Xaa_3$, and $Xaa_4$ are connected to the triazole ring may contain any one or more of a phenyl ring, an alicyclic ring, an aromatic ring, a heterocyclic ring or halogenation.

In another aspect, the present invention provides a method for preparing a cyclic peptide, which method mainly involves linking any amino acid containing an alkynyl group to one terminal of a peptide sequence, linking any amino acid containing an azide group to the other terminal, and binding with a resin at any of the terminals; where the alkynyl group and the azido group are subjected to cycloaddition, and the resin is removed to obtain a histamine cyclic peptide; the peptide sequence is the sequence of any one of Hst1-Hst12 or Hst1-MAD, or a sequence and a fragment thereof having more than 80% homology with the sequence of any one of Hst1-Hst12 or Hst1-MAD, or a derivative modified peptide segment of any sequence of Hst1-Hst12 or Hst1-MAD and a fragment thereof; the Hst1-Hst12 respectively have amino acid sequences as shown in SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, SEQ ID NO.10, SEQ ID NO.11 and SEQ ID NO.12; and the Hst1-MAD has the amino acid sequence as shown in SEQ ID NO. 13 in the sequence listing.

Further, the preparation method involves linking a $Xaa_1$ containing an alkynyl group at the C-terminal of the peptide sequence, and linking a $Xaa_2$ containing an azide group at the N-terminal, and binding with a resin on the $Xaa_2$, wherein the alkynyl group connected to the $Xaa_1$ and the azido group connected to the $Xaa_2$ undergo cycloaddition, and the resin is removed to obtain the cyclic peptide. The reaction formula of it is shown in Formula 9:

Formula 9

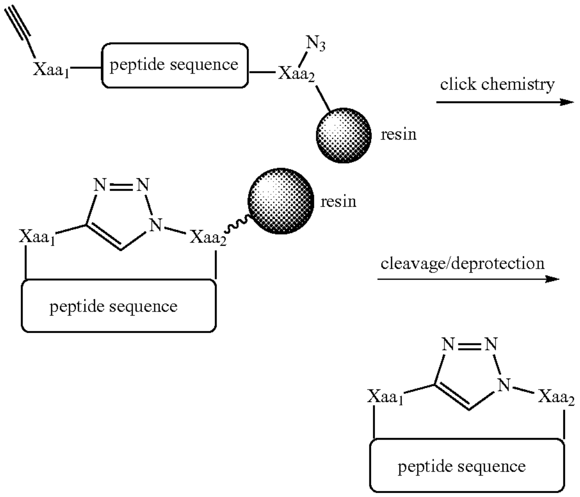

Alternatively, by linking a $Xaa_3$ containing an azide group at the C-terminal of the peptide sequence, linking a $Xaa_4$ containing an alkynyl group at the N-terminal, and binding with a resin on the $Xaa_4$, the azido group of the $Xaa_3$ and the alkynyl group of the $Xaa_4$ undergo cycloaddition, and the resin is removed to obtain the cyclic peptide. The reaction formula of it is as shown in Formula 10:

Formula 10

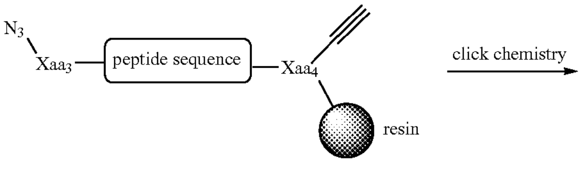

-continued

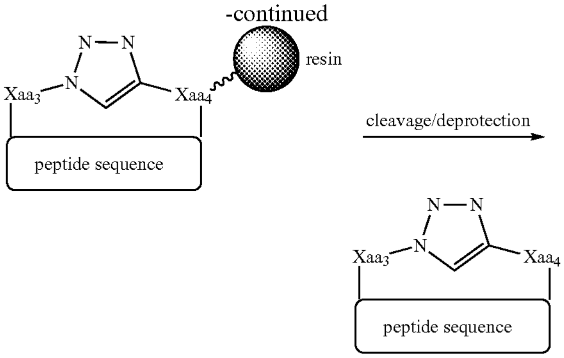

where, the $Xaa_1$, $Xaa_2$, $Xaa_3$, or $Xaa_4$ is any amino acid.

The derivatization modification includes but is not limited to alkylation, acylation, esterification, phosphorylation, glycosidation, PEGylation, biotinylation, fluorescent labeling, isotope labeling or special amino acids, etc.

Further, the structural formula of the $Xaa_1$ or $Xaa_4$ containing an alkynyl group is as shown in Formula 11, or the amino or carboxyl modified derivative as shown in Formula 11:

Formula 11

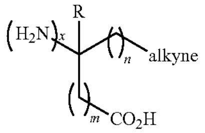

The structural formula of the $Xaa_2$ or $Xaa_3$ containing an azide group is as shown in Formula 12, or the amino or carboxyl modified derivative as shown in Formula 12:

Formula 12

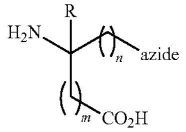

where, n=1-6, m=0-3, R group is the R group of any amino acid, and x=0 or 1.

In some embodiments, the R group includes but is not limited to H, an aliphatic hydrocarbon group, an alicyclic hydrocarbon group, an aromatic hydrocarbon group, a heterocyclic group, halogenation, etc.

Further, the amino —$NH_2$ and/or carboxyl group in Formula 11 or Formula 12 can be further derivatized, thereby obtaining a cyclic peptide after the —$NH_2$ and/or —COOH are derivated.

For the derivatization of the amino group and/or carboxyl group, the derivative modification of the amino group includes but is not limited to acylation, alkylation, PEGylation, biotinylation, fluorescent labeling, etc.; and the carboxyl derivative modification includes but is not limited to amidation, esterification, glycosidation, PEGylation, etc.

In some embodiments, modified derivatives obtained by —$NH_2$ derivatization of the amino group, such as amidation, etc.; and modified derivatives obtained by —COOH derivatization of the carboxyl group, such as acylation, palmitoylation, myristoylation, acetylation, etc.

Further, the peptide sequence is the sequence of the Hst1 or the Hst1-MAD.

Further, the R group is —H.

Further, it needs to connect a protecting group Fmoc on the —$NH_2$ of the $Xaa_1$, $Xaa_3$, $Xaa_3$ or $Xaa_4$ before the reaction. After the reaction is completed, the protecting group Fmoc is removed to obtain a naked —$NH_2$, or the naked —$NH_2$ is further derived.

In some embodiments, the derivatization includes, but is not limited to, acylation, alkylation, PEGylation, biotinylation, fluorescent labeling, etc.

Further, it needs to connect a protecting group Fmoc on the —$NH_2$ of the $Xaa_1$ or $Xaa_3$ before the reaction. After the reaction is completed, the protecting group Fmoc is removed to obtain a naked —$NH_2$, or the naked —$NH_2$ is further derived.

In some embodiments, the derivatization includes, but is not limited to, acylation, alkylation, PEGylation, biotinylation, fluorescent labeling, etc.

The amino —$NH_2$ is derivated, for example amidated, etc. to obtain a modified derivative.

Further, it needs to connect a protecting group Fmoc on the —$NH_2$ of the $Xaa_1$ or $Xaa_3$ before the reaction. After the reaction is completed, the protecting group Fmoc is removed to obtain a naked —$NH_2$, or the naked —$NH_2$ is further derived.

In some embodiments, the derivatization includes, but is not limited to, acylation, alkylation, PEGylation, biotinylation, fluorescent labeling, etc.

The amino —$NH_2$ is derivated, for example amidated, etc. to obtain a modified derivative.

Further, the structural formula of the $Xaa_1$ containing an alkynyl group is as shown in Formula 13:

Formula 13

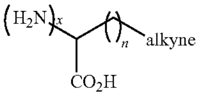

The structural formula of the $Xaa_2$ containing an azide group is as shown in Formula 14:

Formula 14

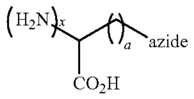

The structural formula of the $Xaa_3$ containing an azide group is as shown in Formula 15:

Formula 15

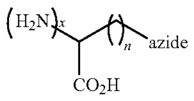

The structural formula of the $Xaa_4$ containing an alkynyl group is as shown in Formula 16:

Formula 16

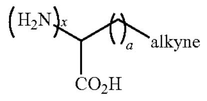

where, n=1-4, a=4, and x=0 or 1.

Further, the carbon chain of the $Xaa_1$ and/or $Xaa_4$ connected to the alkynyl group may contain any one or more of a phenyl ring, an alicyclic ring, an aromatic ring or a heterocyclic ring; the carbon chain of the $Xaa_2$ and/or $Xaa_3$ connected to the azide group may contain any one or more of a phenyl ring, an alicyclic ring, an aromatic ring, a heterocyclic ring or halogenation.

In some embodiments, the reaction formula of the preparation method is as shown in Formula 17.

Formula 17

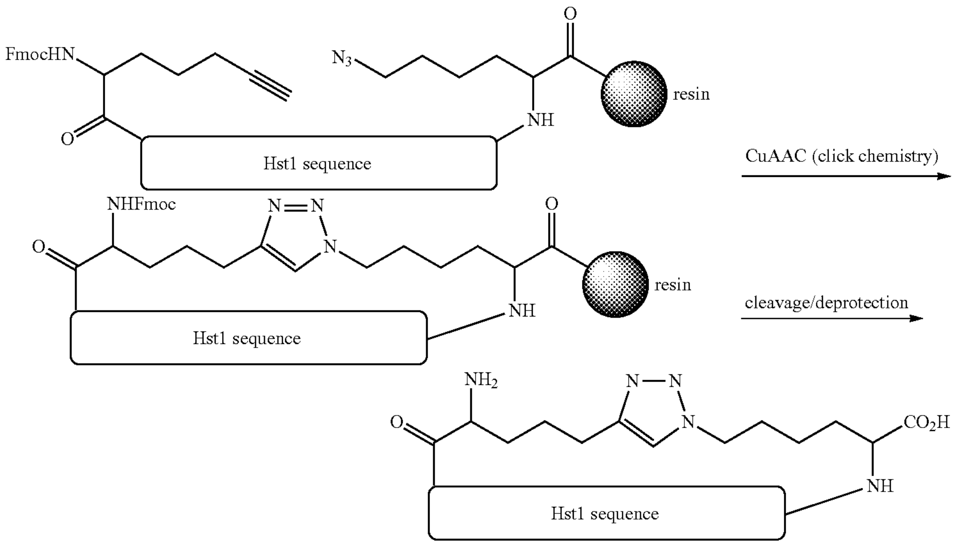

In some embodiments, the reaction formula of the preparation method is as shown in Formula 17-1.

Formula 17-1

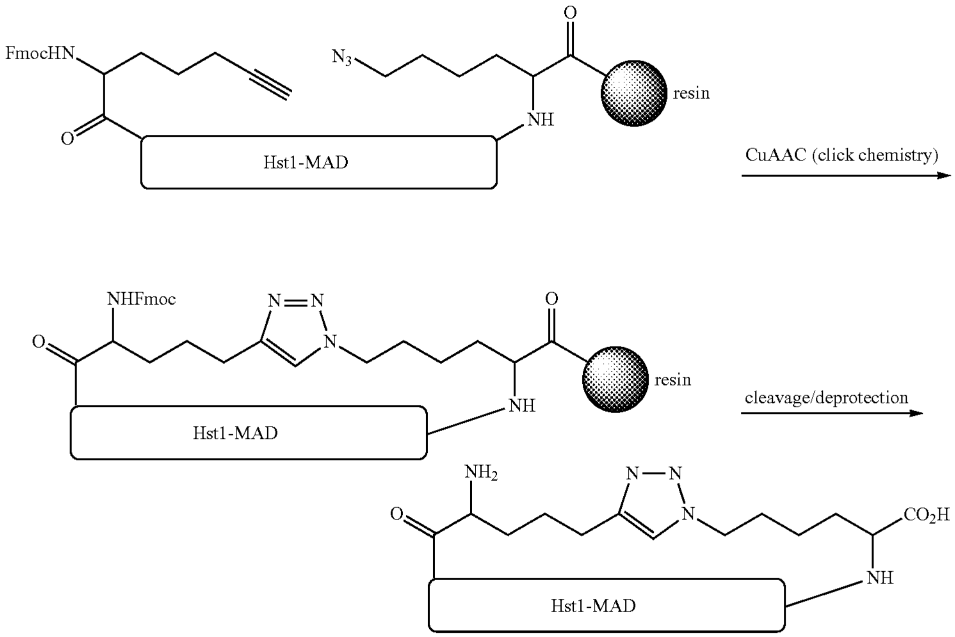

Further, the method for preparing the cyclic peptide includes the following steps:

1) placing a linear peptide prepared by a solid-phase polypeptide synthesis process into a container and adding a solvent; where the linear peptide is a linear histamine in which a $Xaa_1$ containing an alkynyl group is connected at the C-terminal, a $Xaa_2$ containing an azide group is connected at the N-terminal, and a resin is bound on the $Xaa_2$; or a linear histamine in which a $Xaa_3$ containing an azide group is connected at the C-terminal, a $Xaa_4$ containing an alkynyl group is connected at the N-terminal, and a resin is bound on the $Xaa_4$;
2) adding a catalyst;
3) adding a ligand;
4) blowing with nitrogen;
5) covering the container tightly and sealing the container, allowing the container to stand, and stirring;
6) washing with disodium ethylene diamine tetraacetate to remove a washing liquid;
7) washing with water, and washing with an organic solvent to remove a washing liquid;
8) subjecting to vacuum drying;
9) adding a mixed cleaving solution to cleave the polypeptide from the resin; and
10) purifying the polypeptide.

In some embodiments, the solvent can be a protic solvent for example selected from methanol, ethanol, tert-butanol, polyethylene glycol PEG, trifluoroethanol TFE, hexafluoroisopropanol HFIP, and water; a dipolar aprotic solvent, such as acetonitrile MeCN, dimethyl sulfoxide DMSO, acetone, N,N-dimethylformamide DMF, N,N-diisopropylethylamine DIPEA, N-methylpyrrolidone NMP, pyridine, piperidine; a non-polar solvent, such as dichloromethane DCM, trichloromethane, tetrahydrofuran THF, ethyl acetate, diethyl ether, benzene, toluene, carbon tetrachloride, dioxane, n-hexane, cyclohexane, etc.; can be a mixture of two or three of them according to a certain proportion, such as any one or more of tert-butanol/water, methanol/dichloromethane, dichloromethane/acetonitrile, dichloromethane/water, acetonitrile/dimethyl sulfoxide/water, acetone/dimethyl sulfoxide, ethanol/water, N-methylpyrrolidone/acetonitrile, N-methylpyrrolidone/dichloromethane/water, n-hexane/dioxane, N,N-dimethylformamide/trifluoroethanol, N,N-dimethylformamide/hexafluoroisopropanol, etc.

The steric hindrance, electrical properties, polarity, protonicity, hydrogen bonding ability and proportion of the solvent affect a reaction speed, generation ratios of side reaction by-products such as dimer and trimer polymers and decomposition products, etc.

Further, the solvent in the step 1) is a mixture of acetonitrile and dimethyl sulfoxide.

In some embodiments, the present invention adopts a formulated solution of acetonitrile and dimethyl sulfoxide (MeCN:DMSO) in a ratio of 4:1 as the solvent.

Studies have found that the concentration of the linear polypeptide in the solution will affect the reaction speed, leading to an increase in the proportion of side reaction by-products such as dimer and trimer polymers. However, in general, compared with the liquid phase synthesis method, the SPPS solid phase synthesis is more conducive to intramolecular cyclization rather than intermolecular cyclization and the like side reactions, which is one of the reasons for choosing SPPS in the present invention.

In some embodiments, in the present invention, preferably 500-750 mg of the linear polypeptide is adopted, and 20 ml of a solvent of acetonitrile and dimethyl sulfoxide (McCN:DMSO=4:1) is added.

Further, the resin of the present invention is selected from any one of Wang Resin, Rink Amide AM Resin, Rink Amide MBHA Resin, 2-Chlorotrityl Resin, PEGylated Rink-modified TentaGel (TGR) resin, Aminomethyl Resin, Sieber Amide Resin, PAM Resin, etc.

Different resins will affect the reaction speed and lead to an increase in side reaction by-products.

In some embodiments, Rink Amide MBHA Resin is adopted as the resin, which can accelerate the reaction speed and obviously reduce the occurrence of side reaction by-products.

Further, the catalyst of the present invention may be a copper or rhodium reagent.

In some embodiments, the catalyst of the present invention is a copper reagent that can be selected from a monovalent copper salt and a complex thereof, such as cuprous iodide CuI, cuprous chloride CuCl, cuprous iodide/triethyl phosphite $CuI·P(OEt)_3$, cuprous bromide, cuprous bromide dimethyl sulfide, tris(triphenylphosphine)cuprous bromide $[CuBr(PPh_3)_3]$, tris(triphenylphosphine)cuprous fluoride $[CuF(PPh_3)_3]$, tetrakis(acetonitrile)copper tetrafluoroborate $[Cu(MeCN)_4]BF_4$, tetrakis(acetonitrile)copper hexafluorophosphate $[Cu(MeCN)_4]PF_6$, tetrakis(acetonitrile)copper trifluoromethanesulfonate $[Cu(MeCN)_4]OTf$, various Cu (I)-carbene complexes; and it can also be selected from divalent copper salts and complexes thereof, such as copper sulfate $CuSO_4$, copper chloride $CuCl_2$, copper acetate $Cu(OAc)_2$, copper nitrate $Cu(NO_3)_2$, a composition of copper acetylacetonate $Cu(acac)_2$) and a reducing agent such as sodium ascorbate, or nano-copper and a composition thereof.

Moreover, the loading amount of the copper/rhodium reagent also affects the completion of the reaction to a certain extent, ranging from 0.05 eq to 4 eq. It can also be a non-copper/rhodium reagent such as HBTU/HOBt, but the effect difference is obvious.

Further, the catalyst in the step 2) is cuprous iodide.

Further, the added amount of cuprous iodide is 20 mM.

Further, the ligand of the present invention is generally a nitrogen-containing ligand, which can be selected from any one of 2,6-lutidine, diethylamine, tricthylamine, n-propylamine, diisopropylamine, tributylamine, diisopropylethylamine DIPEA, dimethylaminopyridine DMAP, 1,8-diazabicyclo[5.4.0] undec-7-ene DBU, pentamethyldiethylenetriamine PMDETA, hexamethyltriethylenetetramine HMTETA, tris(2-dimethylaminoethyl) amine Me6TREN, piperidine, pyridine, bipyridine, 2,2':6',2"-terpyridine tpy, tris(2-pyridylmethyl)amine TPMA, bipyridine, tert-butyl trichloroacetimidate TBTA, tris(3-hydroxypropyltriazolylmethyl)amine THPTA, TTTA, BTTAA, TABTA, BTTE, BTTP; it can also be a phosphorus-containing ligand, which can be selected from any one of triphenylphosphine, tricyclohexylphosphine PCy3, 1,1'-binaphthyl-2,2'-bisdiphenylphosphine BINAP, 1,2-bis(diphenylphosphine)ethane DPPE, 1,3-bis(diphenylphosphine) propane DPPP, 1,4-bis(diphenylphosphine)butane DPPB, and 1,5-bis(diphenylphosphine)pentane DPPPe; and it can also be a sulfur-containing ligand, which can be selected from any one of 4,4'-thiobis(6-tert-butyl-3-methylphenol BPS, BTTES, and BTTPS.

When the catalyst of the present invention is a copper reagent, the alkalinity, donor performance and steric hindrance of the ligand can stabilize a monovalent copper ion, prevent it from being oxidized or undergoing a disproportionation reaction, and meanwhile promote the formation of a cuprous acetylene complex and reduce the loading amount of the copper reagent, improve the efficiency of the cyclization reaction. The ratio of the ligand to copper varies from 0.5/1 to 4/1 and excess, depending on the relative activity, polarity and donor ability of the ligand, the copper reagent and the solvent.

Further, the ligand in the step 3) is 2,6-lutidine.

Further, the amount of 2,6-lutidine added in the present invention is 30 μL.

Further, the reaction conditions of the azide-alkynyl cycloaddition reaction of the present invention are also strictly limited.

Further, the step 4)-step 5) are the reaction process with a pH of 4-12, a reaction temperature of room temperature to 100° C., and a reaction time of 10 min to 100 h.

Further, the reaction process of the present invention must be deoxygenated;

oxygen will oxidize the copper reagent, causing the cyclization process to fail, so deoxygenation is important, while humidity can also affect reaction efficiency.

Further, the reaction process of the present invention requires blowing with nitrogen for 2 to 5 minutes. The blowing with nitrogen can be conducted for 2 to 5 minutes to ensure deoxygenation of the reaction process.

Further, it is also necessary to isolate from the air; the container is covered tightly and sealed to isolate from oxygen.

The reaction temperature of the present invention is room temperature to 100° C. The reaction temperature will affect the reaction speed and the relative proportions of products/by-products and decomposition products and their stability.

In some embodiments, the reaction of the present invention can also be carried out under microwave conditions (room temperature to 100° C.), which can accelerate the reaction, but our research has proven that the microwave conditions are prone to producing by-products and decomposition products.

Further, after the reaction is completed, it needs to shake and wash the container with a saturated disodium ethylene diamine tetraacetate solution. The chelating agent EDTA is used for removing copper ions.

Further, EDTA is adopted to shake and wash twice, for 10 minutes each time.

Further, it is also necessary to wash once with water, once with acetonitrile, once with dichloromethane, and once with diethyl ether to remove the washing liquid.

Further, it is necessary to conduct vacuum drying for 1 hour after the washing is completed.

Further, pyrolysis is performed after drying is completed: following a standard procedure: 20 ml of a mixed solution (95.5% of trifluoroacetic acid, 2% of a phenol aqueous solution, 2% of thioanisole, and 0.5% of triisopropylsilane) is shaken for 3 hours to cleave the polypeptide from the resin. The polypeptide is filtered with cold diethyl ether, washed for 3 times, and dried.

Further, it also needs to be further purified by high performance liquid chromatography (HPLC), using an acetonitrile aqueous solution containing 0.1% (v/v) of trifluoroacetic acid as a mobile phase for gradient elution and a detection wavelength of 210 nm.

Further, the preparation method includes the following steps:

1) placing 500-750 mg of a linear peptide prepared by a solid-phase peptide synthesis process in a container, and adding 20 ml of a mixed solution of acetonitrile and dimethyl sulfoxide formulated in a ratio of 1:1-10:1; wherein the linear peptide is a linear histamine in which a Xaa1 containing an alkynyl group is connected at the C-terminal, a Xaa2 containing an azide group is connected at the N-terminal, and a resin is bound on the Xaa2; or a linear histamine in which a Xaa3 containing an azide group is connected at the C-terminal, a Xaa4 containing an alkynyl group is connected at the N-terminal, and a resin is bound on the Xaa4;
2) adding 500-750 mg of a resin;
3) adding 20 mM of cuprous iodide;
4) adding 30 μL of 2,6-lutidine;
5) blowing with nitrogen for 2-5 minutes;
6) covering the container tightly and sealing the container;
7) reacting under stirring at room temperature for 40 minutes;
8) washing twice with a saturated disodium ethylene diamine tetraacetate solution under shaking, for 10 minutes each time, to remove the washing liquid;
9) washing once with water, once with acetonitrile, once with dichloromethane, and once with diethyl ether, to remove the washing liquid;
10) subjecting to vacuum drying for 1 hour;
11) cleaving: formulating a mixed cleaving solution including trifluoroacetic acid:phenol:thioanisole:triisopropylsilane=95.5:2:2:0.5, v/v), taking and adding 20 ml of the mixed cleaving solution into a sample obtained in the step 10), shaking for 3 hours to cleave a polypeptide from the resin, and filtering the polypeptide out with cold diethyl ether, washing for 3 times, and drying; and
12) purifying with high-performance liquid mass spectrometry.

Studies have proven that by adopting the cyclization method provided by the present invention, long peptide chains can be cyclized head-to-tail, and any histamine Hst1-Hst12 can be successfully cyclized, thereby producing a histamine cyclic peptide containing a triazole ring. The preparation process of the cyclic peptide is simple and convenient, high in purity, high in activity, and easy for large-scale industrial production.

In a further aspect, the present invention provides use of a cyclic peptide in promoting wound healing or skin care. The structural formula of the polypeptide cyclic peptide is as shown in Formula 7, Formula 8, Formula 27 or Formula 28:

Formula 7

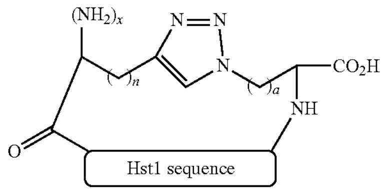

Formula 8

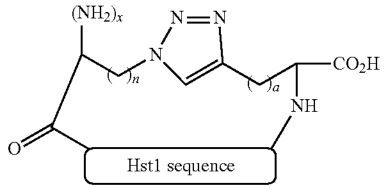

-continued

Formula 27

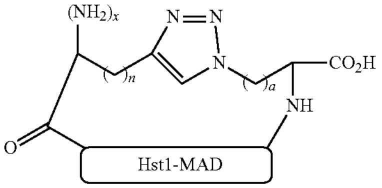

Formula 28

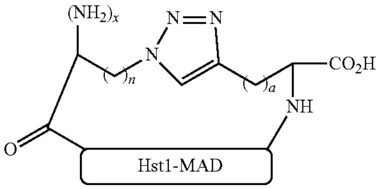

where, n=1-3, a=4, x=0 or 1, the Hst1 has an amino acid sequence as shown in SEQ ID NO.1 in the sequence listing, and the Hst1-MAD has the amino acid sequence as shown in SEQ ID NO.13 in the sequence listing.

In the present invention, a cyclic peptide containing a triazole ring is prepared by a copper-catalyzed azido-alkyne cycloaddition reaction, and only a 1,4-disubstituted [1,2,3] triazole product is generated by this reaction, which is similar to natural peptide bonds in many aspects, such as the ability to form hydrogen bonds, planarity, the distance between substituents at positions 1 and 4, and the conformation limitation of a peptide skeleton, etc. Therefore, replacing the peptide bond with a triazole in the modified peptide can exhibit a secondary structure similar to that of the natural polypeptide.

The beneficial effects of the present invention are as follows.

1. A series of histamine or Hst1-MAD head-to-tail cyclic peptides or N-terminal and C-terminal cyclized peptides with triazole rings are creatively prepared by the azido-alkyne cycloaddition reaction.
2. The activity of the prepared histamine head-to-tail cyclic peptide or N-terminal and C-terminal cyclized peptide is more than 1000 times higher than that of the linear histamine. It has excellent stability and resistance to biological metabolic degradation, and can improve solubility. It has a unique conformation and the biological activity and clinical efficacy of the histamine are significantly improved. The prepared Hst1-MAD head-to-tail cyclic peptide or N-terminal and C-terminal cyclized peptide has a molecular weight that is only ⅓ of that of the linear histamine and biological activity that is 15 times that of the linear histamine.
3. The prepared head-to-tail cyclic peptide or N-terminal and C-terminal cyclized peptide has excellent stability and resistance to biological metabolic degradation, can improve solubility, has a unique conformation, and significantly improves the biological activity and clinical efficacy of the histamine.
4. When the same activity is achieved, the cost of the Hst1-MAD head-to-tail cyclic peptide or N-terminal and C-terminal cyclized peptide is only 1/100 of that of the linear histamine.
5. The cyclization process adopted in the present invention is gentle, simple, convenient and efficient, and the prepared histamine or Hst1-MAD head-to-tail cyclic peptide or N-terminal and C-terminal cyclized peptide has higher purity, and has very good prospects for large-scale and industrial application.

DETAILED DESCRIPTION OF THE INVENTION

Figure 1:
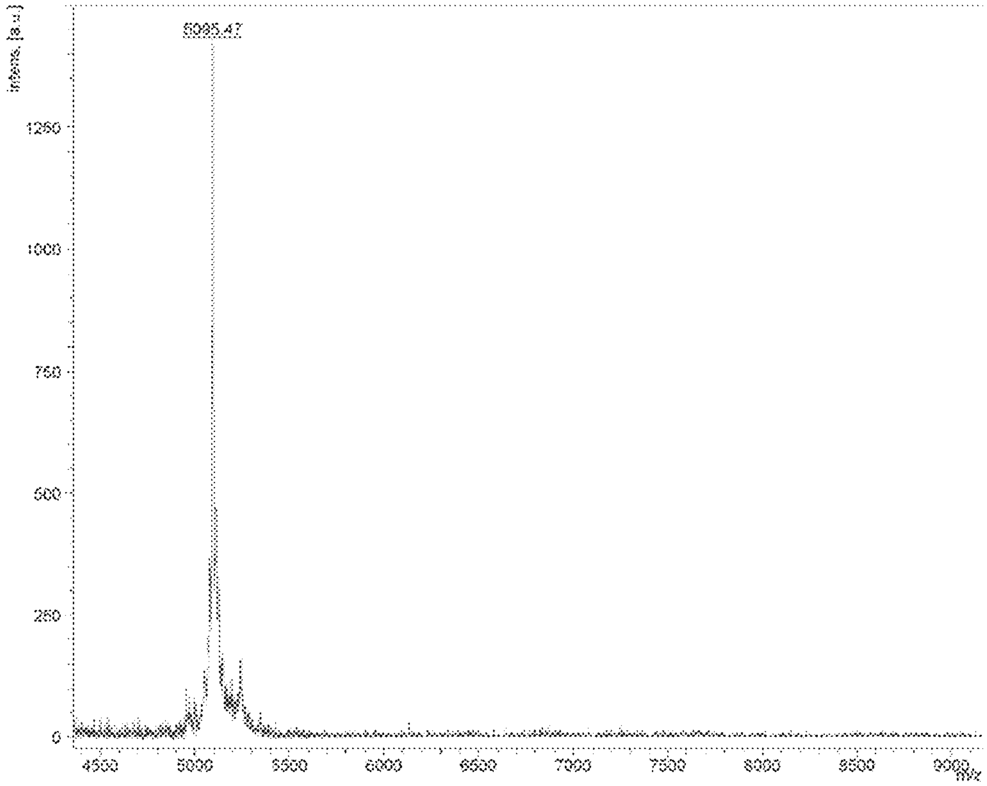
FIG. 1 is a mass spectrum MS detection pattern of a cyclization reaction product in Example 1.

The present invention will be further described in detail with reference to examples, and it should be pointed out that the following examples are intended to facilitate the understanding of the present invention, without any limitation to it. The reagents used in the present invention are all commercially available reagents.

Example 1 Preparation of Propargylglycine-Hst1 Cyclic Peptide

The preparation method of this example was:

1. an alkynyl group and a protective group Fmoc were introduced onto glycine, and an azide group and a protective group Fmoc were introduced onto lysine to obtain a Fmoc-propynylglycine (of Formula 18) for connecting at the C-terminal (in this example the Fmoc-propynylglycine purchased from Merck KGaA was directly used) and a Fmoc-azidolysine (of Formula 19) for connecting at the N-terminal (in this example the Fmoc-azidolysine purchased from Merck KGaA was directly used), and structural formulas of them were as shown below:

Formula 18

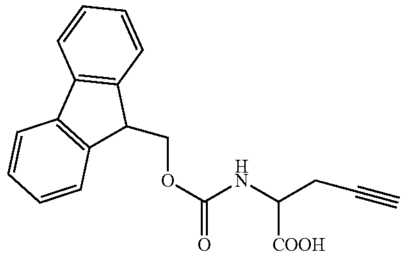

Formula 19

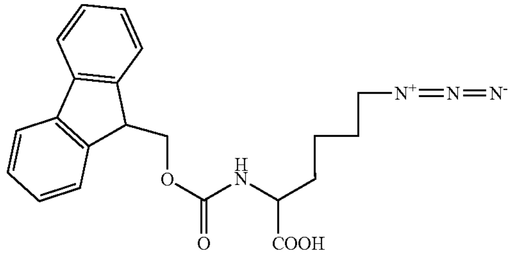

2. on the basis of the Fmoc-azidolysine, from right to left, the linear amino acids of Hst1 were synthesized step by step by adopting a solid-phase polypeptide synthesis (SPPS) method, and the Fmoc-propynylglycine was connected to the C-terminal of the Hst1; and
3. the Hst1 linear polypeptide prepared in the step 2 was utilized to prepare a Hst1 cyclic peptide through a copper-catalyzed azido-alkyne cycloaddition reaction, where the preparation method included the following steps:

1) 500 mg of the Hst1 linear polypeptide was placed in a container, added with 20 ml of a mixed solution of acetonitrile and dimethyl sulfoxide formulated in a ratio of 4:1;
2) the mixture was added with 500 mg of a resin Rink Amide MBHA Resin (purchased from Merck KGaA);
3) the mixture was added with 20 mM of cuprous iodide;
4) the mixture was added with 30 µl of 2,6-lutidine (dimethyl pyridine);
5) the mixture was blown with nitrogen for 5 minutes;
6) the container was covered tightly and sealed;
7) reaction was conducted under stirring at room temperature for 40 minutes;
8) it was washed twice with a saturated disodium ethylene diamine tetraacetate solution under shaking, for 10 minutes each time, to remove the washing liquid;
9) it was washed once with water, once with acetonitrile, once with dichloromethane, and once with diethyl ether, to remove the washing liquid;
10) it was subjected to vacuum drying for 1 hour;
11) cleaving: a mixed cleaving solution was formulated, including 95.5% of trifluoroacetic acid, 2% of a phenol aqueous solution, 2% of thioanisole, and 0.5% of triisopropylsilane, 20 ml of the mixed cleaving solution was taken and added into a sample obtained in the step 10), shaken for 3 hours to cleave a polypeptide from a template; and the polypeptide was filtered with cold diethyl ether, washed for 3 times, and dried; and
12) the polypeptide was purified by high performance liquid chromatography (HPLC), using an acetonitrile aqueous solution containing 0.1% (v/v) of trifluoroacetic acid as a mobile phase for gradient elution and a detection wavelength of 210 nm.

456 mg of a propargylglycine-Hst1 cyclic peptide was prepared.

The structural formula of the propynylglycine-Hst1 cyclic peptide was as shown in Formula 20:

Formula 20

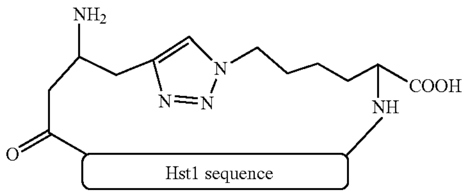

Figure 2:
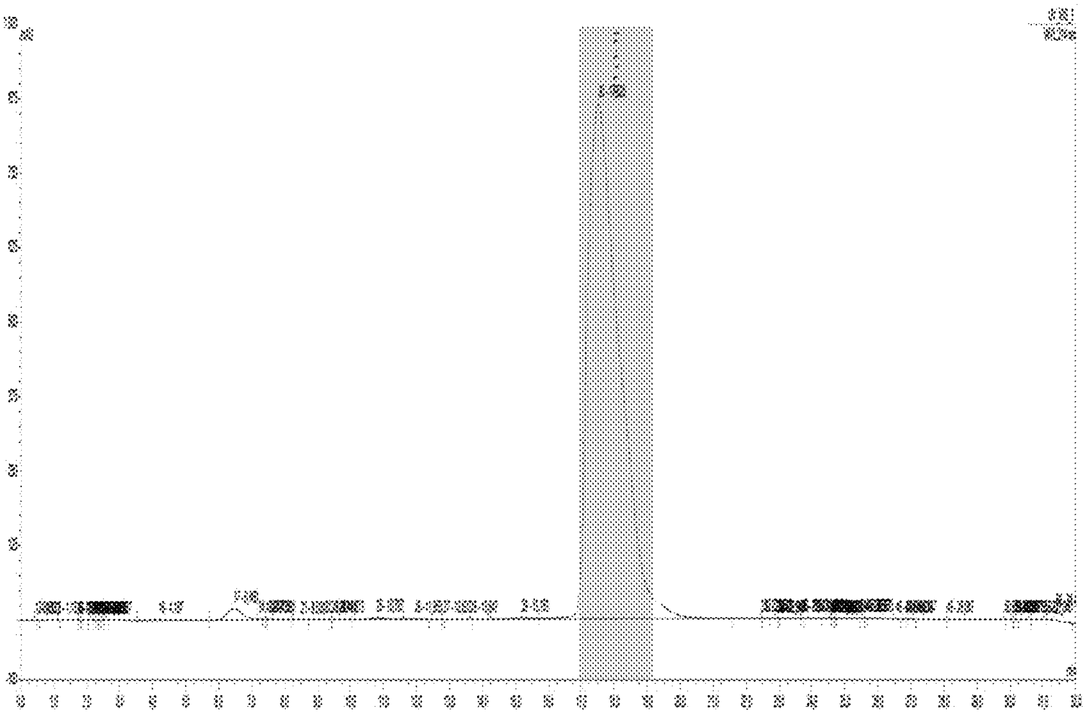
FIG. 2 is a high-performance liquid chromatography HPLC detection pattern of the cyclization reaction product in Example 1.
Figure 3:
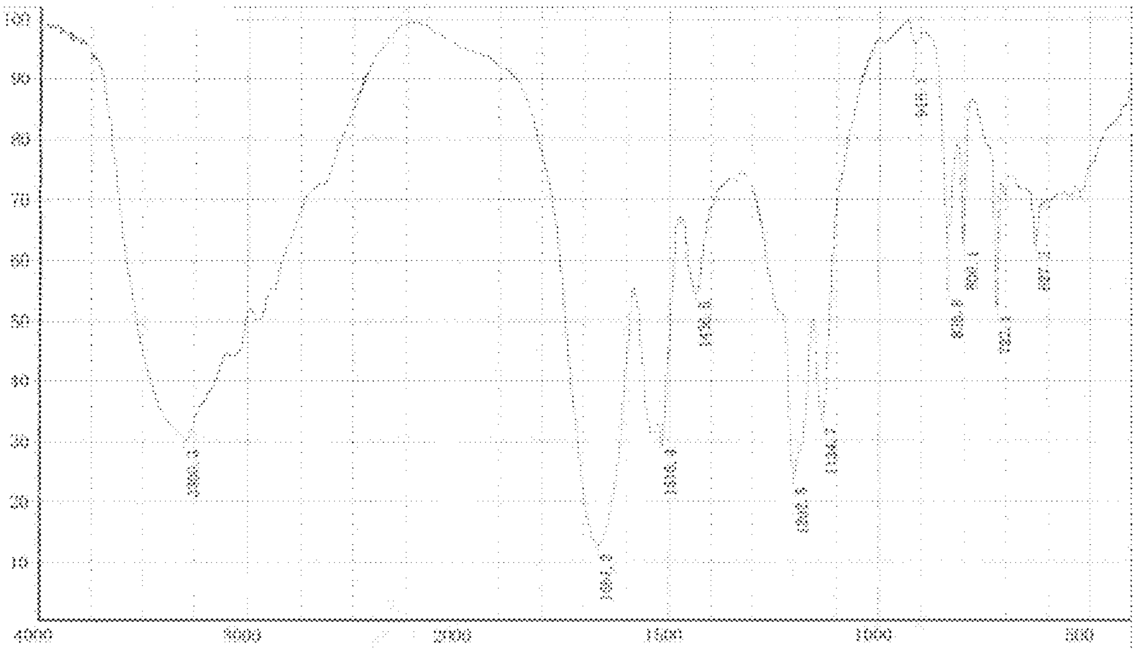
FIG. 3 is an infrared IR detection spectrum of the cyclization reaction product in Example 1.

Upon mass spectrometry detection, the detection pattern was as shown in FIG. 1. Its purity was greater than 95%, and its recovery rate was 91%. Upon HPLC detection, the detection pattern was as shown in FIG. 2. Upon infrared IR detection, the detection pattern was as shown in FIG. 3, showing there were the characteristic peaks of triazole (3,100 $cm^{-1}$, 1,400 $cm^{-1}$, 1,100 $cm^{-1}$, 700 $cm^{-1}$), and no characteristic peaks of azide (2,100 $cm^{-1}$) and alkyne (2,200 $cm^{-1}$).

Using the same method, the head-to-tail cyclic peptides or N-terminal and C-terminal cyclized peptides of Hst2-Hst12 could be obtained sequentially, which would not be described again here.

Example 2 Preparation of homopropynylglycine-Hst1 Cyclic Peptide

The preparation method of this example was:

1. an alkynyl group and a protective group Fmoc were introduced onto glycine, and an azide group and a protective group Fmoc were introduced onto lysine to obtain a Fmoc-propynylglycine (of Formula 21) for connecting at the C-terminal (in this example the Fmoc-propynylglycine purchased from Merck KGaA was directly used) and a Fmoc-azidolysine (of Formula 19) for connecting at the N-terminal (in this example the Fmoc-azidolysine purchased from Merck KGaA was directly used) respectively, and structural formulas of them were as shown below:

Formula 21

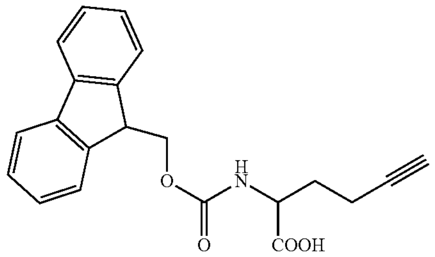

Formula 19

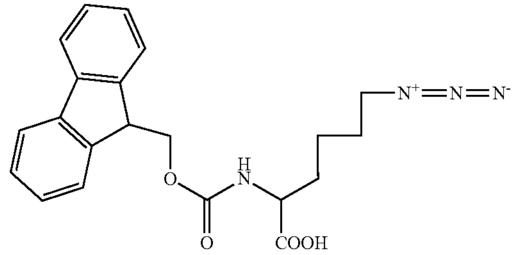

2. on the basis of the Fmoc-azidolysine, from right to left, the linear amino acids of Hst1 were synthesized step by step by adopting a solid-phase polypeptide synthesis (SPPS) method, and the Fmoc-propynylglycine was connected to the C-terminal of the Hst1; and
3. the Hst1 linear polypeptide prepared in the step 2 was utilized to prepare a Hst1 cyclic peptide through a copper-catalyzed azido-alkyne cycloaddition reaction, where the preparation method was conducted according to the method provided in Example 1.

451 mg of a propargylglycine-Hst1 cyclic peptide was prepared.

The structural formula of the propynylglycine-Hst1 cyclic peptide was as shown in Formula 22:

Formula 22

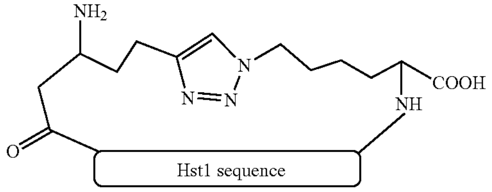

Upon mass spectrometry detection, its purity was greater than 95%, and its recovery rate was 90%. Upon infrared IR detection, it showed there were the characteristic peaks of triazole (3,100 $cm^{-1}$, 1,400 $cm^{-1}$, 1,100 $cm^{-1}$, 700 $cm^{-1}$), and no characteristic peaks of azide (2,100 $cm^{-1}$) and alkyne (2,200 $cm^{-1}$).

Using the same method, the head-to-tail cyclic peptides or N-terminal and C-terminal cyclized peptides of Hst2-Hst12 could be obtained sequentially, which would not be described again here.

Example 3 Preparation of bishomopropynylglycine-Hst1 Cyclic Peptide

The preparation method of this example was:

1. an alkynyl group and a protective group Fmoc were introduced onto glycine, and an azide group and a protective group Fmoc were introduced onto lysine to obtain a Fmoc-propynylglycine (of Formula 23) for connecting at the C-terminal (in this example the Fmoc-propynylglycine purchased from Merck KGaA was directly used) and a Fmoc-azidolysine (of Formula 19) for connecting at the N-terminal (in this example the Fmoc-azidolysine purchased from Merck KGaA was directly used) respectively, and structural formulas of them were as shown below:

Formula 23

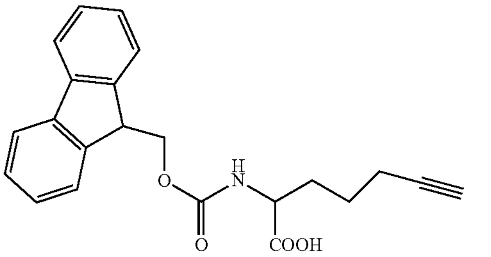

Formula 19

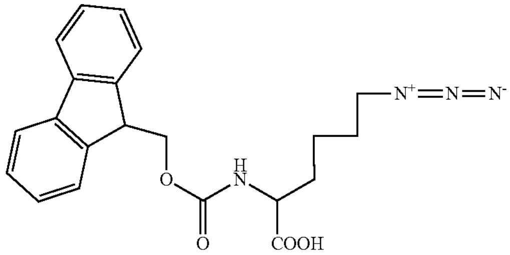

2. on the basis of the Fmoc-azidolysine, from right to left, the linear amino acids of Hst1 were synthesized step by step by adopting a solid-phase polypeptide synthesis (SPPS) method, and the Fmoc-propynylglycine was connected to the C-terminal of the Hst1; and
3. the Hst1 linear polypeptide prepared in the step 2 was utilized to prepare a Hst1 cyclic peptide through a copper-catalyzed azido-alkyne cycloaddition reaction, where the preparation method was conducted according to the method provided in Example 1.

453 mg of a propargylglycine-Hst1 cyclic peptide was prepared.

The structural formula of the propynylglycine-Hst1 cyclic peptide was as shown in Formula 24:

Formula 24

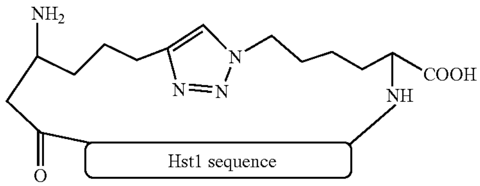

Upon mass spectrometry detection, its purity was greater than 95%, and its recovery rate was 91%. Upon infrared IR detection, it showed there were the characteristic peaks of triazole (3,100 $cm^{-1}$, 1,400 $cm^{-1}$, 1,100 $cm^{-1}$, 700 $cm^{-1}$), and no characteristic peaks of azide (2,100 $cm^{-1}$) and alkyne (2,200 $cm^{-1}$).

Using the same method, the head-to-tail cyclic peptides or N-terminal and C-terminal cyclized peptides of Hst2-Hst12 could be obtained sequentially, which would not be described again here.

Example 4 Effect of Polypeptide Concentration on Cyclization Reaction

In this example, a propynylglycine-Hst1 cyclic peptide was prepared according to the method provided in Example 1. 100, 300, 500, and 700 mg of linear polypeptides were respectively added into 20 ml of a mixed solution of acetonitrile and dimethyl sulfoxide formulated in a ratio of 4:1 for reaction, the time required for the reaction was recorded, the yield of the reaction product was detected by HPLC, and the proportion of side reactions in the reaction products (including by-products of intermolecular condensation, such as a diploid, triploid and tetraploid, etc., and the proportion of by-products in the head-to-tail cyclic peptides or N-terminal and C-terminal cyclized peptides of the polypeptide was calculated through molecular weights confirmed by mass spectrometry) was calculated, so as to investigate the effects of different polypeptide concentrations on the cyclization reaction. The results were as shown in Table 1.

TABLE 1

Effect of different added amounts of linear polypeptides on cyclization reaction

| Added amounts of linear peptide (mg) | Reaction time (min) | Yield (%) | Proportion of side reactions (%) |
|---|---|---|---|
| 100 | 40 | 60 | 35 |
| 300 | 40 | 75 | 23 |
| 500 | 40 | 91 | 3 |
| 700 | 80 | 82 | 14 |

As could be seen from Table 1 that, different added amounts of the linear polypeptide have a significant effect on the cyclization reaction. As the added amount of the linear polypeptide increased, the reaction speed slowed down, and the yield and the proportion of side reactions also changed accordingly, where when the added amount of the linear polypeptide was 500 mg, the reaction speed was still fast, and the yield reached 91% and the proportion of side reactions was very low. Therefore, in a 20 ml solvent, the added amount of the most preferred linear polypeptide was 500 mg.

Example 5

Effect of Different Solvents on Cyclization Reaction

In this example, a propynylglycine-Hst1 cyclic peptide was prepared according to the method provided in Example 1. Different solvents as shown in Table 2 were used for reaction, the time required for the reaction was recorded, the yield of the reaction product was detected by HPLC, and the proportion of side reactions in the reaction products was calculated, so as to investigate the effects of different solvents on the cyclization reaction. The results were as shown in Table 2.

TABLE 2

Effects of different solvents on cyclization reaction

| Solvent | Reaction time (min) | Yield (%) | Proportion of side reactions (%) |
|---|---|---|---|
| Methanol | 110 | 59 | 35 |
| t-butanol | 90 | 57 | 36 |
| Dimethyl sulfoxide | 70 | 64 | 31 |
| Acetonitrile | 100 | 56 | 39 |
| Acetonitrile:dimethyl sulfoxide (1:1) | 90 | 78 | 18 |
| Acetonitrile:dimethyl sulfoxide (2:1) | 80 | 82 | 14 |
| Acetonitrile:dimethyl sulfoxide (4:1) | 40 | 91 | 3 |
| Acetonitrile:dimethyl sulfoxide (8:1) | 60 | 81 | 16 |

As could be seen from Table 2, different solvents have a significant effect on the cyclization reaction, mainly because the steric hindrance, electrical property, polarity, protonicity, hydrogen bonding ability and proportion produced by different solvents were different, which affected the reaction speed and side reaction by-products such as dimer and trimer polymers and decomposition products, etc. Therefore, it was preferred to use acetonitrile:dimethyl sulfoxide (4:1) as the solvent.

Example 6 Effects of Different Resins on Cyclization Reaction

In this example, a propynylglycine-Hst1 cyclic peptide was prepared according to the method provided in Example 1. A total of 8 resins, Wang Resin, Rink Amide AM Resin, Rink Amide MBHA Resin, 2-Chlorotrityl Resin, PEGylated Rink-modified TentaGel (TGR) resin, Aminomethyl Resin, Sieber Amide Resin, PAM Resin, were respectively adopted for reaction, the time required for the reaction was recorded, the yield of the reaction product was detected by HPLC, and the proportion of side reactions in the reaction products was calculated, so as to investigate the effects of different resins on the cyclization reaction. The results were as shown in Table 3.

TABLE 3

Effects of different resins on cyclization reaction

| Resin type | Reaction time (min) | Yield (%) | Proportion of side reactions (%) |
|---|---|---|---|
| Wang Resin | 40 | 60 | 34 |
| Rink Amide AM Resin | 40 | 85 | 15 |
| Rink Amide MBHA Resin | 40 | 91 | 3 |
| 2-Chlorotrityl Resin | 80 | 72 | 19 |
| PEGylated Rink-modified TentaGel (TGR) resin | 70 | 57 | 39 |
| Aminomethyl Resin | 80 | 55 | 42 |
| Sieber Amide Resin | 85 | 68 | 28 |
| PAM Resin | 70 | 66 | 31 |

As could be seen from Table 3, the selection of different resins had a significant effect on the cyclization reaction, and the reaction time, yield and proportion of side reactions all changed significantly. The Rink Amide MBHA Resin was the most preferred, which could achieve a product yield of greater than 91% and a proportion of side reactions reduced to 3%. It could be seen that binding with the Rink Amide MBHA Resin could prevent the occurrence of side reactions and improve the efficiency of the cyclization reaction.

Example 7 Effects of Different Catalysts on Cyclization Reaction

In this example, a propynylglycine-Hst1 cyclic peptide was prepared according to the method provided in Example 1. Cuprous iodide CuI, cuprous chloride CuCl, cuprous iodide/triethyl phosphite $CuI \cdot P(OEt)_3$, cuprous bromide, cuprous bromide dimethyl sulfide, tris(triphenylphosphine) cuprous fluoride $[CuF(PPh_3)_3]$, tetrakis(acetonitrile)copper tetrafluoroborate $[Cu(MeCN)_4]BF_4$, tetrakis(acetonitrile) copper hexafluorophosphate $[Cu(MeCN)_4]PF_6$ were respectively used as catalysts for reaction, the time required for the reaction was recorded, the yield of the reaction product was detected by HPLC, and the proportion of side reactions in the reaction products was calculated, so as to investigate the effects of different catalysts on the cyclization reaction. The results were as shown in Table 4.

TABLE 4

Effects of different catalysts on cyclization reaction

| Catalyst | Reaction time (min) | Yield (%) | Proportion of side reactions (%) |
|---|---|---|---|
| Cuprous iodide | 40 | 91 | 3 |
| Cuprous chloride | 70 | 85 | 11 |
| Cuprous iodide/triethyl phosphite | 50 | 52 | 37 |
| Cuprous bromide | 80 | 72 | 22 |
| Cuprous bromide dimethyl sulfide | 60 | 65 | 33 |
| Tris(triphenylphosphine)cuprous fluoride | 80 | 66 | 27 |
| Tetrakis(acetonitrile)copper tetrafluoroborate | 70 | 57 | 32 |
| Tetrakis(acetonitrile)copper hexafluorophosphate | 70 | 49 | 38 |

As could be seen from Table 4, the selection of different catalysts had a significant effect on the cyclization reaction, and the reaction time, yield, and proportion of side reactions all changed significantly. Therefore, cuprous iodide was the most preferred catalyst.

Example 8 Effects of Different Ligands on Cyclization Reaction

In this example, a propynylglycine-Hst1 cyclic peptide was prepared according to the method provided in Example 1. 2,6-lutidine, diethylamine, triethylamine, n-propylamine, diisopropylamine, tributylamine, diisopropylethylamine DIPEA, and dimethylaminopyridine DMAP were respectively used as ligands for reaction. The time required for the reaction was recorded, the yield of the reaction product was detected by HPLC, and the proportion of side reactions in the reaction products (including by-products of intermolecular condensation, such as a diploid, triploid and tetraploid, etc., and the proportion of by-products in the head-to-tail cyclic peptides or N-terminal and C-terminal cyclized peptides of the polypeptide was calculated through molecular weights confirmed by mass spectrometry) was calculated, so as to investigate the effects of different ligands on the cyclization reaction. The results were as shown in Table 5.

TABLE 5

Effects of different ligands on cyclization reaction

| Ligand | Reaction time (min) | Yield (%) | Proportion of side reactions (%) |
|---|---|---|---|
| 2,6-lutidine | 40 | 91 | 3 |
| Diethylamine | 70 | 85 | 15 |
| Triethylamine | 50 | 52 | 37 |
| n-propylamine | 80 | 72 | 22 |
| Diisopropylamine | 60 | 66 | 32 |
| Tributylamine | 80 | 58 | 35 |
| Diisopropylethylamine DIPEA | 60 | 73 | 17 |
| Dimethylaminopyridine DMAP | 70 | 69 | 29 |

As could be seen from Table 5, the selection of different ligands had a significant effect on the cyclization reaction, and the reaction time, yield, and proportion of side reactions all changed significantly. Therefore, 2,6-lutidine was the most preferred ligand, which could significantly shorten the reaction time, increase the yield, and reduce the proportion of side reactions.

Example 9 Effects of Reaction Conditions on Cyclization Reaction

In this example, a propynylglycine-Hst1 cyclic peptide was prepared according to the method provided in Example 1. Different reaction conditions as shown in Table 6 were respectively adopted for reaction. The time required for the reaction was recorded, the yield of the reaction product was detected by HPLC, and the proportion of side reactions in the reaction products (including by-products of intermolecular condensation, such as a diploid, triploid and tetraploid, etc., and the proportion of by-products in the head-to-tail cyclic peptides or N-terminal and C-terminal cyclized peptides of the polypeptide was calculated through molecular weights confirmed by mass spectrometry) was calculated, so as to investigate the effects of different reaction conditions on the cyclization reaction. The results were as shown in Table 6.

TABLE 6

Effects of different reaction conditions on cyclization reaction

| Ligand | Reaction time (min) | Yield (%) | Proportion of side reactions (%) |
|---|---|---|---|
| Blowing with nitrogen for 5 minutes, at 25° C. | 40 | 91 | 3 |
| Blowing with nitrogen for 5 minutes, at 50° C. | 70 | 85 | 12 |
| Blowing with nitrogen for 5 minutes, at 100° C. | 50 | 52 | 42 |
| Blowing with nitrogen for 5 minutes, with microwave | 80 | 72 | 20 |
| No nitrogen blowing, at 25° C. | 40 | 9 | 80 |

As could be seen from Table 6, the selection of different reaction conditions had a significant effect on the cyclization reaction, and the reaction speed, purity, and proportion of side reactions all changed significantly. Therefore, the most preferred reaction condition was blowing with nitrogen for 5 minutes, at 25° C.

Example 10 Effects of Cyclic Peptide Hst1 on Wound Repair

This example adopted the propargylglycine-Hst1 cyclic peptide (Click-Histatin1) provided in Example 1, a cyclized Hst1 (Sortase A-cyclic histatin1) prepared by the Sortase A enzymatic method provided in Example 4, and a linear peptide Hst1 (Histatin1) to conduct animal experiments to observe the effect of the propargylglycine-Hst1 on the healing rates of the wound surfaces of mice. The concentration of the linear peptide Hst1 was 10 μM, the concentration of the propargylglycine-Hst1 cyclic peptide was 0.1 μM, and the concentration of the cyclized Hst1 prepared by the Sortase A enzymatic method was each 0.1 μM.

1. Materials and Methods

This study was approved by the Medical Animal Center and Ethics Committee of the Southern Theater Command General Hospital of the Chinese People's Liberation Army.

1.1 Sources of Animals and Main Reagents and Instruments 12 healthy male special pathogen-free grade C57 BL/6 mice of 6-8 weeks old and weighing 22-28 g, were purchased from Guangdong Experimental Animal Center. Diaminobenzidine (DAB) was purchased from Wuhan Boster Biological Technology., Ltd., a rabbit anti-CD31 antibody, a mouse anti-VEGF antibody, a goat anti-rabbit secondary antibody and a goat anti-mouse secondary antibody were purchased from Servicebio, USA, and an ethylenediaminetetraacetic acid (EDTA) antigen buffer, an immunohistochemistry pen, bovine serum albumin, collagenase A, and hematoxylin were all purchased from Wuhan Servicebio Technology Co., Ltd., an inverted fluorescence microscope was purchased from Nikon Co., Ltd., Japan, a dehydrator was purchased from Wuhan Junjie Electronics Co., Ltd., and a paraffin slicing machine was purchased from SHANGHAI Leica Instrument Co., Ltd.

1.2 Animal Grouping and Handling 12 healthy male special pathogen-free grade C57 BL/6 mice (purchased from Guangdong Experimental Animal Center) of 6-8 weeks old and weighing 22-28 g. They were intraperitoneally injected with 5 ml/kg of 1% pentobarbital sodium for anesthesia. After the mice had no corneal reflex, the hair on their backs was carefully removed and disinfected with alcohol. 21 cm×1 cm full-thickness skin defect wound surfaces were prepared on the back of each mouse by using a circular skin punch. The 12 mice were divided into a Control (blank) group with 3 mice, a 10 μM linear peptide Hst1 (Histatin1) group with 3 mice, a 0.1 μM propynylglycine-Hst1 cyclic peptide (Click-Histatin1) group with 3 mice, and a 0.1 μM cyclized Hst1 prepared by a Sortase A enzymatic method (Sortase A-cyclic histatin1) group with 3 mice, according to a random number table method. Each wound surface was added with 0.5 ml of four drugs respectively, and administration was conducted every day until the wound surfaces of the experimental groups healed. Photographs were taken on days 0, 3, 5, 7, and 10 after surgery, and wound tissues were sampled on day 10 for subsequent pathological staining.

1.3 Observation Indicators 1.3.1 Healing Rate of Wound Surfaces

Figure 4:
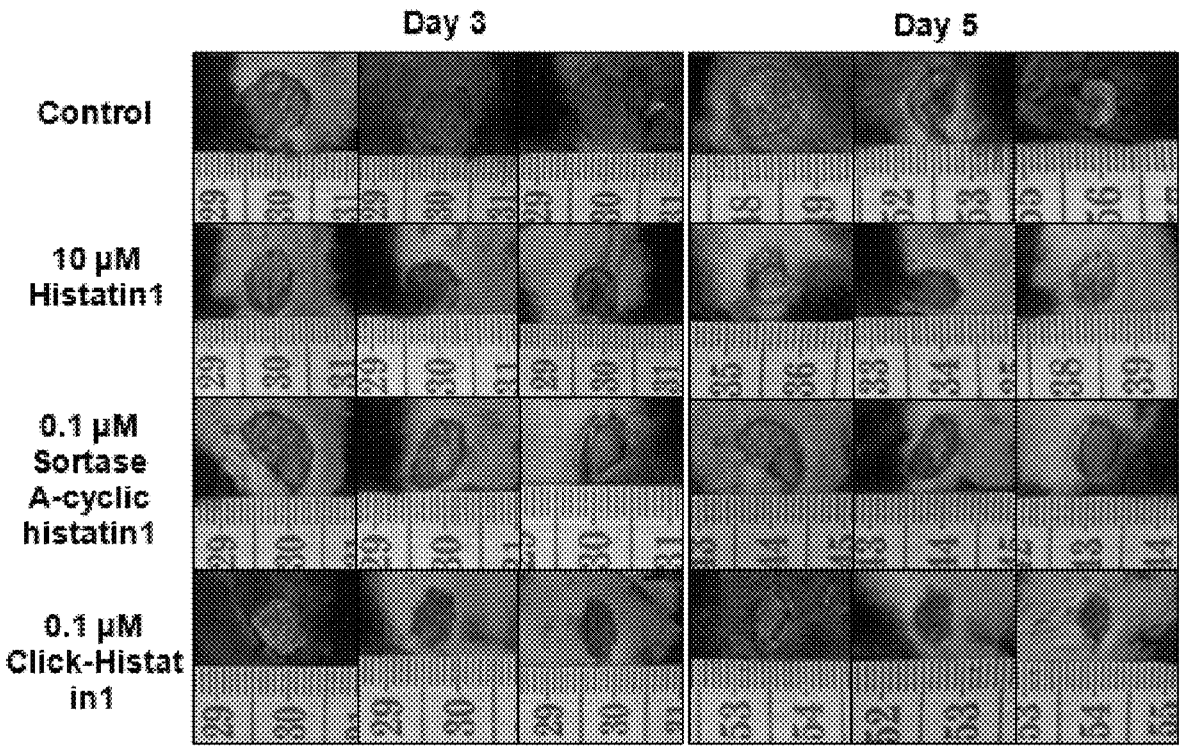
FIG. 4 is a photograph of the healing status of wound surfaces of mice in four groups of Example 10 on days 3 and 5.
Figure 5:
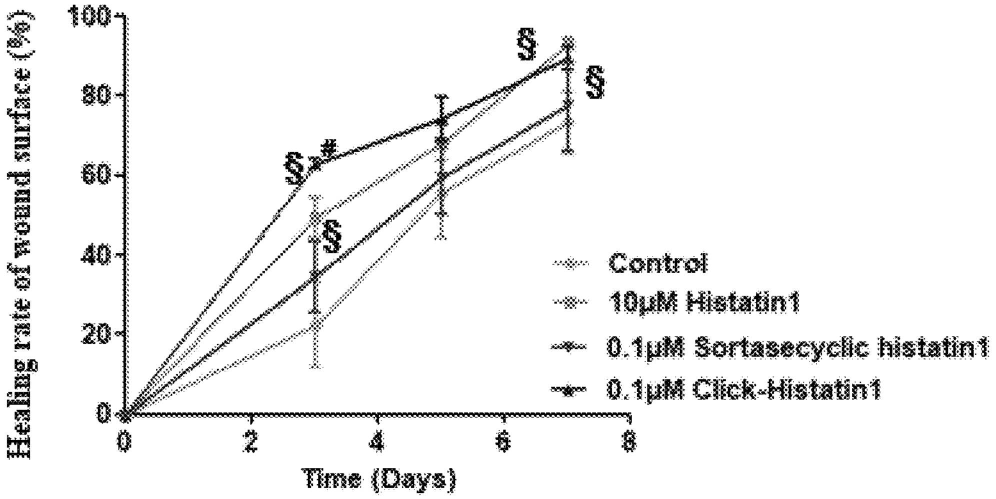
FIG. 5 is a schematic diagram comparing the healing rates of the wound surfaces of the mice in the four groups on days 3, 5, and 7 in Example 10.

On days 0, 3, 5, 7, and 10 after injury, the general condition of wound healing of the mice was observed and photographed with a digital camera (see FIG. 4), and the wound healing rate was calculated (see FIG. 5). Wound healing rate=(wound area immediately after injury−unhealed wound area at each time point)+wound area immediately after injury×100%.

1.3.2 Histological Morphology Detection

The wound specimens were fixed in 4% paraformaldehyde for 48 hours, rinsed with tap water for 10 minutes, dehydrated with graded ethanol, permeabilized with xylene, and embedded in paraffin to prepare 4 μm thick sections. Some sections were taken for HE staining and Masson staining, and observed for the thickness of the granulation tissue, the length of the dermal gap, and the newly grown collagen of the wound surface under an inverted fluorescence microscope at 40×, 100×, 200×, and 400× respectively (see FIGS. 6 and 7). 5 sections were taken from each mouse, and 5 fields of view were selected for each section. Data analysis was performed using the software Image-pro Plus.

1.3.3 Immunohistochemistry Staining

Paraffin sections prepared in 1.3.2 on day 10 after injury were dewaxed with xylene and rehydrated, subjected to antigen thermal repair with a 0.1 mol/L citric acid buffer (with a pH value of 6.0) for 20 minutes, treated with hydrogen peroxide with a volume fraction of 10% for inactivation of endogenous peroxidase for 10 minutes, and blocked with 50 g/L of bovine serum albumin for 2 hours. It was added with a rabbit anti-mouse CD31 primary antibody (with a dilution ratio of 1:300) and a mouse anti-VEGF (with a dilution ratio of 1:100), incubated overnight at 4° C., and washed with PBS. It was rewarmed for 1 hour, washed with PBS, added dropwise with ready-to-use biotinylated goat anti-mouse and goat anti-rabbit IgG secondary antibodies, incubated for 2 hours, and washed with PBS. It was subjected to DAB development, hematoxylin counterstaining, gradient ethanol dehydration, xylene permeabilization, and resin blocking. 5 sections were taken from each mouse, and 5 fields of view were selected for each section. The sections were observed under a 400× inverted fluorescence microscope, and analyzed for the number of CD31-positive blood vessels (see FIG. 8) and VEGF expression amounts (see FIG. 9, shown in brown) by using Image-pro Plus software.

1.4 Statistical Processing

The measurement data were expressed by M±SD, and the data were analyzed by one-way analysis of variance (ANOVA) and an independent samples T-test with SPSS 20.0 software to detect whether the differences among the groups were statistically significant, and a Bonferroni test was used for pairwise comparison. *p<0.05. p<0.01. *p<0.001 meant the difference was statistically significant, and p>0.05 was not statistically significant.

2 Results 2.1 Gross Observation and Wound Healing Rate

On days 3, 5, 7, and 10 after surgery, the wound surfaces in the four groups gradually shrank over time. The wound area of the 0.1 μM Click-Histatin1 group was smaller than those of the other three groups on both days 3 and 5 (FIG. 4). As could be seen from FIG. 5, on days 3, 5, and 7, the healing rate of the wound surface in the 0.1 μM Click-Histatin1 group was significantly higher than that of the Control group, and was significantly higher than that of the 0.1 μM Sortase A-cyclic histatin1 group on day 3 (P<0.05), and there was no significant difference in the healing rate of the wound surface between the 10 μM Histatin1 group and the 0.1 μM Click-Histatin 1 group on day 7. This was mainly because that the wound of the mouse had basically been repaired on day 7, and thus there was no reference significance; wherein § represented that there was a significant difference among the 0.1 μM Click-Histatin1 group, the 10 μM Histatin group and the Control group; and # represented that there was a significant difference between the 0.1 μM Click-Histatin1 group and the 0.1 μM Sortase A-cyclic histatin1 group (P<0.05). It could be seen that the 0.1 μM Click-Histatin1 group could better promote healing of the wound surface.

2.2 Histological Morphological Observation

Figure 6:
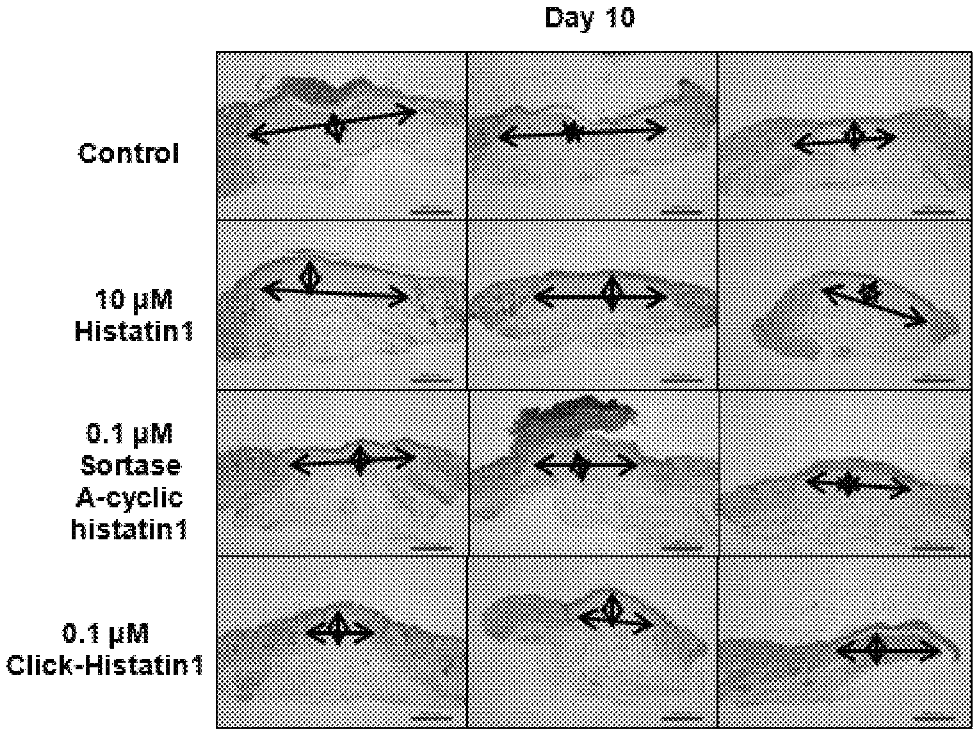
FIG. 6 is a HE-stained photograph of wound tissues in four groups of Example 10 on day 10.
Figure 7:
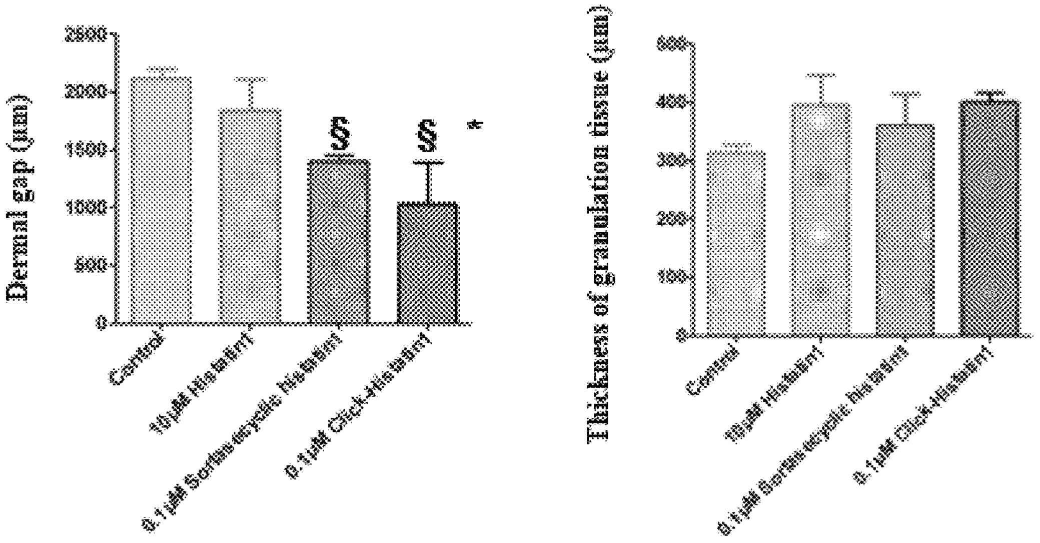
FIG. 7 is a schematic diagram comparing the thicknesses of newly-grown granulation tissues and the lengths of dermal gaps of the wounds in the four groups of Example 10, where (1) is a schematic diagram comparing the dermal gaps, and (2) is a schematic diagram comparing the thicknesses of the new granulation tissues.

In order to evaluate the thickness of the newly grown granulation tissue and the length of the dermal gap at the wound surface in the four groups, the wound tissue was stained with HE (FIG. 6). On day 10, the 0.1 μM Click-Histatin1 group had the shortest dermal gap length at both ends of the wound surface, followed by the 0.1 μM Sortase A-cyclic histatin 1 group, and the Control group and the 10 μM Histatin1 group had the longest dermal gap length (P<0.05) (FIG. 7(1)); and the thickness of the newly grown granulation tissue in the 0.1 μM Click-Histatin1 group was higher than those of the other three groups (FIG. 7(2)); wherein, § represented there was a significant difference among the 0.1 μM Click-Histatin1 group, the 0.1 μM Sortase A-cyclic histatin1 group and the Control group; and # represented there was a significant difference between the 0.1 μM Click-Histatin1 group and the 10 μM Histatin1 group (P<0.05). It showed that the 0.1 μM Click-Histatin1 group could better promote the regeneration of a granulation tissue at the wound surface.

Figure 8:
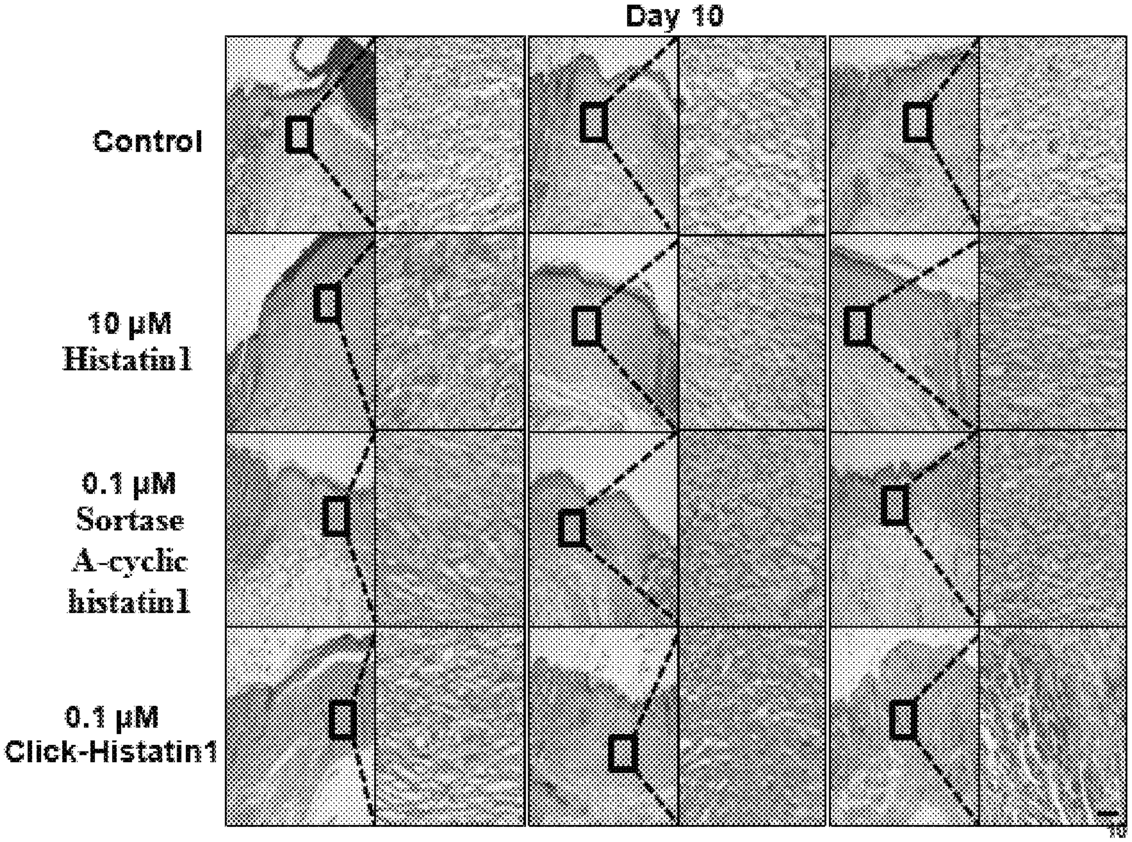
FIG. 8 is a Masson-stained photograph of the wound tissues of four groups of Example 10 on day 10.
Figure 9:
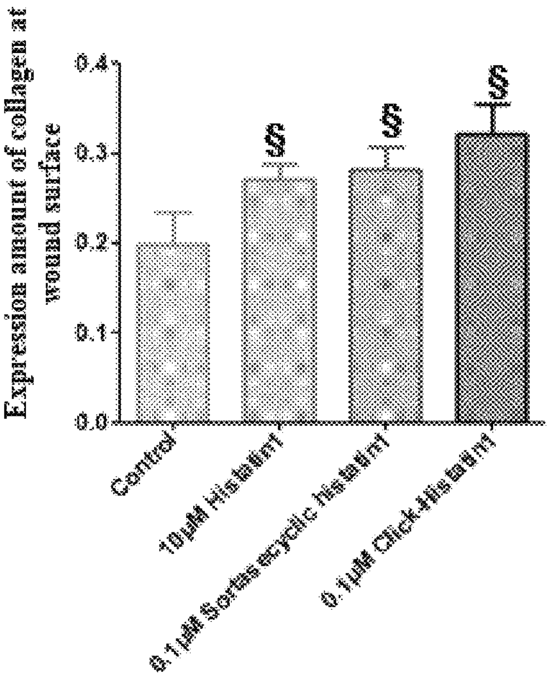
FIG. 9 is a schematic diagram comparing the wound collagen expression quantities of the wound tissues in the four groups of Example 10 on day 10.

In order to further evaluate the effects of the 0.1 μM Click-Histatin1, the 0.1 μM Sortase A-cyclic histatin1 and the 10 μM Histatin1 on newly growing collagen at the wound surface, the tissue specimens were stained with Masson (FIG. 8). As could be seen from FIG. 8, on day 10 after surgery, a large amount of newly grown collagen was deposited in the 0.1 μM Click-Histatin1 group, the 0.1 μM Sortase A-cyclic histatin1 group, and the 10 μM Histatin1 group, which was neatly arranged (blue indicated positive expression). The Scale bar=100 μm. Quantitative analysis showed (FIG. 9); on day 10, the expression amount of collagen at the wound surfaces of the 0.1 ηM Click-Histatin1 group, the 0.1 μM Sortase A-cyclic histatin1 group, and the 10 μM Histatin1 group was significantly higher than that of the Control group (P<0.05), and the collagen arrangement was regular and dense, with the highest expression amount of collagen at the wound surfaces of the 0.1 μM Click-Histatin1 group.

2.3 Immunohistochemical Staining

CD31 and VEGF were angiogenesis markers. The effects of the 0.1 μM Click-Histatin1, the 0.1 μM Sortase A-cyclic histatin1 and the 10 μM Histatin1 on angiogenesis at the wound surface were evaluated by immunohistochemical staining.

Figure 10:
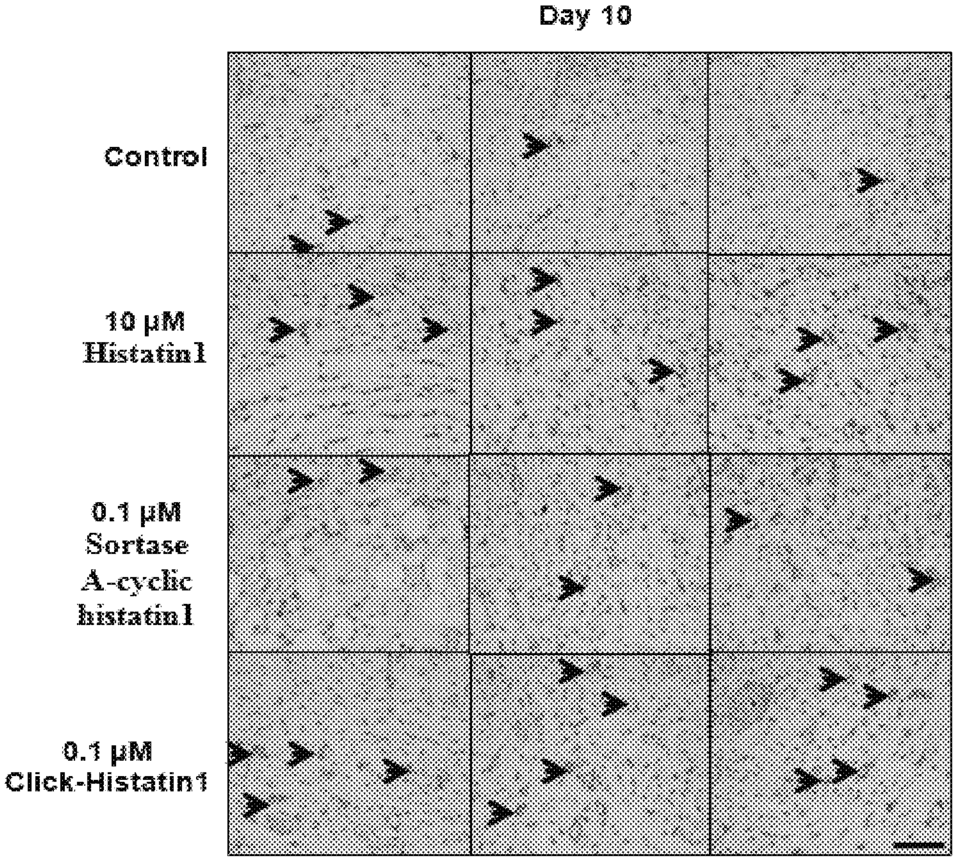
FIG. 10 is a schematic diagram of the results of the number of newly-grown CD31-positive blood vessels of wound tissues in the four groups of Example 10 on day 10.
Figure 11:
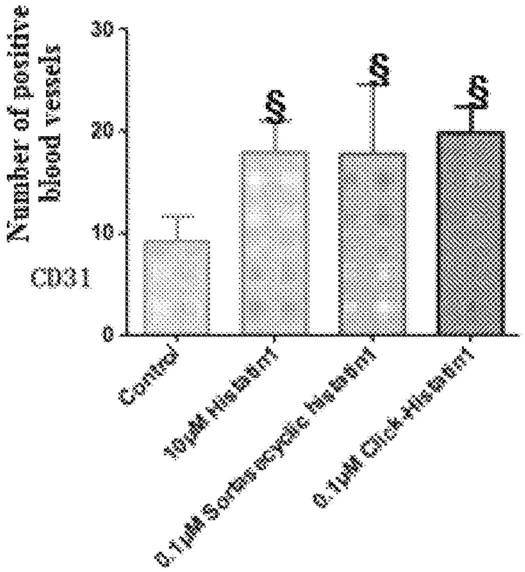
FIG. 11 is a schematic diagram comparing the quantitative analysis of the number of newly-grown CD31-positive blood vessels of the wound tissues of the four groups in Example 10 on day 10.

The results of immunohistochemical staining to evaluate the number of newly grown CD31-positive blood vessels in the 4 groups of wound surfaces were shown in FIGS. 10 and 11. As could be from FIG. 10, on day 10 after surgery, the number of CD31-positive blood vessels under each field of view in the 0.1 μM Click-Histatin1 group and the 10 μM Histatin1 group was significantly higher than that in the Control group (as indicated by the arrow). The scale bar=50 μm. As could be seen in FIG. 11, through quantitative analysis of the number of CD31-positive blood vessels, the number of newly grown blood vessels in the 0.1 μM Click-Histatin1 group was more (19.8±2.6), which was higher than those of the other three groups. § represented that there was a significant difference among the 0.1 μM Click-Histatin1 group, the 10 μM Histatin1 group, the 0.1 μM Sortase A-cyclic histatin1 group and the Control group ($P<0.05$).

Figure 12:
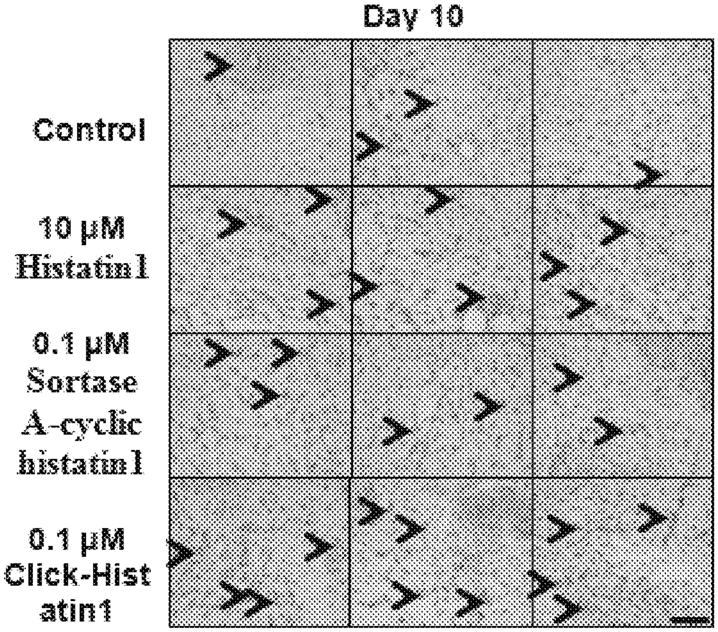
FIG. 12 is a schematic diagram of results of VEGF expression quantities of the wound tissues in the four groups of Example 10 on day 10.
Figure 13:
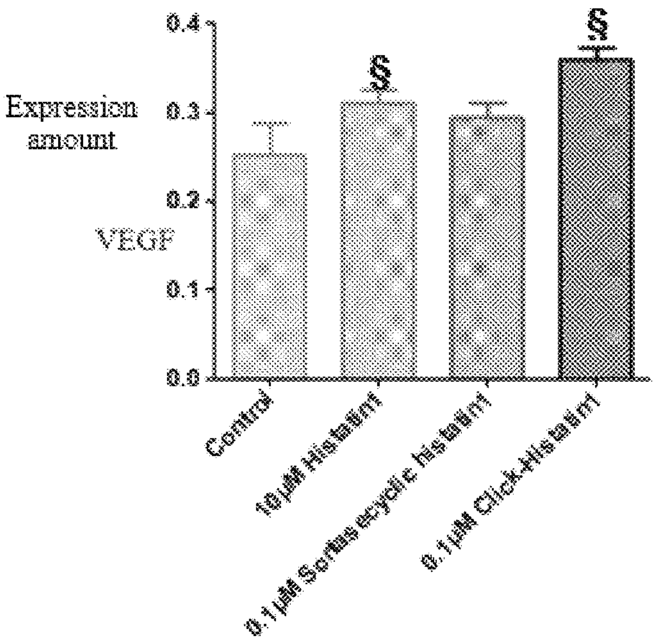
FIG. 13 is a schematic diagram comparing the quantitative analysis of VEGF expression quantities of the wound tissues in the four groups of Example 10 on day 10.

The results of immunohistochemical staining to evaluate the expression amount of VEGF at the wound surfaces of the 4 groups are shown in FIGS. 12 and 13. As could be seen from FIG. 12, on day 10 after surgery, the VEGF positive expression levels in the 0.1 μM Click-Histatin1 group and the 10 μM Histatin1 group were higher (as indicated by the arrow). The scale bar=50 μm. As could be seen from FIG. 13, VEGF quantitative analysis showed that the VEGF expression amount of the 0.1 μM Click-Histatin1 group and the 10 μM Histatin1 group was higher than that in the Control group, and the VEGF expression amount of the 0.1 μM Click-Histatin1 group was significantly higher than that of the 0.1 μM Sortase A-cyclic histatin1 group. § represented that there was a significant difference among the 0.1 μM Click-Histatin1 group, the 10 μM Histatin1 group and the Control group ($P<0.05$); and # represented that there was a significant difference between the 0.1 μM Click-Histatin1 group and the 0.1 μM Sortase A-cyclic histatin1 group ($P<0.05$).

Example 11 Scratching Experiment

Figure 14:
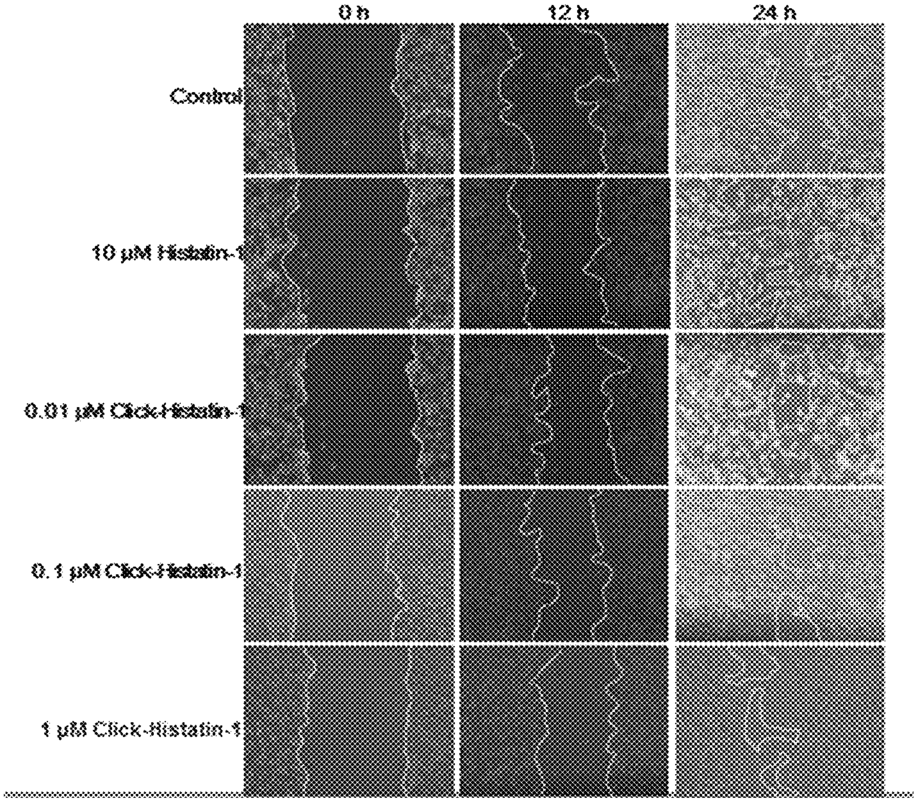
FIG. 14 is a microphotograph of five groups of scratch cells in Example 11 after culture for 0, 12, and 24 h.

At the same time, fibroblasts (NIH/3T3; GNM 6; Chinese Academy of Sciences, China) were plated into a 6-well plate at a number of $2\times10^6$/well and cultured to a density of 70-80%. The cells were starved for 8-12 hours before the experiment. Mitomycin C (Sigma Aldrich, USA) was added into the culture medium to make its concentration in the culture medium be 15 μg/ml, and the culture medium was changed after 3 hours of treatment. Scratching was conducted with a 200 μl pipette tip perpendicular to the bottom of the well-plate with the same force, and the well-plate was rinsed with PBS twice after scratching. Each well was added with an appropriate amount of a DEME medium (10% FBS, 1% double antibody), and except for the blank control group, each well was added with 10 μM of the linear Hst1, 0.01 μM of the propynylglycine-Hst1 cyclic peptide, 0.1 μM of the propynylglycine-Hst1 cyclic peptide and 1 μM of the propynylglycine-Hst1 cyclic peptide as experimental groups. At 0 hour, the cells in each group were photographed by using a microscope (Olympus, Japan). Then, the cells were placed at 37° C. and 5% $CO_2$ for culture, and photographed at 12 hours and 24 hours after the culture respectively (FIG. 14). The scratched area of each group was calculated by using imageJ (Rawak Software, Inc. Germany) software, and the scratch area at 0 hour was an initial scratch area. The scratch healing rate was calculated as follows:

$$W\ \%\ (\text{scratch healing rate}) = (W0 - Wt)/W0 \times 100\%$$

$$W0 = \text{initial scratched area}$$

$$Wt = \text{remaining scratched area}$$

Figure 15:
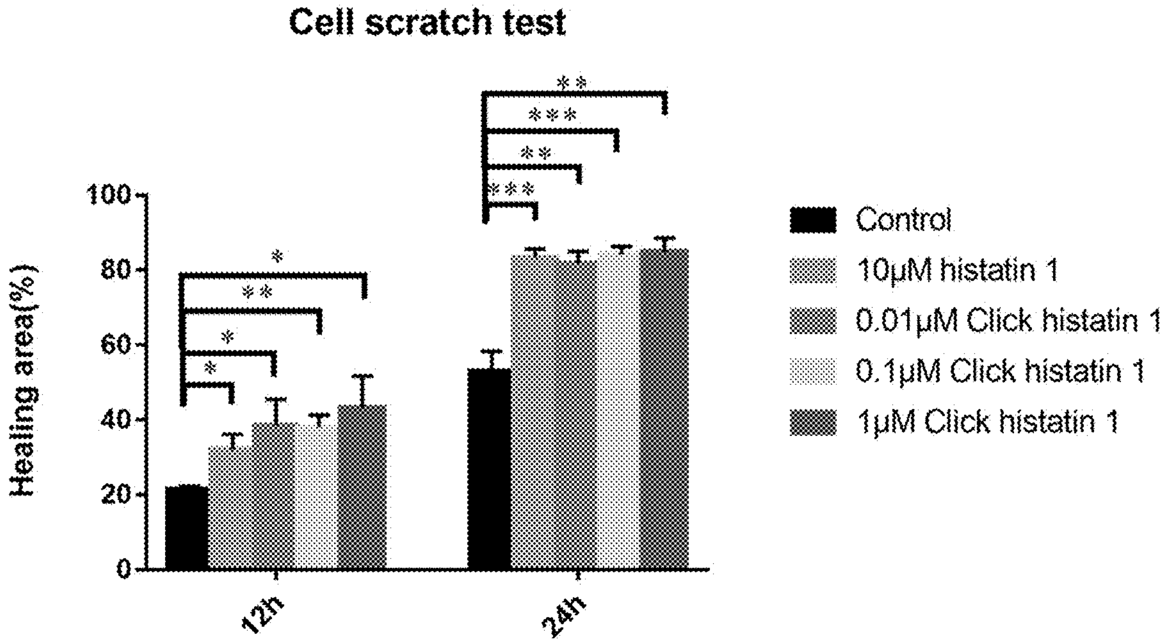
FIG. 15 is a schematic diagram of the statistical analysis results of five groups of wound surface areas using GraphPad Prism 5.0 in Example 11.

Statistical analysis of the wound area of each group was conducted with GraphPad Prism 5.0, and the results were shown in FIG. 15. As could be seen from FIG. 15 that the 0.01 μM propargylglycine-Hst1 cyclic peptide could still achieve or even exceed the effect of the 10 μM linear Hst1 on wound repair.

In this example, it was also proved by experiments that the 0.01 μM homopropynylglycine-Hst1 cyclic peptide and bishomopropynylglycine-Hst1 cyclic peptide could also achieve the effect of the 10 μM linear Hst1 on wound repair.

Example 12 Activity Comparison of Cyclic Peptides

In this example, the propynylglycine-Hst1 cyclic peptide, the homopropynylglycine-Hst1 cyclic peptide, the dihomopropynylglycine-Hst1 cyclic peptide and the linear Hst1 prepared in Examples 1, 2, and 3 were adopted respectively, the Sortase A enzymatic method and amide bond cyclization method provided by the literature of for example Sortase A as a tool for high-yield histatin cyclization, Jan G. M. Bolscher, The FASEB Journal. Research Communication were adopted to prepare the cyclized Hst1, the reaction speed was calculated, the yield of the reaction product was detected by HPLC, and the proportion of side reactions in the reaction product (including by-products of intermolecular condensation, such as a diploid, triploid and tetraploid, etc., and the proportion of by-products in the head-to-tail cyclic peptides or N-terminal and C-terminal cyclized peptides of the polypeptide was calculated through molecular weights confirmed by mass spectrometry) was calculated, and the activity was compared. The activity comparison method was to calculate the dosage needed to achieve the same pharmaceutical effect through the scratch experiment provided in Example 11, and the results were shown in Table 7.

TABLE 7

| Activity comparison | | | | |
|---|---|---|---|---|
| Polypeptide | Reaction speed | Yield (%) | Proportion of side reactions (%) | Dosage of agents required for scratch test (μM) |
| Propargylglycine-Hst1 cyclic peptide | 40 min | 91 | 3 | 0.01 |
| Homopropynylglycine-Hst1 cyclic peptide | 40 min | 90 | 5 | 0.009 |

TABLE 7-continued

| Activity comparison | | | | |
|---|---|---|---|---|
| Polypeptide | Reaction speed | Yield (%) | Proportion of side reactions (%) | Dosage of agents required for scratch test (μM) |
| Dihomopropynylglycine-Hst1 cyclic peptide | 40 min | 91 | 5 | 0.007 |
| Linear Hst1 | / | / | / | 10 |
| Hst1 cyclized through amide bonds | 72 h | 3 | 89 | — |
| Cyclized Hst1 prepared by Sortase A enzymatic method | 21 h | 90 | 9 | 0.12 |

As could be seen from Table 7 that the activity of the cyclic peptide prepared by the method provided by the present invention is more than 1000 times higher than that of the linear peptide, and the yield is higher, with very few side reactions, and only a catalyst amount of a cyclization reagent was needed, so the preparation cost was low. Using a traditional amide bond direct cyclization method, only 3% of a target cyclization product was obtained, and the reaction time was too long, requiring the use of equivalent-level catalysts and reaction reagents. The reason was that the Hst1 peptide chain was longer, and it was difficult for the traditional amide bond direct cyclization to achieve head-to-tail cyclization of long peptide chains. However, for the cyclized Hst1 prepared by the Sortase A enzymatic method, the catalytic efficiency was low (the molar equivalent was up to one-third of the substrate peptide), the reaction time was long (21 hours), and the prepared cyclic peptide had poor solubility. Furthermore, this method required a large recognition unit, required the introduction of redundant amino acid sequences at both ends of the head and the tail, which unnecessarily increased the length and sequence complexity of the original polypeptide, had poor atom economy, and had a risk of generating polymers; and its transpeptidase reaction mechanism was reversible, so that there was a risk of cleavage of the generated cyclic peptide; at the same time, because the Sortase A enzyme belonged to a bacterial enzyme, it was easy to contain bacterial product residues, thereby causing process safety issues such as immunogens and pathogenic microorganisms. Therefore, it is difficult for the Sortase A enzymatic method to prepare a high-purity Hst1 cyclic peptide that could be industrially produced on a large scale.

Example 13 Preparation of Propargylglycine-Hst1-MAD Cyclic Peptide

The preparation method of this example was:

1. an alkynyl group and a protective group Fmoc were introduced onto glycine, and an azide group and a protective group Fmoc were introduced onto lysine to obtain a Fmoc-propynylglycine (of Formula 18) for connecting at the C-terminal (in this example the Fmoc-propynylglycine purchased from Merck KGaA was directly used) and a Fmoc-azidolysine (of Formula 19) for connecting at the N-terminal (in this example the Fmoc-azidolysine purchased from Merck KGaA was directly used), and structural formulas of them were as shown below:

Formula 18

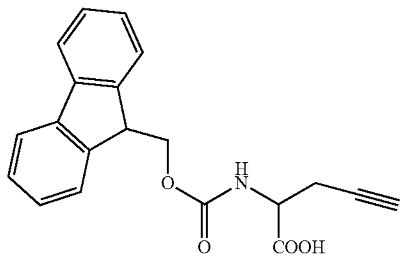

Formula 19

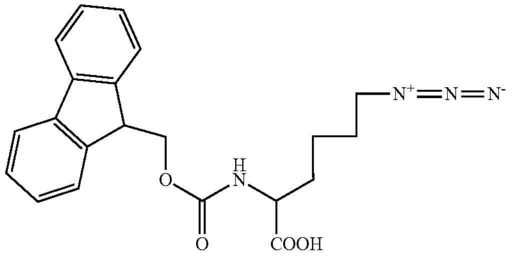

2. on the basis of the Fmoc-azidolysine, from right to left, the linear amino acids of Hst1-MAD (SEQ ID NO.1) were synthesized step by step by adopting a solid-phase polypeptide synthesis (SPPS) method, and the Fmoc-propynylglycine was connected to the C-terminal of the Hst1-MAD (SEQ ID NO.1); and
3. the Hst1-MAD linear polypeptide prepared in the step 2 was utilized to prepare a cyclic peptide (Click-Hst1-MAD) of Hst1-MAD (SEQ ID NO.1) through a copper-catalyzed azido-alkyne cycloaddition reaction, where the preparation method included the following steps:

1) 750 mg of the Hst1 linear polypeptide was placed in a container, added with 20 ml of a mixed solution of acetonitrile and dimethyl sulfoxide formulated in a ratio of 4:1;
2) the mixture was added with 750 mg of a resin Rink Amide MBHA Resin (purchased from Merck KGaA);
3) the mixture was added with 20 mM of cuprous iodide;
4) the mixture was added with 30 μl of 2,6-lutidine (dimethyl pyridine);
5) the mixture was blown with nitrogen for 5 minutes;
6) the container was covered tightly and sealed;
7) reaction was conducted under stirring at room temperature for 40 minutes;
8) it was washed twice with a saturated disodium ethylene diamine tetraacetate solution under shaking, for 10 minutes each time, to remove the washing liquid;

9) it was washed once with water, once with acetonitrile, once with dichloromethane, and once with diethyl ether, to remove the washing liquid;

10) it was subjected to vacuum drying for 1 hour;

11) cleaving: a mixed cleaving solution was formulated, including 95.5% of trifluoroacetic acid, 2% of a phenol aqueous solution, 2% of thioanisole, and 0.5% of triisopropylsilane, 20 ml of the mixed cleaving solution was taken and added into a sample obtained in the step 10), shaken for 3 hours to cleave a polypeptide from a template; and the polypeptide was filtered with cold diethyl ether, washed for 3 times, and dried; and 12) the polypeptide was purified by high performance liquid chromatography (HPLC), using an acetonitrile aqueous solution containing 0.1% (v/v) of trifluoro-acetic acid as a mobile phase for gradient elution and a detection wavelength of 210 nm.

707 mg of a propargylglycine-Hst1-MAD cyclic peptide was prepared.

The structural formula of the propynylglycine-Hst1-MAD cyclic peptide was as shown in Formula 25:

Formula 25

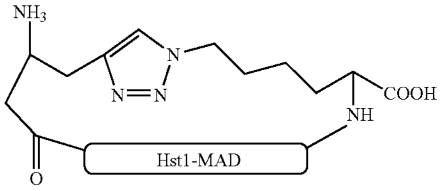

Figure 16:
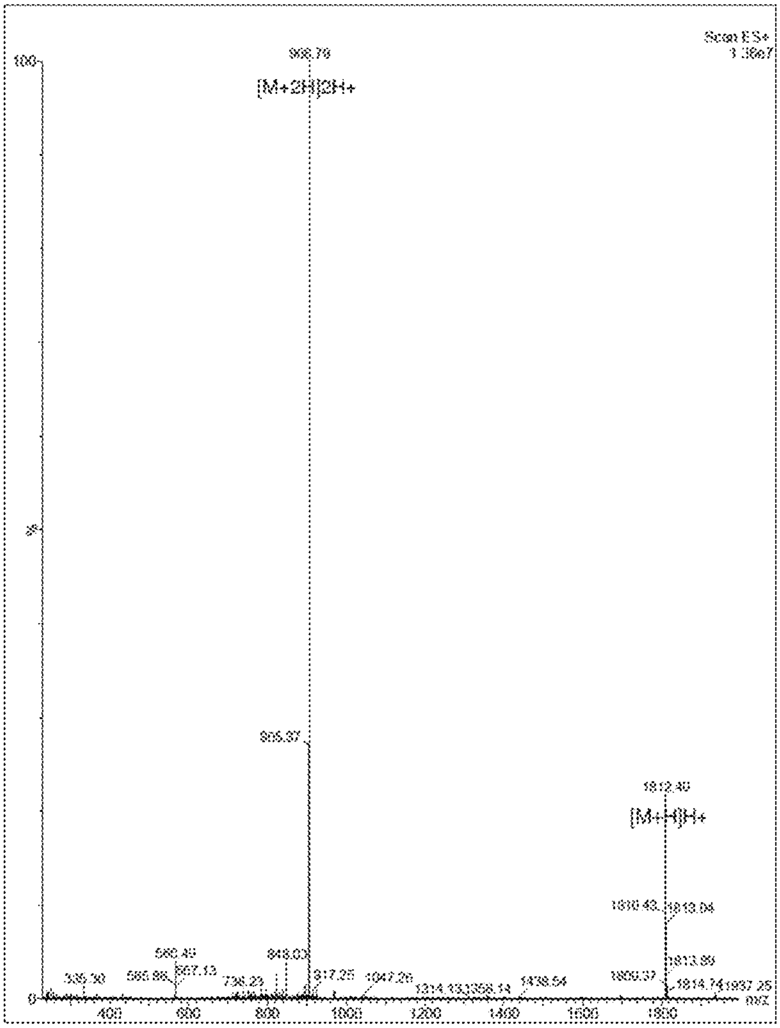
FIG. 16 is a mass spectrum MS detection pattern of a cyclization reaction product of Example 13.
Figure 17:
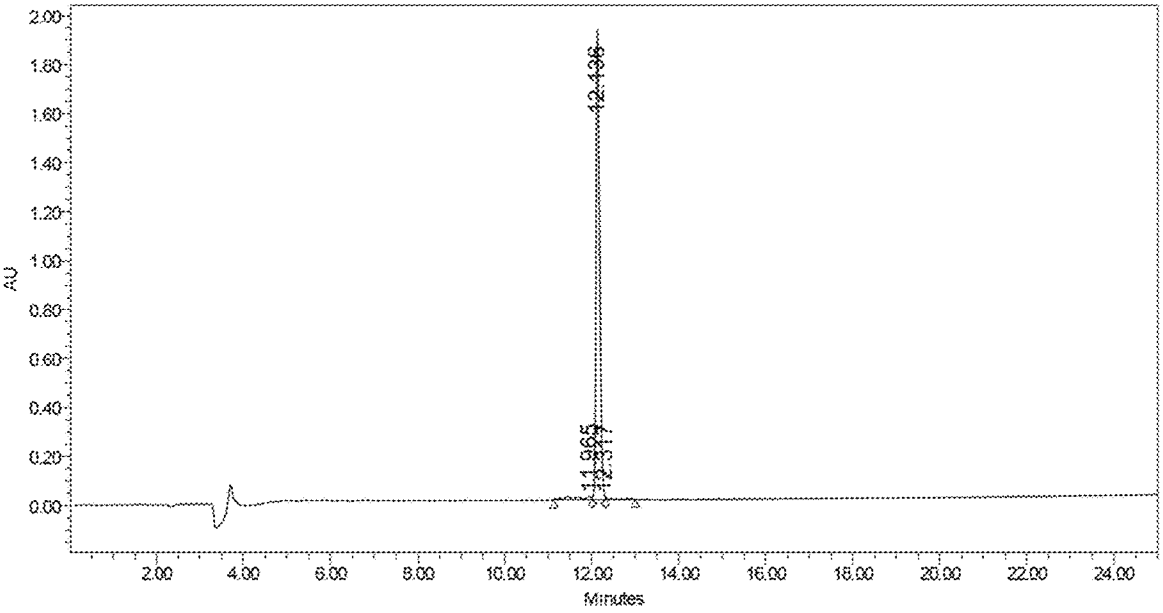
FIG. 17 is a high-performance liquid chromatography HPLC detection pattern of the cyclization reaction product of Example 13.
Figure 18:
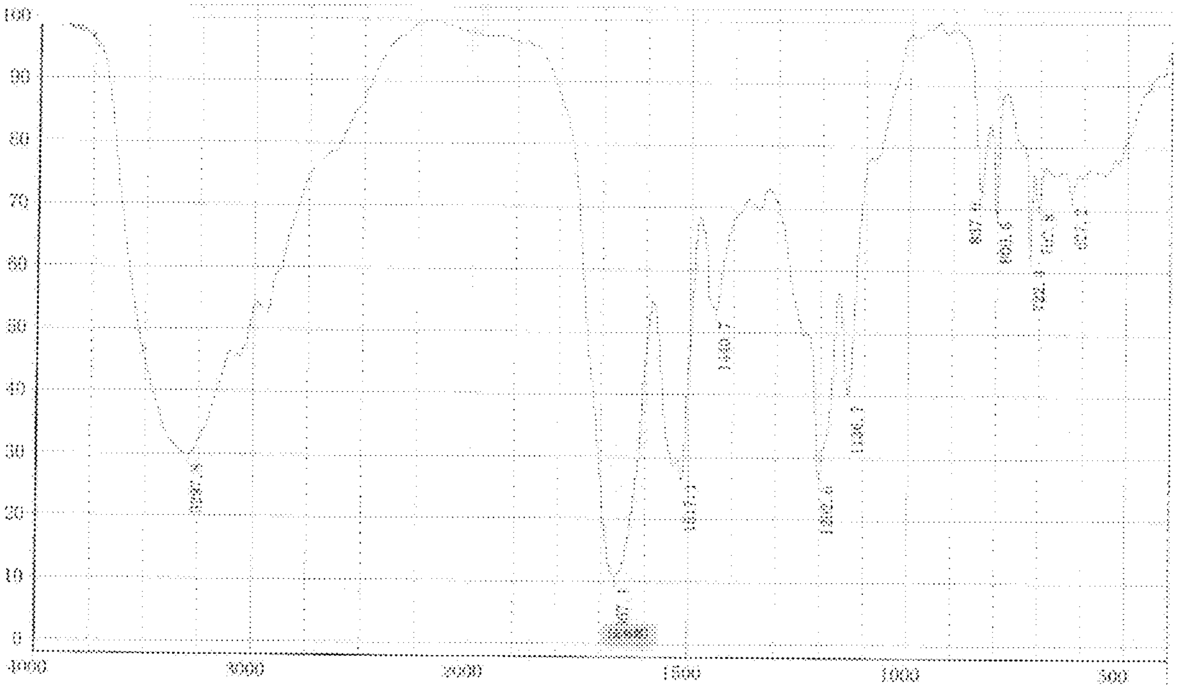
FIG. 18 is an infrared IR detection spectrum of the cyclization reaction product in Example 13.

Upon mass spectrometry detection, the detection pattern was as shown in FIG. 16. Its purity was greater than 95%, and its recovery rate was 94%. Upon HPLC detection, the detection pattern was as shown in FIG. 17. Upon infrared IR detection, the detection pattern was as shown in FIG. 18, showing there were the characteristic peaks of triazole (3,100 $cm^{-1}$, 1,400 $cm^{-1}$, 1,100 $cm^{-1}$, 700 $cm^{-1}$), and no characteristic peaks of azide (2,100 $cm^{-1}$) and alkyne (2,200 $cm^{-1}$).

Example 14 Preparation of Homopropynylglycine-Hst1-MAD Cyclic Peptide

The preparation method of this example was:

1. an alkynyl group and a protective group Fmoc were introduced onto glycine, and an azide group and a protective group Fmoc were introduced onto lysine to obtain a Fmoc-propynylglycine (of Formula 21) for connecting at the C-terminal (in this example the Fmoc-propynylglycine purchased from Merck KGaA was directly used) and a Fmoc-azidolysine (of Formula 19) for connecting at the N-terminal (in this example the Fmoc-azidolysine purchased from Merck KGaA was directly used) respectively, and structural formulas of them were as shown below:

Formula 21

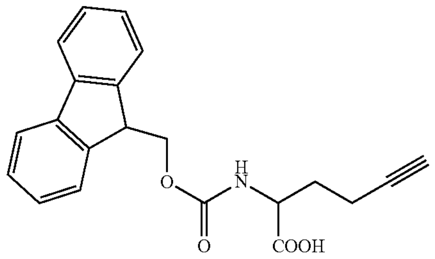

Formula 19

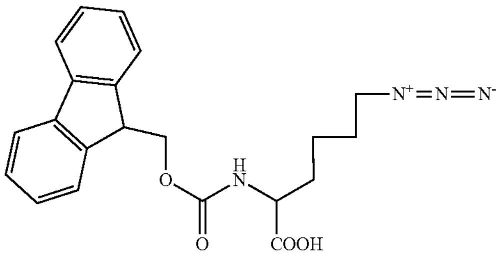

2. on the basis of the Fmoc-azidolysine, from right to left, the linear amino acids of Hst1-MAD (SEQ ID NO.1) were synthesized step by step by adopting a solid-phase polypeptide synthesis (SPPS) method, and the Fmoc-propynylglycine was connected to the C-terminal of the Hst1-MAD; and
3. the Hst1-MAD linear polypeptide prepared in the step 2 was utilized to prepare an Hst1-MAD cyclic peptide through a copper-catalyzed azido-alkyne cycloaddition reaction, where the preparation method was conducted according to the method provided in Example 1.

698 mg of a propargylglycine-Hst1-MAD cyclic peptide was prepared.

The structural formula of the propynylglycine-Hst1-MAD cyclic peptide was as shown in Formula 26:

Formula 26

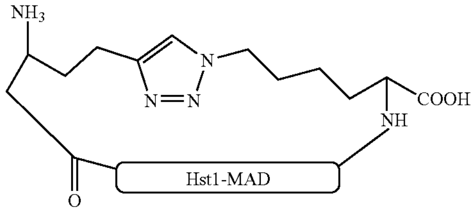

Upon mass spectrometry detection, its purity was greater than 95%, and its recovery rate was 93%. Upon infrared IR detection, it showed there were the characteristic peaks of triazole (3,100 $cm^{-1}$, 1,400 $cm^{-1}$, 1,100 $cm^{-1}$, 700 $cm^{-1}$), and no characteristic peaks of azide (2,100 $cm^{-1}$) and alkyne (2,200 $cm^{-1}$).

Example 15 Preparation of Bishomopropynylglycine-Hst1-MAD Cyclic Peptide

The preparation method of this example was:

1. an alkynyl group and a protective group Fmoc were introduced onto glycine, and an azide group and a protective group Fmoc were introduced onto lysine to obtain a Fmoc-propynylglycine (of Formula 23) for connecting at the C-terminal (in this example the Fmoc-propynylglycine purchased from Merck KGaA was directly used) and a Fmoc-azidolysine (of Formula 19) for connecting at the N-terminal (in this example the Fmoc-azidolysine purchased from Merck KGaA was directly used) respectively, and structural formulas of them were as shown below:

Formula 23

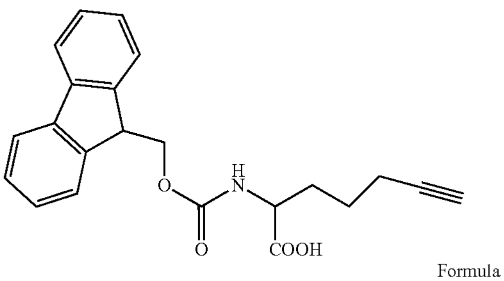

Formula 19

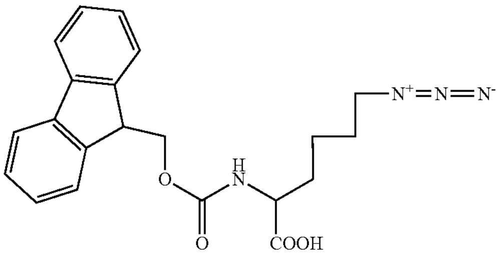

2. on the basis of the Fmoc-azidolysine, from right to left, the linear amino acids of Hst1-MAD (SEQ ID NO.1) were synthesized step by step by adopting a solid-phase polypeptide synthesis (SPPS) method, and the Fmoc-propynylglycine was connected to the C-terminal of the Hst1-MAD; and
3. the Hst1-MAD linear polypeptide prepared in the step 2 was utilized to prepare an Hst1-MAD cyclic peptide through a copper-catalyzed azido-alkyne cycloaddition reaction, where the preparation method was conducted according to the method provided in Example 1.

699 mg of a propargylglycine-Hst1-MAD cyclic peptide was prepared.

The structural formula of the propynylglycine-Hst1 cyclic peptide was as shown in Formula 27:

Formula 27

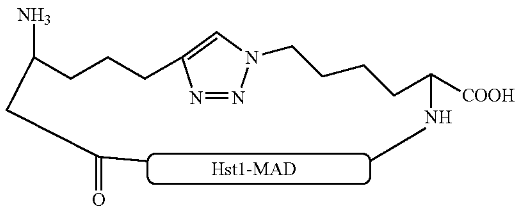

Upon mass spectrometry detection, its purity was greater than 95%, and its recovery rate was 93%. Upon infrared IR detection, it showed there were the characteristic peaks of triazole (3,100 $cm^{-1}$, 1,400 $cm^{-1}$, 1,100 $cm^{-1}$, 700 $cm^{-1}$), and no characteristic peaks of azide (2,100 $cm^{-1}$) and alkyne (2,200 $cm^{-1}$).

Example 16 Effect of Linear Oligopeptide Concentration on Cyclization Reaction In this example, a propynylglycine-Hst1 cyclic peptide was prepared according to the method provided in Example 13. 250, 500, 750 and 1,000 mg of linear oligopeptides were respectively added into 20 ml of a mixed solution of acetonitrile and dimethyl sulfoxide formulated in a ratio of 4:1 for reaction. The time required for the reaction was recorded, the yield of the reaction product was detected by HPLC, and the proportion of side reactions in the reaction products (including by-products of intermolecular condensation, such as a diploid, triploid and tetraploid, etc., and the proportion of by-products in the head-to-tail cyclic peptides or N-terminal and C-terminal cyclized peptides of the oligopeptide Hst1-MAD was calculated through molecular weights confirmed by mass spectrometry) was calculated, so as to investigate the effects of different linear Hst1-MAD oligopeptide concentrations on the cyclization reaction. The results were as shown in Table 8.

TABLE 8

Effects of different added amounts of linear Hst1-MAD oligopeptides on cyclization reaction

| Added amount of Linear oligopeptide (mg) | Reaction time (min) | Yield (%) | Proportion of side reactions (%) |
|---|---|---|---|
| 250 | 40 | 82 | 15 |
| 500 | 40 | 91 | 7 |
| 750 | 40 | 94 | 3 |
| 1000 | 60 | 80 | 16 |

As could be seen from Table 8 that, different added amounts of the linear Hst1-MAD oligopeptide had a significant effect on the cyclization reaction. As the added amount of the linear oligopeptide increased, the reaction speed slowed down, and the yield and the proportion of side reactions also changed accordingly, where when the added amount of the linear oligopeptide was 750 mg, the reaction speed was still fast, and the yield reached 94% and the proportion of side reactions was very low. Therefore, in a 20 ml solvent, the added amount of the most preferred linear oligopeptide was 750 mg.

Example 17 Effects of Different Solvents on Cyclization Reaction

In this example, a propynylglycine-Hst1-MAD cyclic peptide was prepared according to the method provided in Example 13. Different solvents as shown in Table 2 were used for reaction, the time required for the reaction was recorded, the yield of the reaction product was detected by HPLC, and the proportion of side reactions in the reaction products was calculated, so as to investigate the effects of different solvents on the cyclization reaction. The results were as shown in Table 9.

TABLE 9

Effects of different solvents on cyclization reaction

| Solvent | Reaction time (min) | Yield (%) | Proportion of side reactions (%) |
|---|---|---|---|
| Methanol | 120 | 44 | 51 |
| t-butanol | 90 | 54 | 41 |
| Dimethyl sulfoxide | 60 | 67 | 29 |

TABLE 9-continued

Effects of different solvents on cyclization reaction

| Solvent | Reaction time (min) | Yield (%) | Proportion of side reactions (%) |
|---|---|---|---|
| Acetonitrile | 90 | 57 | 40 |
| Acetonitrile:dimethyl sulfoxide (1:1) | 60 | 84 | 11 |
| Acetonitrile:dimethyl sulfoxide (2:1) | 40 | 94 | 3 |
| Acetonitrile:dimethyl sulfoxide (4:1) | 40 | 91 | 7 |
| Acetonitrile:dimethyl sulfoxide (8:1) | 60 | 89 | 9 |

As could be seen from Table 9, different solvents have a significant effect on the cyclization reaction, mainly because the steric hindrance, electrical property, polarity, protonicity, hydrogen bonding ability and proportion produced by different solvents were different, which affected the reaction speed and side reaction by-products such as dimer and trimer polymers and decomposition products, etc. Therefore, it was preferred to use acetonitrile:dimethyl sulfoxide (2:1) as the solvent.

Example 18 Effects of Different Resins on Cyclization Reaction

In this example, a propynylglycine-Hst1-MAD cyclic peptide was prepared according to the method provided in Example 13. A total of 8 resins, Wang Resin, Rink Amide AM Resin, Rink Amide MBHA Resin, 2-Chlorotrityl Resin, PEGylated Rink-modified TentaGel (TGR) resin, Aminomethyl Resin, Sieber Amide Resin, PAM Resin, were respectively adopted for reaction, the time required for the reaction was recorded, the yield of the reaction product was detected by HPLC, and the proportion of side reactions in the reaction products was calculated, so as to investigate the effects of different resins on the cyclization reaction. The results were as shown in Table 10.

TABLE 10

Effects of different resins on cyclization reaction

| Resin type | Reaction time (min) | Yield (%) | Proportion of side reactions (%) |
|---|---|---|---|
| Wang Resin | 40 | 72 | 24 |
| Rink Amide AM Resin | 40 | 83 | 15 |
| Rink Amide MBHA Resin | 40 | 94 | 3 |
| 2-Chlorotrityl Resin | 60 | 78 | 20 |
| PEGylated Rink-modified TentaGel (TGR) resin | 60 | 61 | 33 |
| Aminomethyl Resin | 70 | 53 | 41 |
| Sieber Amide Resin | 80 | 64 | 32 |
| PAM Resin | 60 | 60 | 34 |

As could be seen from Table 10, the selection of different resins had a significant effect on the cyclization reaction, and the reaction speed, yield and proportion of side reactions all changed significantly. The Rink Amide MBHA Resin was the most preferred, which could achieve a product yield of greater than 94% and a proportion of side reactions reduced to 3%. It could be seen that binding with the Rink Amide MBHA Resin could prevent the occurrence of side reactions and improve the efficiency of the cyclization reaction.

Example 19 Effects of Different Catalysts on Cyclization Reaction

In this example, a propynylglycine-Hst1-MAD cyclic peptide was prepared according to the method provided in Example 13. Cuprous iodide CuI, cuprous chloride CuCl, cuprous iodide/triethyl phosphite $CuI\cdot P(OEt)_3$, cuprous bromide, cuprous bromide dimethyl sulfide, tris(triphenylphosphine)cuprous fluoride $[CuF(PPh_3)_3]$, tetrakis(acetonitrile) copper tetrafluoroborate $[Cu(MeCN)_4]BF_4$, tetrakis (acetonitrile)copper hexafluorophosphate $[Cu(MeCN)_4]PF_6$ were respectively used as catalysts for reaction, the time required for the reaction was recorded, the yield of the reaction product was detected by HPLC, and the proportion of side reactions in the reaction products was calculated, so as to investigate the effects of different catalysts on the cyclization reaction. The results were as shown in Table 11.

TABLE 11

Effects of different catalysts on cyclization reaction

| Catalyst | Reaction time (min) | Yield (%) | Proportion of side reactions (%) |
|---|---|---|---|
| Cuprous iodide | 40 | 94 | 3 |
| Cuprous chloride | 60 | 89 | 9 |
| Cuprous iodide/triethyl phosphite | 40 | 56 | 41 |
| Cuprous bromide | 70 | 77 | 20 |
| Cuprous bromide dimethyl sulfide | 60 | 69 | 25 |
| Tris(triphenylphosphine)cuprous fluoride | 80 | 70 | 27 |
| Tetrakis(acetonitrile)copper tetrafluoroborate | 60 | 61 | 36 |
| Tetrakis(acetonitrile)copper hexafluorophosphate | 60 | 55 | 43 |

As could be seen from Table 11, the selection of different catalysts has a significant effect on the cyclization reaction. The reaction speed, yield, and the proportion of side reactions all changed significantly. Only when cuprous iodide was used as the catalyst, the product yield could reach 94%, and the proportion of side reactions was the lowest, so cuprous iodide was the most preferred catalyst.

Example 20 Effects of Different Ligands on Cyclization Reaction

In this example, a propynylglycine-Hst1-MAD cyclic peptide was prepared according to the method provided in Example 13. 2,6-lutidine, diethylamine, triethylamine, n-propylamine, diisopropylamine, tributylamine, diisopropylethylamine DIPEA, and dimethylaminopyridine DMAP were respectively used as ligands for reaction. The reaction time was recorded, the yield of the reaction product was detected by HPLC, and the proportion of side reactions in the reaction products was calculated, so as to investigate the effects of different ligands on the cyclization reaction. The results were as shown in Table 12.

TABLE 12

Effects of different ligands on cyclization reaction

| Ligand | Reaction time (min) | Yield (%) | Proportion of side reactions (%) |
|---|---|---|---|
| 2,6-lutidine | 40 | 94 | 3 |
| Diethylamine | 60 | 87 | 11 |
| Triethylamine | 50 | 66 | 31 |
| n-propylamine | 70 | 78 | 20 |
| Diisopropylamine | 60 | 70 | 26 |
| Tributylamine | 80 | 64 | 30 |

TABLE 12-continued

Effects of different ligands on cyclization reaction

| Ligand | Reaction time (min) | Yield (%) | Proportion of side reactions (%) |
|---|---|---|---|
| Diisopropylethylamine DIPEA | 60 | 79 | 20 |
| Dimethylaminopyridine DMAP | 60 | 81 | 15 |

As could be seen from Table 12, the selection of different ligands had a significant effect on the cyclization reaction, and the reaction speed, yield, and proportion of side reactions all changed significantly. Therefore, 2,6-lutidine was the most preferred ligand.

Example 21 Effects of Reaction Conditions on Cyclization Reaction

In this example, a propynylglycine-Hst1-MAD cyclic peptide was prepared according to the method provided in Example 13. Different reaction conditions as shown in Table 6 were used for reaction, the reaction time was recorded, the yield of the reaction product was detected by HPLC, and the proportion of side reactions in the reaction products was calculated, so as to investigate the effects of different reaction conditions on the cyclization reaction. The results were as shown in Table 13.

TABLE 13

Effects of different reaction conditions on cyclization reaction

| Ligand | Reaction time (min) | Yield (%) | Proportion of side reactions (%) |
|---|---|---|---|
| Blowing with nitrogen for 5 minutes, at 25° C. | 40 | 94 | 3 |
| Blowing with nitrogen for 5 minutes, at 50° C. | 60 | 87 | 10 |
| Blowing with nitrogen for 5 minutes, at 100° C. | 50 | 54 | 44 |
| Blowing with nitrogen for 5 minutes, with microwave | 60 | 77 | 20 |
| No nitrogen blowing, at 25° C. | 40 | 11 | 84 |

As could be seen from Table 13, the selection of different reaction conditions had a significant effect on the cyclization reaction, and the reaction speed, yield, and proportion of side reactions all changed significantly. Therefore, the most preferred reaction condition was blowing with nitrogen for 5 minutes, at 25° C.

Example 22 Effect of Hst1-MAD Cyclic Peptide on Wound Repair

This example utilized the propargylglycine-Hst1-MAD cyclic peptide (Click-Hst1-MAD), linear Hst1-MAD, and linear peptide Hst1 (linear histamine 1) provided in Example 13 to conduct animal experiments, and meanwhile a Control (blank) group was set to observe the effect of the Click-Hst1-MAD on the healing rates of the wound surfaces of the mice. The concentration of the linear peptide Hst1 was 10 μM, the concentration of the linear Hst1-MAD was 1 μM, and the concentration of the Click-Hst1-MAD was 1 μM.

1. Materials and Methods

This study was approved by the Medical Animal Center and Ethics Committee of the Southern Theater Command General Hospital of the Chinese People's Liberation Army.

1.1 Sources of Animals and Main Reagents and Instruments 36 healthy male special pathogen-free grade C57 BL/6 mice of 6-8 weeks old and weighing 22-28 g, were purchased from Guangdong Experimental Animal Center. Diaminobenzidine (DAB) was purchased from Wuhan Boster Biological Technology., Ltd., a rabbit anti-CD31 antibody, a mouse anti-VEGF antibody, a goat anti-rabbit secondary antibody and a goat anti-mouse secondary antibody were purchased from Servicebio, USA, and an ethylenediaminetetraacetic acid (EDTA) antigen buffer, an immunohistochemistry pen, bovine serum albumin, collagenase A, and hematoxylin were all purchased from Wuhan Servicebio Technology Co., Ltd., an inverted fluorescence microscope was purchased from Nikon Co., Ltd., Japan, a dehydrator was purchased from Wuhan Junjie Electronics Co., Ltd., and a paraffin slicing machine was purchased from SHANGHAI Leica Instrument Co., Ltd.

1.2 Animal Grouping and Handling 36 healthy male special pathogen-free grade C57 BL/6 mice (purchased from Guangdong Experimental Animal Center) of 6-8 weeks old and weighing 22-28 g. They were intraperitoneally injected with 5 ml/kg of 1% pentobarbital sodium for anesthesia. After the mice had no corneal reflex, the hair on their backs was carefully removed and disinfected with alcohol. 21 cm×1 cm full-thickness skin defect wound surfaces were prepared on the back of each mouse by using a circular skin punch. The 36 mice were divided into a Control (blank) group with 9 mice, a 10 μM linear peptide Hst1 (Histatin1) group with 9 mice, a 1 μM Hst1-MAD linear peptide group with 9 mice, and a 1 μM propargylglycine-Hst1-MAD cyclic peptide (Click-Hst1-MAD) group with 9 mice, according to a random number table method. Each wound surface was added with 0.5 ml of four drugs respectively, and administration was conducted every day until the wound surfaces of the experimental groups healed. Photographs were taken on days 0, 3, 5, and 10 after surgery, and wound tissues were sampled on days 3, 5, and 10 for subsequent pathological staining.

1.3 Observation Indicators 1.3.1 Healing Rate of Wound Surfaces

Figure 19:
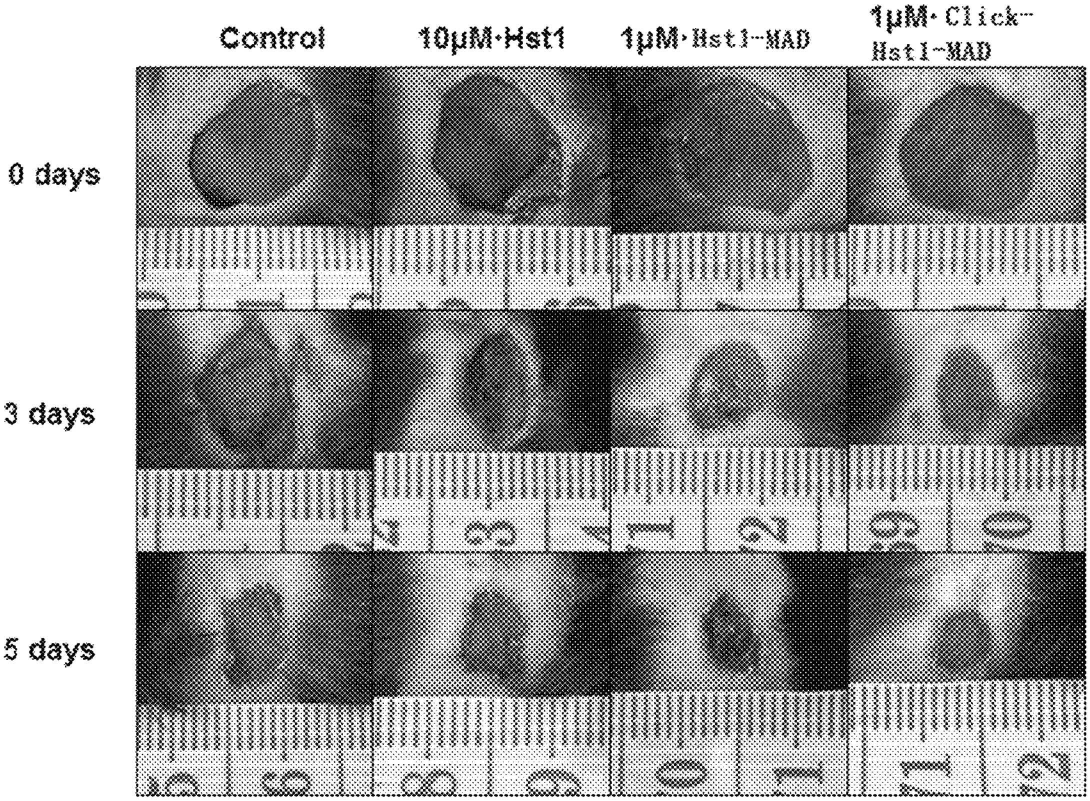
FIG. 19 is a photograph of the healing status of wound surfaces of mice in four groups of Example 22 on days 0, 3 and 5.
Figure 20:
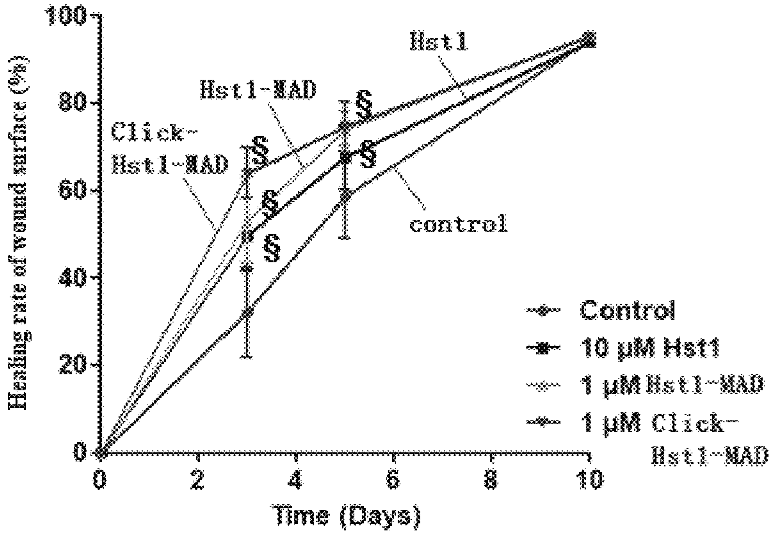
FIG. 20 is a schematic diagram comparing the healing rates of the wound surfaces of the mice in the four groups on days 3, 5, and 10 in Example 22.

On days 0, 3, 5, and 10 after injury, the general condition of wound healing of the mice was observed and photographed with a digital camera (see FIG. 19), and the wound healing rate was calculated (see FIG. 20). Wound healing rate=(wound area immediately after injury−unhealed wound area at each time point)÷wound area immediately after injury×100%.

1.3.2 Histological Morphology Detection

Figure 21:
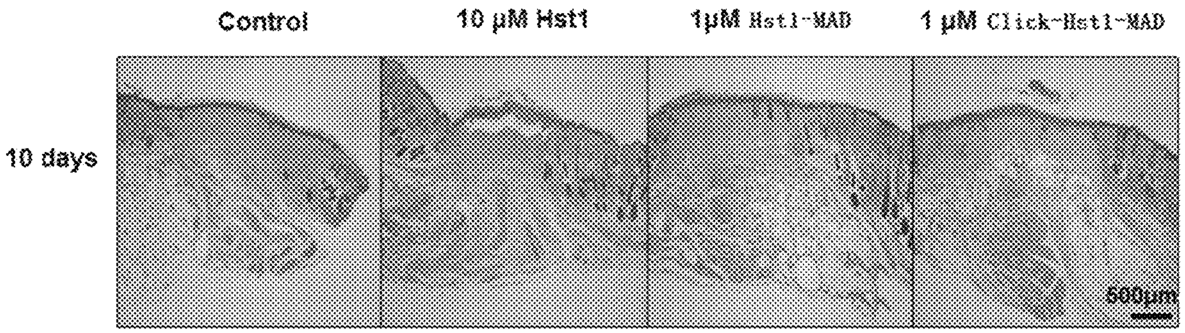
FIG. 21 is a photograph of the newly-grown wound epidermis of the four groups of wound tissues in Example 22 on day 10, as detected by HE staining.
Figure 22:
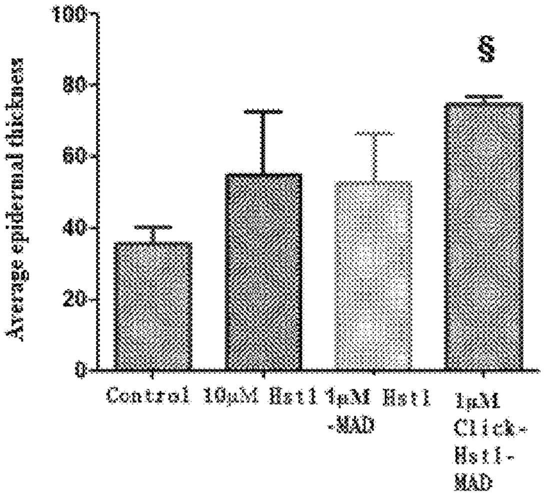
FIG. 22 is a schematic diagram comparing the newly-grown epidermal thickness of four groups of wound tissues in Example 22.

The wound specimens were fixed in 4% paraformaldehyde for 48 hours, rinsed with tap water for 10 minutes, dehydrated with graded ethanol, permeabilized with xylene, and embedded in paraffin to prepare 4 μm thick sections. Some sections were taken and subjected to HE staining to detect an epidermal thickness and subjected to Masson staining to detect newly grown collagen. Through hematoxylin-cosin staining (HE), the effects of the four groups of drugs on newly grown epidermal at the wound surface on day 10 were evaluated (FIGS. 21 and 22). Through Masson staining, the effects of the four groups of drugs on newly grown collagen at the wound surface on days 5 and 10 were evaluated (FIGS. 23 and 24). 5 sections were taken from each mouse, and 5 fields of view were selected for each section. Data analysis was performed using the software Image-pro Plus.

1.3.3 Immunohistochemistry Staining

Paraffin sections prepared in 1.3.2 on day 10 after injury were dewaxed with xylene and rehydrated, subjected to antigen thermal repair with a 0.1 mol/L citric acid buffer (with a pH value of 6.0) for 20 minutes, treated with hydrogen peroxide with a volume fraction of 10% for inactivation of endogenous peroxidase for 10 minutes, and blocked with 50 g/L of bovine serum albumin for 2 hours. It was added with a rabbit anti-mouse CD31 primary antibody (with a dilution ratio of 1:300) and a mouse anti-VEGF (with a dilution ratio of 1:100), incubated overnight at 4° C., and washed with PBS. It was rewarmed for 1 hour, washed with PBS, added dropwise with ready-to-use biotinylated goat anti-mouse and goat anti-rabbit IgG secondary antibodies, incubated for 2 hours, and washed with PBS. It was subjected to DAB development, hematoxylin counterstaining, gradient ethanol dehydration, xylene permeabilization, and resin blocking. 5 sections were taken from each mouse, and 5 fields of view were selected for each section. The sections were observed under a 400× inverted fluorescence microscope, and analyzed for the number of CD31-positive blood vessels (see FIG. 25) and VEGF expression amounts (see FIG. 26) by using Image-pro Plus software.

1.3.4 Dendritic Cells, M1 Macrophages, Claudin1 and Claudin2 Detected by Immunofluorescence Double Staining Dendritic cells (MHCII+ and CD11c+) were detected by immunofluorescence double staining: by immunofluorescence double staining, the effect of the 1 μM Hst1-MAD on the regulation of the dendritic cells (MHCII+ and CD11c+) at the wound surfaces on days 3 and 5 was evaluated.

A method for detecting the M1 macrophages (CD68+ and CD80+) and M2 (CD68+ and CD206+) macrophages by immunofluorescence double staining: by immunofluorescence double staining, the effect of the 1 μM Hst1-MAD on the regulation of the macrophages at the wound surfaces on day 5 was evaluated.

A method for detecting Claudin1 by Immunofluorescence double staining: by immunofluorescence double staining, the effect of the 1 μM Hst1-MAD on the Claudin1 at the wound surfaces on day 10 was evaluated.

A method for detecting Claudin2 by Immunofluorescence double staining: by immunofluorescence double staining, the effect of the 1 μM Hst1-MAD on the Claudin2 at the wound surfaces on day 10 was evaluated.

The specific steps were: the previous steps were the same as those of 1.3.3, and they were incubated with the antibodies MHCII (orb101661; 1:500; Biorbyt Biotechnology Co., Ltd., Wuhan, CN), CD11c (97585; 1:200; Cell Signaling Technology Inc., Boston, MA), CD68 (GB11067; 1:300; Servicebio Inc.), CD80 (GB11034; 1:300; Servicebio Inc.), CD206 (GB11062; 1:500; Servicebio Inc.), claudin1 (37-4900; 1:100; Thermo Fisher Scientific Co., Ltd, Shanghai, CN) and claudin2 (32-5600; 1:200; Thermo Fisher Scientific Co., Ltd.) at 4° C. overnight. The fluorescent-labeled secondary antibodies were incubated at room temperature for 1 h, followed by 4',6-diamidino-2'-phenylindole (DAPI) (G1012; Google Biotechnology Co., Ltd., Wuhan, CN). The stained sections were photographed by using a fluorescence microscope (Nikon Eclipse TI-SR. Tokyo, Japan). Positive cells were automatically counted and analyzed with Image-Pro Plus software. The expression levels of claudin1 and claudin2 were quantified with MOD values.

1.3.5 Western Blot

A method for detecting the Nrf2/HO-1/NQO1 signaling pathway by Western Blot: through WB experiments, the effect of the 1 μM Hst1-MAD and Click-Hst1-MAD on the antioxidative stress Nrf2/HO-1/NQO1 signaling pathway on days 3 and 5 was evaluated.

A method for detecting the expression of inflammatory factors by Western Blot: through WB experiments, the effect of the 1 μM Hst1-MAD and Click-Hst1-MAD on the regulation of the expression of inflammatory factors at the wound surfaces on days 3 and 5 was evaluated.

Specific steps: in order to detect the expression of the inflammatory factors and the regulation of oxidative stress, the wound tissue was taken for detection by Western Blot. The wound tissue was washed with PBS, added with a lysis buffer, and homogenized at 12,000 g and centrifuged for 10 min, and the supernatant was collected. A bicinchoninic acid (BCA) kit (p0010; Beyotime Biotechnology Co., Ltd., Shanghai, CN) was mixed with a reductive sodium dodecyl sulfate (SDS) sample buffer, and then boiled for 5 min. The samples were loaded onto a SDS-PAGE gel, and then electrophoresed at 80 volts for 30 min and at 120 volts for 1 h. The samples were transferred onto a polyvinylidene fluoride (PVDF) membrane, incubated with 5% skim milk powder for 1 h, and incubated with primary antibodies Nrf2 (ab137550; 1:1000; Abcam Trade Co., Ltd.), NQO1 (ab28947; 1:1000; Abcam Trade Co., Ltd.), TNF-α (ab6671; 1:1000; Abcam Trade Co., Ltd.), IL-6 (ab9324; 1:1000; Abcam Trade Co., Ltd.), macrophage inflammatory protein-1β (MIP-1β) (C04131; 1:1000; Signalway Antibody Co., Ltd, Nanjin, CN) at 4° C. overnight. Subsequently, they were incubated with an enzyme-labeled goat anti-rabbit secondary antibody (SA00001-2; 1:3000; Proteintech Group Inc., Wuhan, CN) and an HRP-labeled goat anti-mouse secondary antibody (GB23301; 1:3000; Proteintech Group Inc.) at room temperature for 1 hour, and then displayed with chemiluminescence. In order to detect the expression of the aforementioned proteins, the western blot bands were analyzed with the Image J software.

1.4 Statistical Processing

The measurement data were expressed by M±SD, and the data were analyzed by one-way analysis of variance (ANOVA) and an independent samples T-test with SPSS 20.0 software to detect whether the differences among the groups were statistically significant, and a Bonferroni test was used for pairwise comparison. *$p<0.05$. $p<0.01$. *$p<0.001$ meant the difference was statistically significant, and $p>0.05$ was not statistically significant.

2 Results 2.1 Gross Observation and Wound Healing Rate

On days 3, 5 and 10 after surgery, the wound surfaces of the four groups gradually shrank over time. The wound area of the 1 μM propargylglycine-Hst1-MAD cyclic peptide (Click-Hst1-MAD) group was smaller than those of the other three groups on days 3 and 5 (FIG. 19). As could be seen from FIG. 20, on days 3 and 5, the healing rate of the wound surface in the 1 μM Click-Hst1-MAD group was significantly higher than those of the Control group, the Histatin1 group and the Hst1-MAD linear peptide group ($P<0.05$). The wound of the mouse had basically been repaired on day 10, and thus there was no reference significance; wherein § represented there was a significant difference among the 1 μM Click-Hst1-MAD group, the 1 μM Hst1-MAD group, the 10 M Hst group and the Control group ($P<0.05$). It could be seen that the 1 μM Click-Hst1-MAD group could better promote the healing of the wound surface. Its effect was not only better than that of the 1 μM Hst1-MAD linear peptide group, but also even better than that of the 10 μM Histatin group. Meanwhile, it could also be seen that the effect of the 1 μM Hst1-MAD linear peptide group was equivalent to that of the 10 μM Histatin linear peptide group.

2.2 Histological Morphological Observation

In order to evaluate the effects of the four groups on epidermal thickness and dermal collagen expression, the wound tissue was stained with HE (FIG. 21). On day 10, the 1 μM Click-Hst1-MAD group had the thickest epidermal thickness at the wound surface, followed by the 10 μM Histatin1 group, and the Control group and the 1 μM Hst1-MAD group had the thinnest epidermal thickness ($P<0.05$) (FIG. 22).

Figure 23:
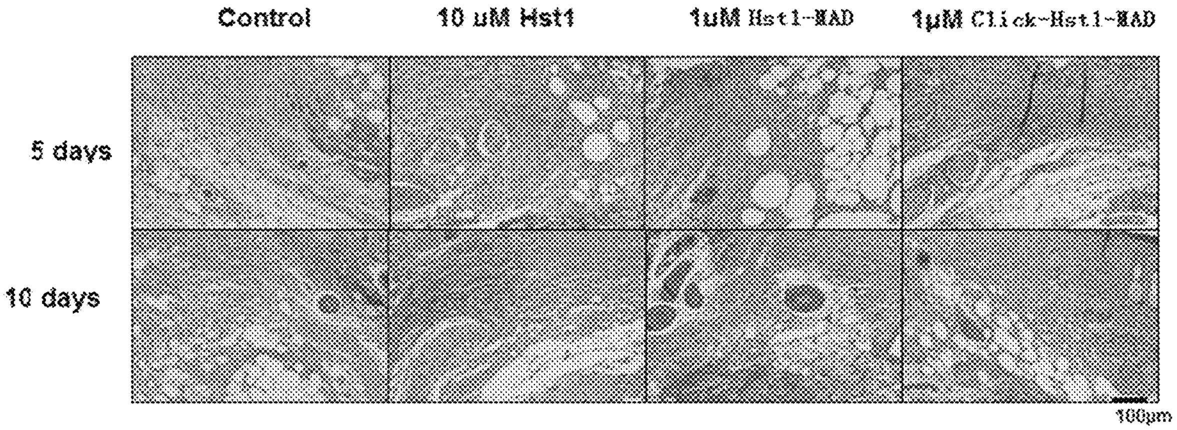
FIG. 23 is a photograph of the newly-grown collagen of the four groups of wound tissues in Example 22 on day 10, as detected by Masson staining.
Figure 24:
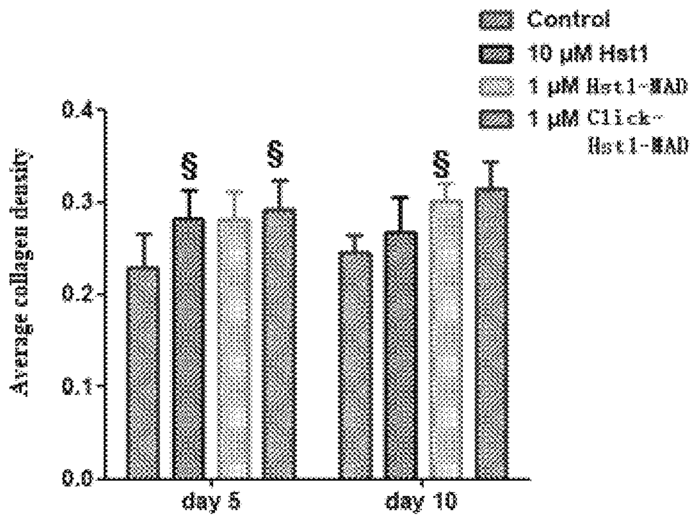
FIG. 24 is a schematic diagram comparing the newly-grown collagen of the four groups of wound tissues in Example 22 on day 10.

The results of the expression of newly grown collagen as detected by Masson staining was shown in FIG. 23. On both days 5 and 10, the expression of newly grown collagen in the 1 μM Click-Hst1-MAD group was significantly higher than those of the other three groups (FIG. 24). On day 5, the expression levels of the dermal collagen in the 1 μM Hst1-MAD group and the 10 μM Histatin1 group were equivalent. § represented that there was a significant difference among the 1 μM Click-Hst1-MAD group, the 1 μM Hst1-MAD group, the 10 μM Histatin1 group and the Control group ($P<0.05$). It showed that the 1 μM Click-Hst1-MAD group could better promote the expression of newly grown collagen.

2.3 Immunohistochemical Staining

CD31 and VEGF were angiogenesis markers. The effects of the 1 μM Click-Hst1-MAD group, the 1 μM Hst1-MAD group, the 10 μM Histatin1 group and the Control group on the angiogenesis at the wound surface were evaluated by immunohistochemical staining.

Figure 25:
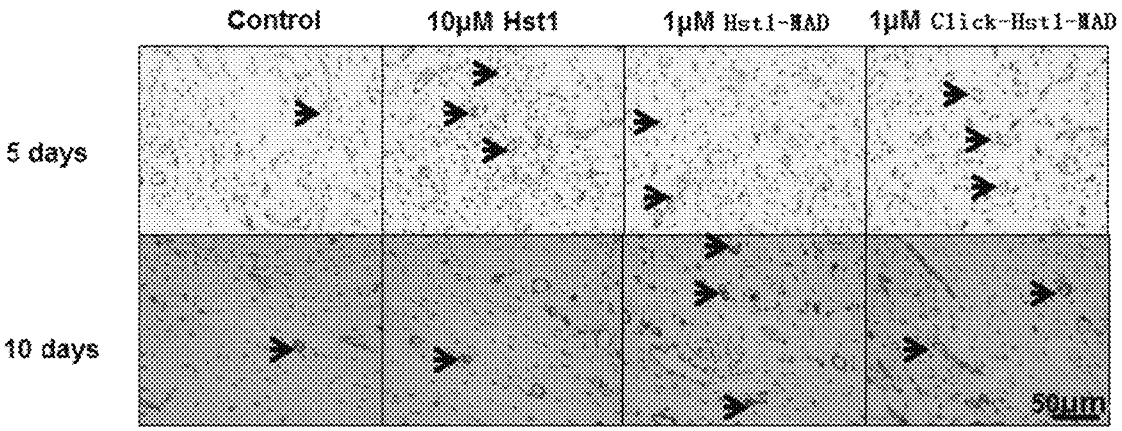
FIG. 25 is a schematic diagram of the results of the number of newly-grown CD31-positive blood vessels of wound tissues in the four groups of Example 22 on days 5 and 10.
Figure 26:
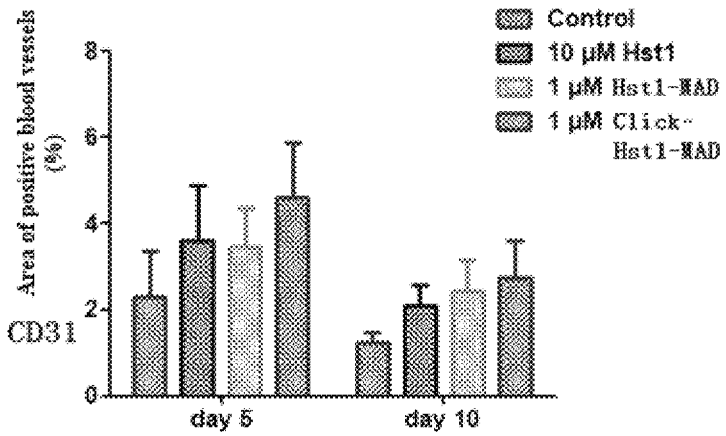
FIG. 26 is a schematic diagram comparing the quantitative analysis of the number of newly-grown CD31-positive blood vessels of the wound tissues of the four groups in Example 22 on days 5 and 10.

The results of immunohistochemical staining to evaluate the number of newly grown CD31-positive blood vessels in the 4 groups of wound surfaces were shown in FIGS. 25 and 26. As could be from FIG. 25, on days 5 and 10 after surgery, the number of CD31-positive blood vessels under each field of view in the 1 μM Click-Hst1-MAD group, the 1 μM Hst1-MAD group and the 10 μM Histatin1 group was significantly higher than that in the Control group (as indicated by the arrow). The scale bar=50 μm. As could be seen in FIG. 26, through quantitative analysis of the number of CD31-positive blood vessels, the number of newly grown blood vessels in the 1 μM Click-Hst1-MAD group was more, which was higher than those of the other three groups. § represented that there was a significant difference among the 1 μM Click-Hst1-MAD group, the 10 μM Histatin1 group, the 1 μM Hst1-MAD group and the Control group ($P<0.05$).

Figure 27:
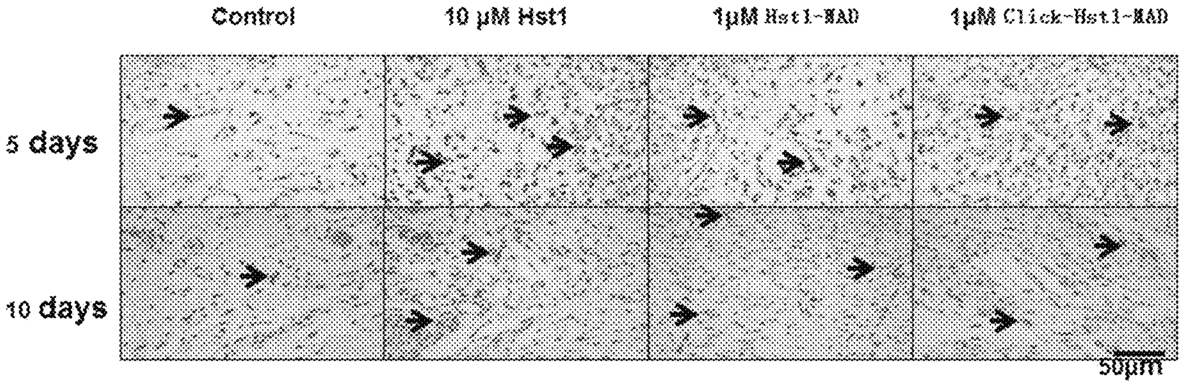
FIG. 27 is a schematic diagram of results of VEGF expression quantities of the wound tissues in the four groups of Example 22 on days 5 and 10.
Figure 28:
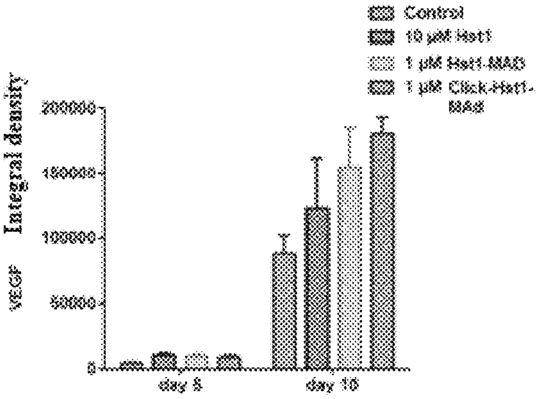
FIG. 28 is a schematic diagram comparing the quantitative analysis of VEGF expression quantities of the wound tissues in the four groups of Example 22 on days 5 and 10.
Figure 28:
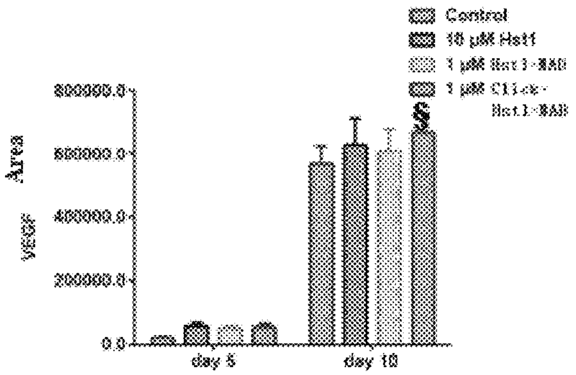

The results of immunohistochemical staining to evaluate the expression amount of VEGF at the wound surfaces of the 4 groups are shown in FIGS. 27 and 28. As could be seen from FIG. 12, on day 10 after surgery, the VEGF positive expression levels in the 1 μM Click-Hst1-MAD group and the 10 μM Histatin1 group were higher (as indicated by the arrow). The scale bar=50 μm. As could be seen from FIG. 28, (1) was the analysis result of the VEGF integrated density, and (2) was the analysis result of VEGF expression area. According to the quantitative analysis of VEGF in (1) and (2) of FIG. 13, it indicated that on day 5, the VEGF expression amounts of three groups, the 1 μM Click-Hst1-MAD group, the 10 μM Hista27tin1 group, and the 1 μM Hst1-MAD group were comparable; and on day 10, the VEGF expression amount of the 1 μM Click-Hst1-MAD group was significantly higher than those of the other three groups, § represented that there was a significant difference among the 1 μM Click-Hst1-MAD group, the 10 μM Histatin1 group, the 1 μM Hst1-MAD group and the Control group ($P<0.05$).

2.4 Immunofluorescence Double Staining

Figure 29:
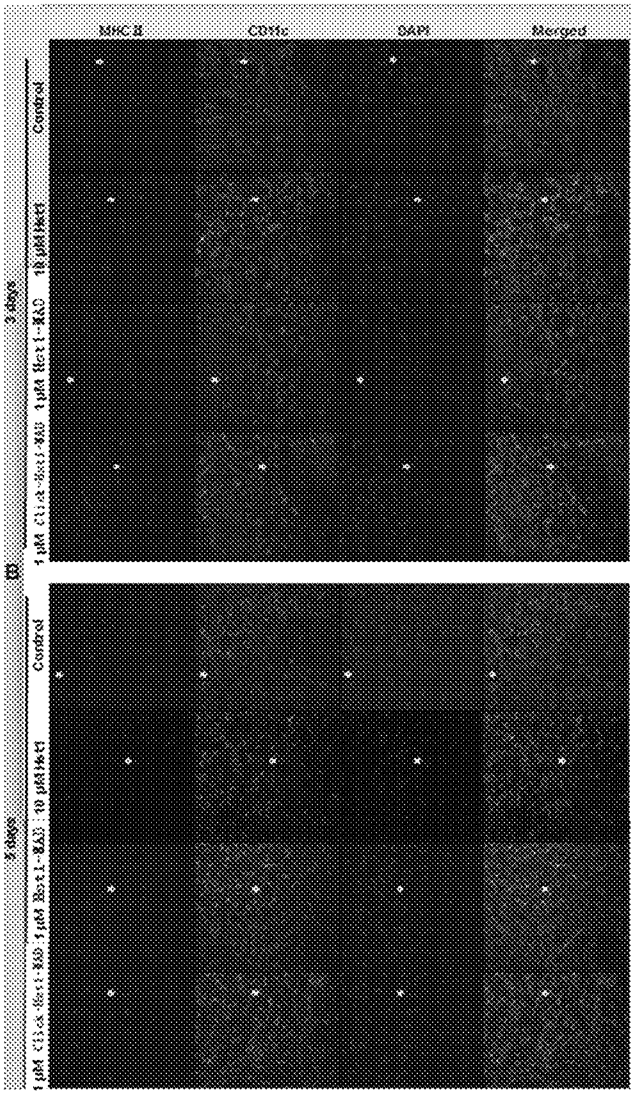
FIG. 29 is a photograph of dendritic cells (MHCII+ and CD11c+) in four groups of wound tissues in Example 22 on days 3 and 5, as detected by immunofluorescence double staining.
Figure 30:
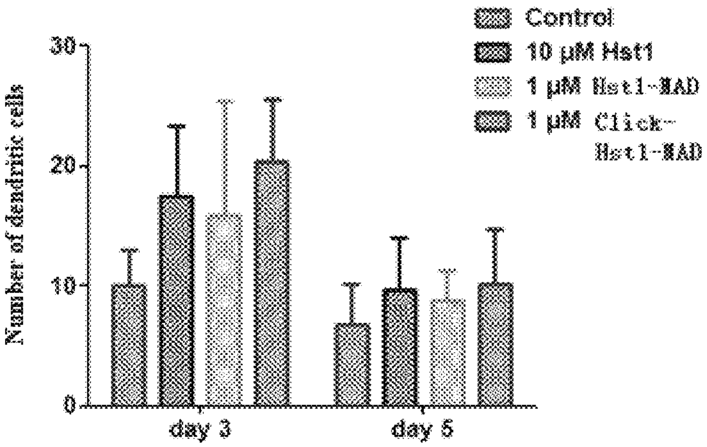
FIG. 30 is a comparison chart of analysis of the effects of the four groups of drugs in Example 22 on the regulation of wound surface dendritic cells (MHCII+ and CD11c+)

The photograph of dendritic cells (MHC II+ and CD11c+) as detected by immunofluorescence double staining was shown in FIG. 29. The analysis of the effects of the four groups of drugs on regulation of the dendritic cells (MHCII+ and CD11c+) at the wound surface was shown in FIG. 30. As could be seen from FIG. 30, the situations on days 3 and 5 were evaluated. On day 3 after surgery, the numbers of dendritic cells of the 10 μM Hst1 group and the 1 μM Click-Hst1-MAD group were 1.75 times and 1.95 times that of the control group respectively. The number of dendritic cells in the 1 μM Hst1-MAD group was slightly lower than that of the 10 μM Histatin1 group, but both of them were significantly higher than that in the Control group. The number of dendritic cells of the Click-Hst1-MAD group was significantly higher than those of the other three groups. It could be seen that the 1 μM Click-Hst1-MAD group (1 μM propargylglycine-Hst1-MAD cyclic peptide) could significantly promote the growth of the dendritic cells (MHCII+ and CD11c+) compared with the linear Hst1-MAD peptide.

Figure 31:
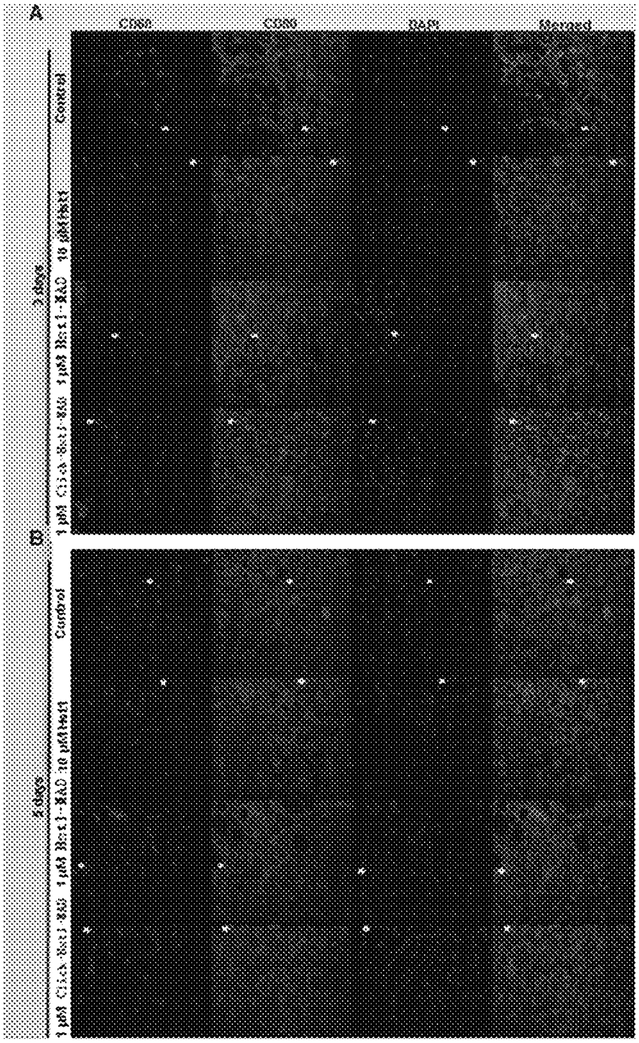
FIG. 31 is a photograph of M1 macrophages (CD68+ and CD80+) of four groups of wound tissues in Example 22 on days 3 and 5, as detected by immunofluorescence double staining.
Figure 32:
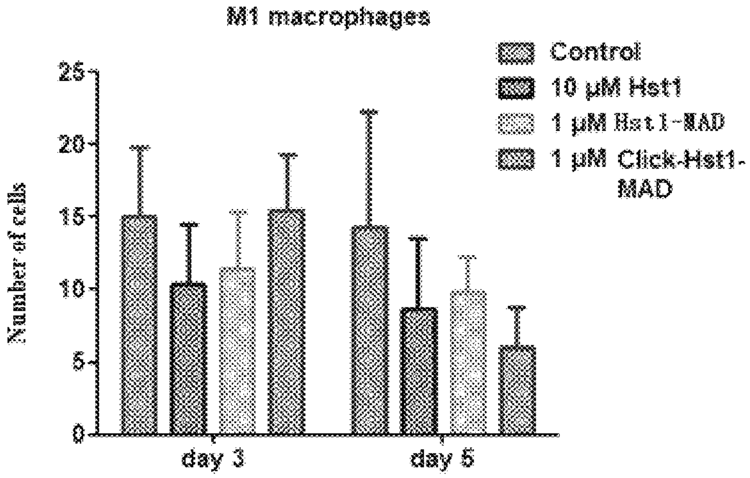
FIG. 32 is a comparison chart of analysis of the effects of the four groups of drugs on the regulation of wound surface M1 macrophages (CD68+ and CD80+) in Example 22.

The photograph of M1 macrophages (CD68+ and CD80+) as detected by immunofluorescence double staining was as shown in FIG. 31, and the analysis of the effects of the four groups of drugs on the regulation of M1 macrophages (CD68+ and CD80+) at the wound surfaces were as shown in FIG. 32. As could be seen from FIG. 32, the situations on days 3 and 5 were evaluated. The number of M1 macrophages (CD68+ and CD80+) in the 1 μM Hst1-MAD group was slightly higher than that in the 10 μM Histatin1 group, but both of them were lower than that in the Control group. It could be seen that the Hst1-MAD group and the Histatin1 group could reduce the number of M1 macrophages (CD68+ and CD80+) at the wound surface. On day 3, the number of M1 macrophages (CD68+ and CD80+) in the Click-Hst1-MAD group was equivalent to that of the Control group, and on day 5, the number of M1 macrophages (CD68+ and CD80+) in the Click-Hst1-MAD group was decreased significantly compared with those of the other three groups. It could be seen that the 1 μM propargylglycine-Hst1-MAD cyclic peptide decreased the number of the M1 macrophages (CD68+ and CD80+) after day 5 significantly, indicating that 1 μM propargylglycine-Hst1-MAD cyclic peptide could better reduce the inflammatory response in the late stage of inflammation.

Figure 33:
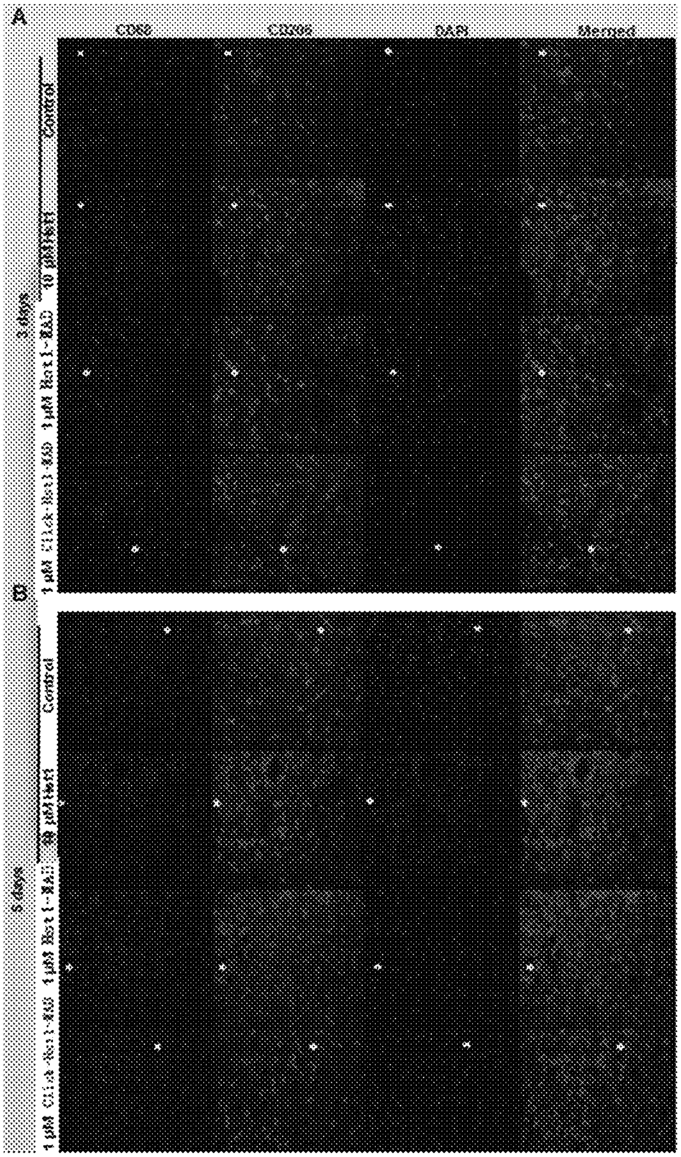
FIG. 33 is a photograph of M2 macrophages (CD68+ and CD206+) of four groups of wound tissues in Example 22 on days 3 and 5, as detected by immunofluorescence double staining.
Figure 34:
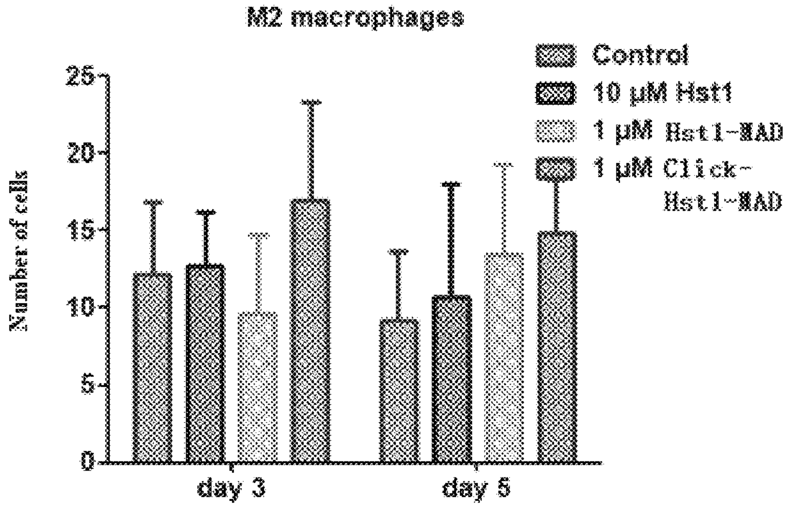
FIG. 34 is a comparison chart of analysis of the effects of the four groups of drugs on the regulation of wound surface M2 macrophages (CD68+ and CD206+) in Example 22.

The photograph of M2 macrophages (CD68+ and CD206+) as detected by immunofluorescence double staining was as shown in FIG. 33, and the analysis of the effects of the four groups of drugs on the regulation of M2 macrophages (CD68+ and CD206+) at the wound surfaces were as shown in FIG. 34. As could be seen from FIG. 34, on day 3, the number of M2 macrophages (CD68+ and CD206+) in the Click-Hst1-MAD group was significantly higher than those of the other three groups, the numbers of M2 macrophages of the 1 μM Click-Hst1-MAD group (16.40±5.86) and the 10 μM Hst1 group (12.67±7.34) were higher than that of the control group (12.17±4.44); and on day 5, the number of M2 macrophages (CD68+ and CD206+) of the Click-Hst1-MAD group was also slightly higher than those of the other three groups. The secretion of inflammatory factors by the M2 cells could promote healing of the wound surface. Therefore, it could be seen that the 1 μM propynylglycine-Hst1-MAD cyclic peptide could promote healing of the wound surface more effectively.

Figure 35:
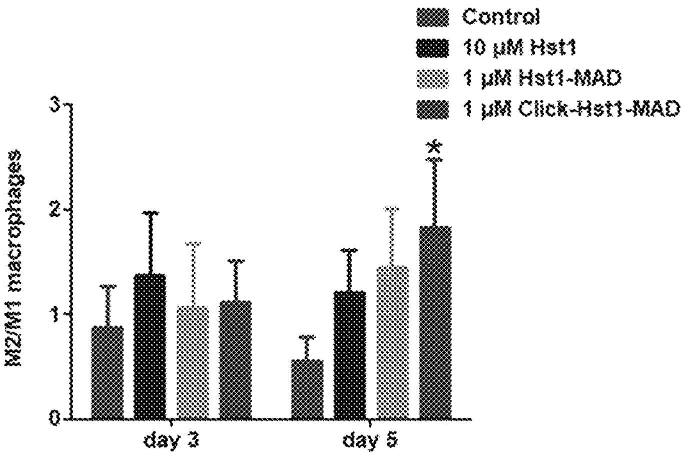
FIG. 35 is an analysis chart of M1/M2 macrophage results in Example 22.

It could be seen that the ratio of M2/M1 macrophages in the Click-Hst1-MAD group was significantly higher than those in the control group (2.61 times and 2.17 times respectively), the 10 μM Histatin1 group and the 1 μM Hst1-MAD group. This showed that the Click-Hst1-MAD group could better promote the conversion of M1 pro-inflammatory macrophages into M2 pro-healing macrophages (FIG. 35).

Figure 36:
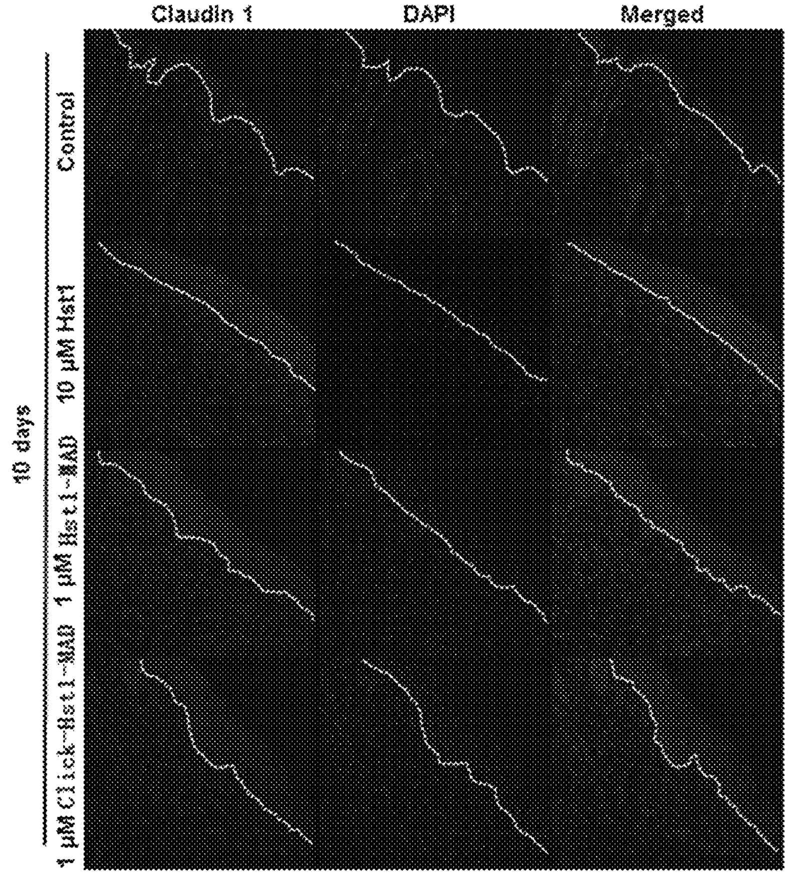
FIG. 36 is a photograph of the expression of Claudin1 of four groups of wound surfaces in Example 22, as detected by immunofluorescence double staining.
Figure 37:
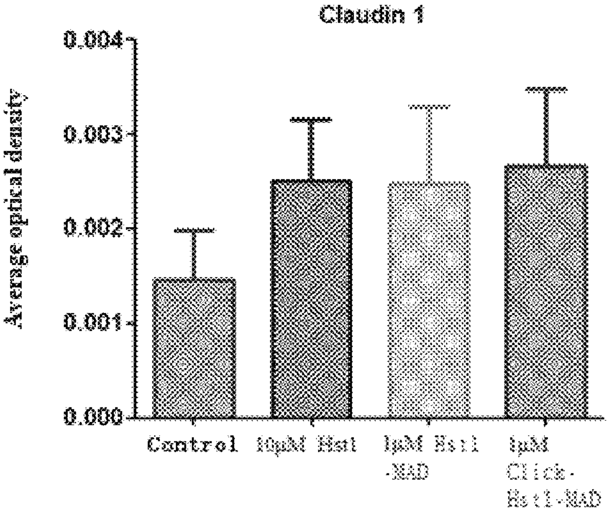
FIG. 37 is a comparative diagram of analysis of the effects of four groups of drugs on the regulation of wound surface Claudin1 in Example 22.

The photograph of the Claudin1 at the wound surface as detected by immunofluorescence double staining was shown in FIG. 36. The analysis of the effects of the four groups of drugs on the regulation of the Claudin1 at the wound surface was shown in FIG. 37. As could be seen from FIG. 37, on day 10, the Claudin1 expression intensity of the Click-Hst1-MAD group was significantly greater than those of the other three groups. The 10 μM Histatin1 group and the 1 μM Hst1-MAD group promoted an equivalent expression level of Claudin1, and the 1 μM Click-Hst1-MAD group could further effectively promote the expression of Claudin1.

Figure 38:
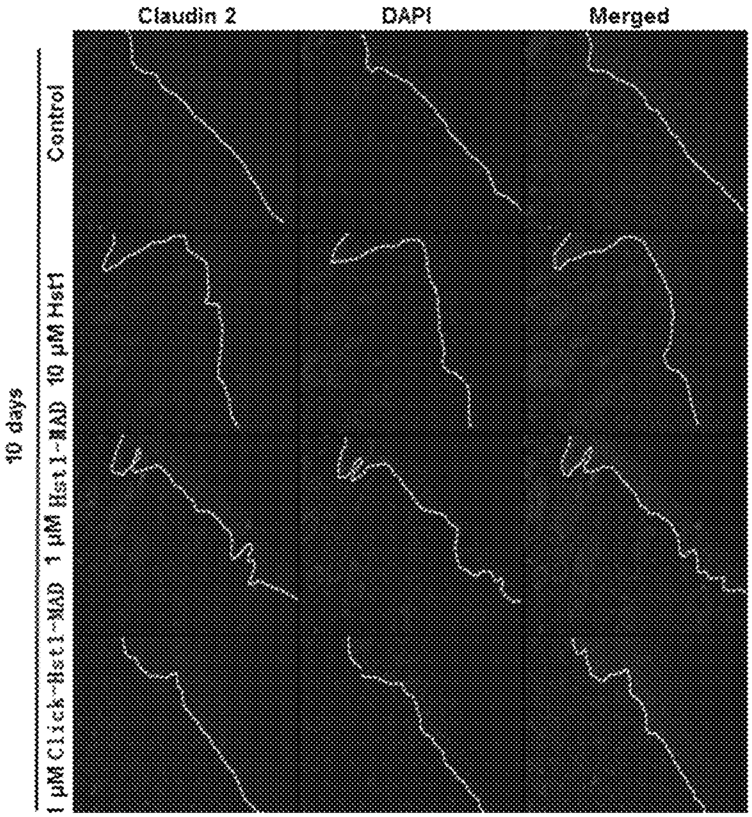
FIG. 38 is a photograph of the expression of Claudin2 of four groups of wound surfaces in Example 22, as detected by immunofluorescence double staining.
Figure 39:
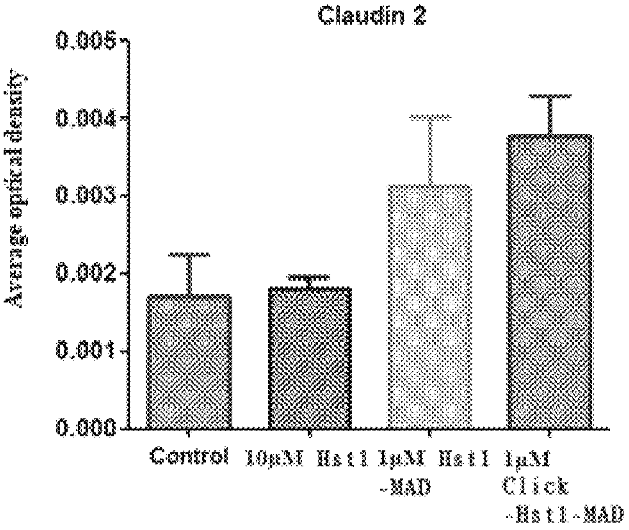
FIG. 39 is a comparative diagram of analysis of the effects of four groups of drugs on the regulation of wound surface Claudin2 in Example 22.

The photograph of the Claudin2 at the wound surface as detected by immunofluorescence double staining was shown in FIG. 38. The analysis of the effects of the four groups of drugs on the regulation of the Claudin2 at the wound surface was shown in FIG. 39. As could be seen from FIG. 39, on day 10, the Claudin2 expression intensity of the Click-Hst1-MAD group was significantly greater than those of the other three groups, followed by the 1 μM Hst1-MAD group. The 10 μM Histatin1 group had no obvious effect on promoting Claudin2 expression and was not much different from the Control group. It could be seen that compared with the 10 μM Histatin1 linear peptide, the Hst1-MAD linear peptide and the Click-Hst1-MAD cyclic peptide could promote the expression of Claudin2 more effectively, and especially the effect of the Click-Hst1-MAD cyclic peptide (1 μM propynylglycine-Hst1-MAD cyclic peptide) was particularly significant.

2.5 Western Blot

Figure 40:
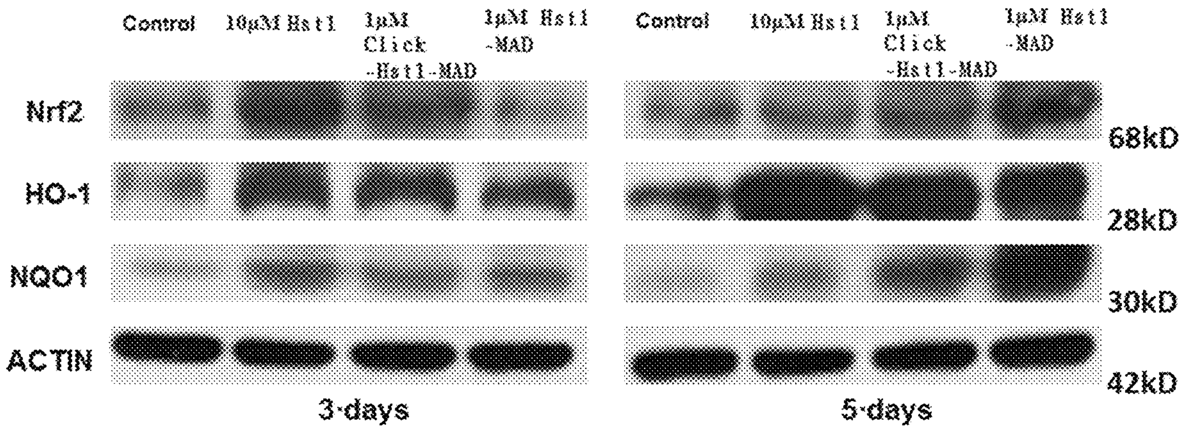
FIG. 40 is a photograph of the Nrf2/HO-1/NQO1 signaling pathway expression in four groups of wound surfaces as detected by Western Blot in Example 22.
Figure 41:
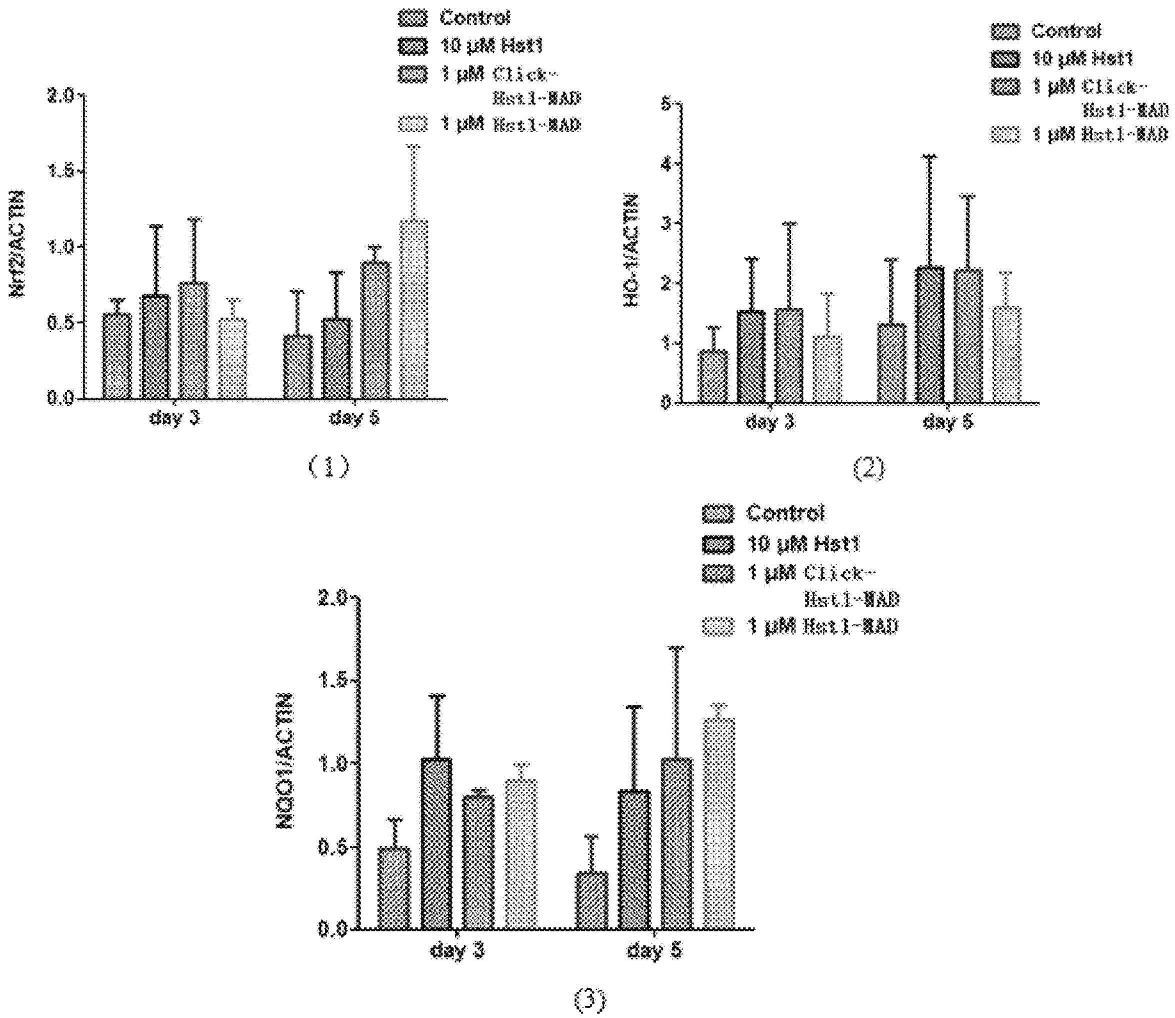
FIG. 41 is a comparison chart of analysis of the effects of the four groups of drugs on expression of the anti-oxidative stress Nrf2/HO-1/NQO1 signaling pathway of the wound surfaces in Example 22 on days 3 and 5.

The photograph of the experimental results of the Nrf2/HO-1/NQO1 signaling pathway as detected by Western Blot was shown in FIG. 40. The analysis of the effects of the four groups of drugs on the antioxidative stress Nrf2/HO-1/NQO1 signaling pathway on days 3 and 5 was shown in FIG. 41. As could be seen from FIGS. 40 and 41, on day 3 after surgery, the expression levels of Nrf2 and HO-1 in the 10 μM Histatin1 group were 1.27 and 1.80 times higher than those in the control group, respectively. The expression level of NQO1 in the 10 μM Hst1 group was significantly higher than that in the control group (2.08 times), the expression levels of Nrf2 and HO-1 in the Click-Hst1-MAD group and the Hst1-MAD group were also increased compared with those in the Control group, and were equivalent to the expression levels of the Histatin1 group; and on day 5 after surgery, the effect of the 1 μM Click-Hst1-MAD group on the expression levels of Nrf2, HO-1 and NQO1 signaling pathways was significantly higher than those in the control group and the Histatin1 group.

Figure 42:
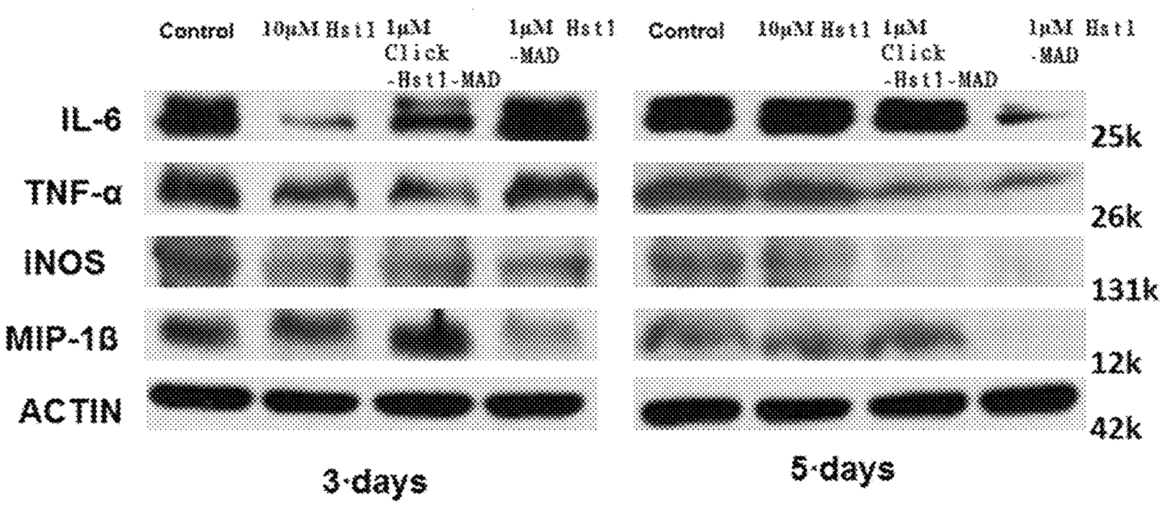
FIG. 42 is a photograph of the expression of inflammatory factors IL-6, TNF-α, iNOS and MIP-1β of four groups of wound surfaces in Example 22, as detected by Western Blot.
Figure 43:
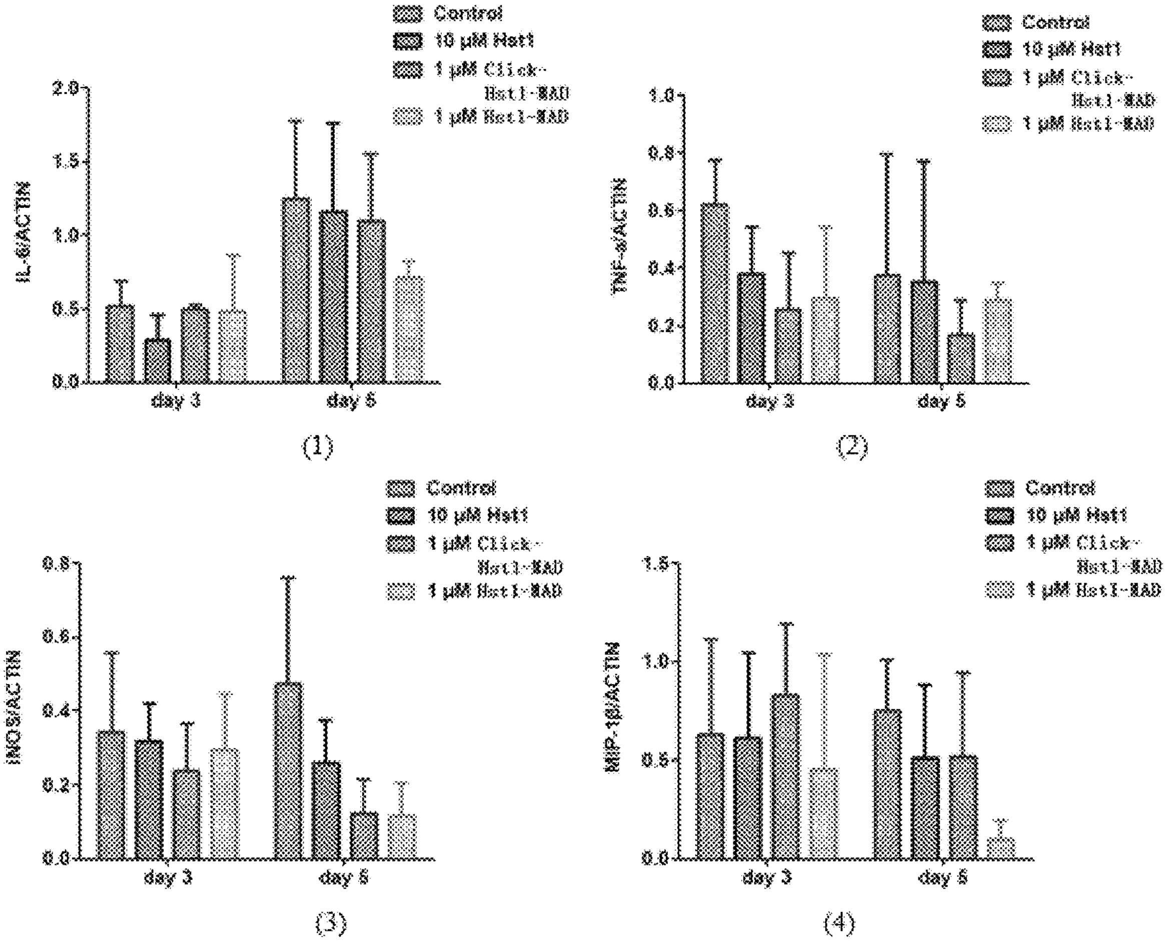
FIG. 43 is a comparison chart of analysis of the effects of the four groups of drugs on the expression of inflammatory factors IL-6, TNF-α, iNOS and MIP-1β on the wound surfaces in Example 22 on days 3 and 5.

The photograph of the experimental results of the expression levels of inflammatory factors as detected by Western Blot was shown in FIG. 42. The analysis of the effects of the four groups of drugs on the regulation of the expression of inflammatory factors at the wound surface on days 3 and 5 was shown in FIG. 43. As could be seen from FIGS. 42 and 43 that, compared with the Control group, the three groups of drugs all could effectively inhibit the expression levels of inflammatory factors IL-6, TNF-α, iNOS and MIP-1β. Among them, for the inflammatory factor TNF-α, regardless of whether on day 3 or 5 after surgery, the inhibitory effect of the 1 μM Click-Hst1-MAD group was significantly better than those of the other three groups; for the inflammatory factor iNOS, the inhibitory effect of the 1 μM Click-Hst1-MAD group was significantly better than those of the other three groups on day 3 after surgery, and on day 5 after surgery the inhibitory effect of the 1 μM Click-Hst1-MAD group was similar to that of the 1 μM Click-Hst1-MAD group, and was significantly better than those of the control group and the 10 μM Histatin1 group; and for the inflammatory factors IL-6 and MIP-1β, the inhibitory effects of the 1 μM Click-Hst1-MAD group and the 1 μM Hst1-MAD group were also significantly better than those of the control group and the 10 μM Histatin1 group.

Example 23 Activity Comparison of Cyclic Peptides

In this example, the propargylglycine-Hst1-MAD cyclic peptide, the homopropargylglycine-Hst1-MAD cyclic peptide, the dihomopropargylglycine-Hst1-MAD cyclic peptide and the linear Hst1 prepared in Examples 13, 14, and 15, and the Hst1-MAD head-to-tail cyclic peptide or N-terminal and C-terminal cyclized peptide prepared by the amide bond cyclization method provided by the literature of for example Sortase A as a tool for high-yield histatin cyclization, Jan G. M. Bolscher, The FASEB Journal. Research Communication, were adopted respectively, the reaction time was recorded, the yield of the reaction product was detected by HPLC, the proportion of side reactions in the reaction product was calculated, and activity comparison was performed. The activity comparison method was to calculate the dose required to achieve the same pharmaceutical effect through a scratch experiment. The specific method was: at the same time, fibroblasts (NIH/3T3; GNM 6; Chinese Academy of Sciences, China) were plated into a 6-well plate at a number of $2\times10^6$/well and cultured to a density of 70-80%. The cells were starved for 8-12 hours before the experiment. Mitomycin C (Sigma Aldrich, USA) was added into the culture medium to make its concentration in the culture medium be 15 μg/ml, and the culture medium was changed after 3 hours of treatment. Scratching was conducted with a 200 μl pipette tip perpendicular to the bottom of the well-plate with the same force, and the well-plate was rinsed with PBS twice after scratching. Each well was added with an appropriate amount of a DEME medium (10% FBS, 1% double antibody), and except for the blank control group, each well was added with 10 μM of the linear Hst1, 1 μM of the propargylglycine-Hst1-MAD cyclic peptide, 1 μM of the propargylglycine-Hst1-MAD cyclic peptide, 1 μM of the propargylglycine-Hst1-MAD cyclic peptide, 1 μM of the linear Hst1-MAD, and 1 μM of the Hst1-MAD head-to-tail cyclic peptide or N-terminal and C-terminal cyclized peptide prepared by the amide bond cyclization method to serve as experimental groups. Then the cells were placed at 37° C. and 5% $CO_2$ for culture. After 12 hours and 24 hours of culture, the scratched area of each group was calculated by using imageJ (Rawak Software, Inc. Germany) software, and the scratch area at 0 hour was an initial scratch area. The scratch healing rate was calculated in the following manner: W % (scratch healing rate)=(W0−Wt)/W0×100%, where W0=an initial scratch area, and Wt=a remaining scratch area; and the results were as shown in Table 14.

TABLE 14

| Activity comparison | | | | |
|---|---|---|---|---|
| Oligopeptide or polypeptide | Reaction time (min) | Yield (%) | Proportion of side reactions (%) | Dosage of agents required for scratch test (μM) |
| Propargylglycine-Hst1-MAD cyclic peptide | 40 | 94 | 3 | 0.1 |
| Homopropynylglycine-Hst1-MAD cyclic peptide | 40 | 93 | 5 | 0.9 |
| Dihomopropynylglycine-Hst1-MAD cyclic peptide | 40 | 93 | 4 | 0.7 |
| Linear Hst1 | / | / | / | 10 |
| Linear Hst1-MAD | / | / | / | 8 |
| Prepared by an amide bond cyclization method Hst1-MAD cyclic peptide | overnight | 10 | 89 | 1 |

As could be seen from Table 14 that the activity of the Hst1-MAD oligopeptide cyclic peptide prepared by the method provided by the present invention was more than 15 times higher than that of the linear peptide Hst1, and the yield was higher with very few side reactions; while the activity of the Hst1-MAD that was directly cyclized by using traditional amide bonds was lower, and even lower than that of the linear peptide Hst1-MAD, and the yield was only 10% with the proportion of side reactions up to 89%, the operation process was cumbersome, the reaction time was long, and it was difficult to prepare the Hst1-MAD cyclic peptide.

Although the present invention is disclosed above, the present invention is not limited thereto. Various changes and modifications can be made by those of skills in the art without departing from the spirit and scope of the present invention, and thus the claimed scope of the present invention should be based on the scope defined by the claims.

SEQUENCE LISTING

SEQ ID NO.1
Linear Hst1: Asp pSer His Glu Lys Arg His His Gly Tyr Arg Arg Lys Phe His Glu Lys His His Ser His Arg Glu Phe Pro Phe Tyr Gly Asp Tyr Gly Ser Asn Tyr Leu Tyr Asp Asn
SEQ ID NO.2
Linear Hst2: Arg Lys Phe His Glu Lys His His Ser His Arg Glu Phe Pro Phe Tyr Gly Asp Tyr Gly Ser Asn Tyr Leu Tyr Asp Asn
SEQ ID NO.3
Linear Hst3: Asp Ser His Ala Lys Arg His His Gly Tyr Lys Arg Lys Phe His Glu Lys His His Ser His Arg Gly Tyr Arg Ser Asn Tyr Leu Tyr Asp Asn
SEQ ID NO.4
Linear Hst4: Arg Lys Phe His Glu Lys His His Ser His Arg Gly Tyr Arg Ser Asn Tyr Leu Tyr Asp Asn
SEQ ID NO.5
Linear Hst5: Asp Ser His Ala Lys Arg His His Gly Tyr Lys Arg Lys Phe His Glu Lys His His Ser His Arg Gly Tyr
SEQ ID NO.6
Linear Hst6: Asp Ser His Ala Lys Arg His His Gly Tyr Lys Arg Lys Phe His Glu Lys His His Ser His Arg Gly Tyr Arg
SEQ ID NO.7
Linear Hst7: Arg Lys Phe His Glu Lys His His Ser His Arg Gly Tyr
SEQ ID NO.8
Linear Hst8: Lys Phe His Glu Lys His His Ser His Arg Gly Tyr
SEQ ID NO.9
Linear Hst9: Arg Lys Phe His Glu Lys His His Ser His Arg Gly Tyr Arg
SEQ ID NO.10
Linear Hst10: Lys Phe His Glu Lys His His Ser His Arg Gly Tyr Arg
SEQ ID NO.11
Linear Hst11: Lys Arg His His Gly Tyr Lys Arg
SEQ ID NO.12
Linear Hst12: Lys Arg His His Gly Tyr Lys
SEQ ID NO. 13
Hst1-MAD: SHREFPFYGDYGS

The invention claimed is:

1. A cyclic peptide, a structural formula of which is as shown in Formula 1 or Formula 2:

Formula 1

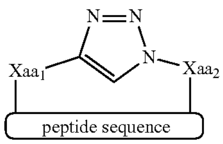

Formula 2

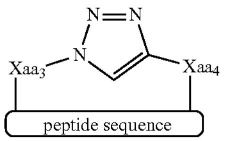

wherein $Xaa_1$, $Xaa_2$, $Xaa_3$, and $Xaa_4$ are any amino acid and the peptide sequence, fragment thereof, or derivative modified peptide thereof has at least 80% homology with any one of SEQ ID NOs: 1-13.

2. The cyclic peptide according to claim 1, wherein the derivatization modification comprises one or more of alkylation, acylation, esterification, phosphorylation, sulfonation, glycosidation, PEGylation, biotinylation, fluorescent labeling, isotope labeling, D-type, a linking linker, carrier protein coupling or a special amino acid.

3. The cyclic peptide according to claim 2, the structural formula of which is as shown in Formula 3 or Formula 4:

Formula 3

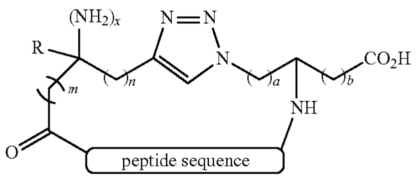

Formula 4

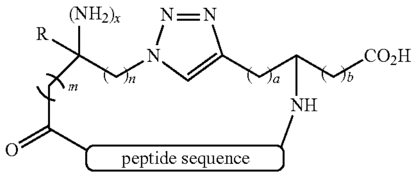

wherein, n=1-6, m=0-3, x=0 or 1, a=1-6, b=0-2, and the R group is the R group of any amino acid wherein the peptide sequence, fragment thereof, or derivative modified peptide thereof has at least 80% homology with any one of SEQ ID NOs: 1-13.

4. The cyclic peptide according to claim 3, wherein the amino group and/or carboxyl group in the Formula 3 or the Formula 4 can be derivatized.

5. The cyclic peptide according to claim 4, wherein the derivatization of the amino group in the Formula 3 or the Formula 4 comprises any one or more of acylation, alkylation, PEGylation, biotinylation or fluorescent labeling of the amino group; and the derivatization of the carboxyl group in the Formula 3 or the Formula 4 comprises any one or more of amidation, esterification, glycosidation, PEGylation of the carboxyl group.

6. The cyclic peptide according to claim 5, wherein the peptide sequence, fragment thereof, or derivative modified peptide thereof consists of SEQ ID NO: 1 or SEQ ID NO: 13.

7. The cyclic peptide according to claim 6, wherein the R group is —H.

8. The cyclic peptide according to claim 7, the structural formula of which is as shown in Formula 7, Formula 8, Formula 27 or Formula 28:

Formula 7

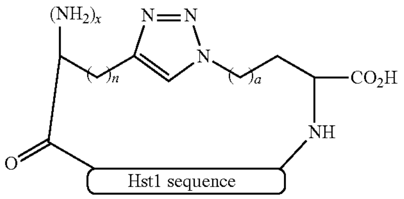

Formula 8

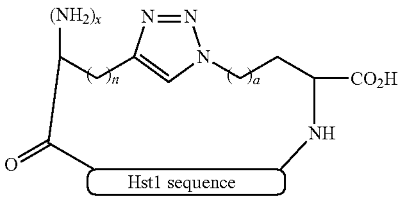

Formula 27

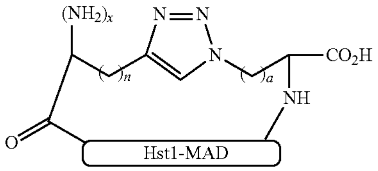

Formula 28

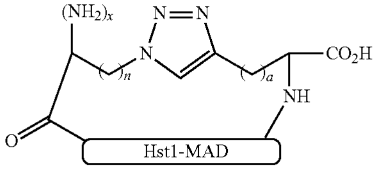

wherein, n=1-3, a=4, and x=0 or 1.

9. The cyclic peptide according to claim 1, wherein a carbon chain in which the $Xaa_1$, $Xaa_2$, $Xaa_3$, and $Xaa_4$ are connected to the triazole ring may contain any one or more of a phenyl ring, an alicyclic ring, an aromatic ring, a heterocyclic ring or halogenation.

10. A method for preparing a cyclic peptide, comprising linking any amino acid containing an alkynyl group to one terminal of a peptide sequence, linking any amino acid containing an azide group to the other terminal, and binding with a resin at any of the terminals; wherein the alkynyl group and the azido group are subjected to cycloaddition, and the resin is removed to obtain a histamine cyclic peptide; the peptide sequence, fragment thereof, or derivative modified peptide thereof has at least 80% homology with any one of SEQ ID NOs: 1-13.

11. The preparation method according to claim 10, wherein by linking a $Xaa_1$ containing an alkynyl group at the C-terminal of the peptide sequence, linking a $Xaa_2$ containing an azide group at the N-terminal, and binding with a resin on the $Xaa_2$, the alkynyl group connected to the $Xaa_1$ and the azido group connected to the $Xaa_2$ undergo cycloaddition, and the resin is removed to obtain the cyclic peptide, and the reaction formula of it is shown in Formula 9:

Formula 9

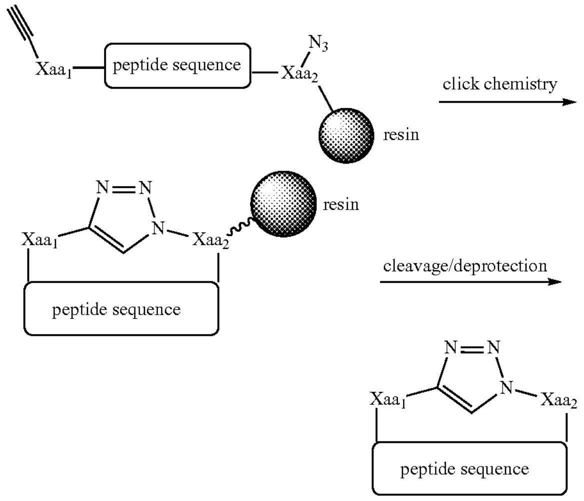

or alternatively, by linking a $Xaa_3$ containing an azide group at the C-terminal of the peptide sequence, linking a $Xaa_4$ containing an alkynyl group at the N-terminal, and binding with a resin on the $Xaa_4$, the azido group of the $Xaa_3$ and the alkynyl group of the $Xaa_4$ undergo cycloaddition, and the resin is removed to obtain the cyclic peptide, and the reaction formula of it is as shown in Formula 10:

Formula 10

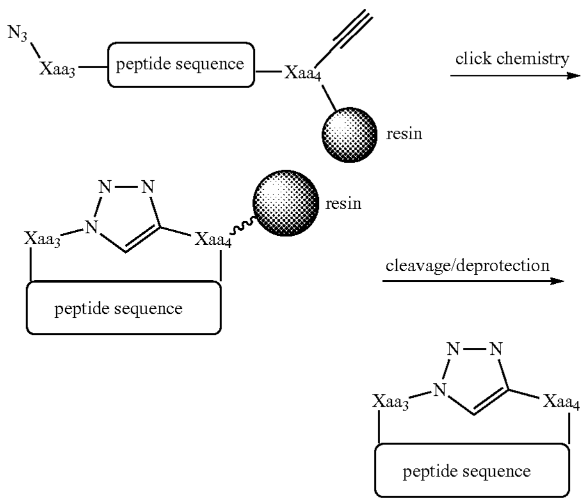

wherein, the $Xaa_1$, $Xaa_2$, $Xaa_3$, or $Xaa_4$ is any amino acid and the peptide sequence, fragment thereof, or derivative modified peptide thereof has at least 80% homology with any one of SEQ ID NOs: 1-13.

12. The preparation method according to claim 11, wherein the structural formula of the $Xaa_1$ or $Xaa_4$ containing an alkynyl group is as shown in Formula 11, or the amino and/or carboxyl modified derivative as shown in Formula 11:

Formula 11

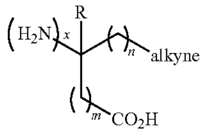

the structural formula of the $Xaa_2$ or $Xaa_3$ containing an azide group is as shown in Formula 12, or the amino and/or carboxyl modified derivative as shown in Formula 12:

Formula 12

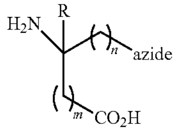

wherein, n=1-6, m=0-3, R group is the R group of any amino acid, and x=0 or 1.

13. The preparation method according to claim 12, wherein the amino group and/or carboxyl group in the Formula 11 or the Formula 12 can be derivatized.

14. The preparation method according to claim 13, wherein the peptide sequence consists of SEQ ID NO: 1 or SEQ ID NO: 13.

15. The preparation method according to claim 14, wherein the R group is —H.

16. The preparation method according to claim 15, wherein it needs to connect a protecting group Fmoc on the —$NH_2$ of the $Xaa_1$, $Xaa_2$, $Xaa_3$ or $Xaa_4$ before the reaction, and after the reaction is completed the protecting group Fmoc is removed to obtain a naked —$NH_2$, or the naked —$NH_2$ is further derived.

17. The preparation method according to claim 16, wherein it needs to connect a protecting group Fmoc on the —$NH_2$ of the $Xaa_1$ or $Xaa_3$ before the reaction, and after the reaction is completed the protecting group Fmoc is removed to obtain a naked —$NH_2$, or the naked —$NH_2$ is further derived.

18. The preparation method according to claim 17, wherein the structural formula of the $Xaa_1$ containing an alkynyl group is as shown in Formula 13:

Formula 13

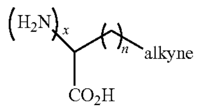

the structural formula of the $Xaa_2$ containing an azide group is as shown in Formula 14:

Formula 14

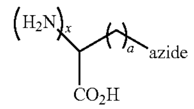

the structural formula of the $Xaa_3$ containing an azide group is as shown in Formula 15:

Formula 15

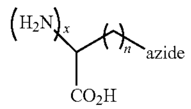

the structural formula of the $Xaa_4$ containing an alkynyl group is as shown in Formula 16:

Formula 16

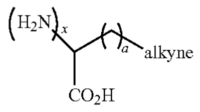

wherein, n=1-4, a=4, and x=0 or 1.

19. The preparation method according to claim 18, wherein the carbon chain of the $Xaa_1$ and/or $Xaa_4$ connected to the alkynyl group may contain any one or more of a phenyl ring, an alicyclic ring, an aromatic ring or a heterocyclic ring; and the carbon chain of the $Xaa_2$ and/or $Xaa_3$ connected to the azide group may contain any one or more of a phenyl ring, an alicyclic ring, an aromatic ring, a heterocyclic ring or halogenation.

20. The preparation method according to claim 19, comprising the following steps:

1) Placing a linear peptide prepared by a solid-phase polypeptide synthesis process into a container and adding a solvent; wherein the linear peptide comprises any one of SEQ ID NOs: 1-13 in which a $Xaa_1$ containing an alkynyl group is connected at the C-terminal, a $Xaa_2$ containing an azide group is connected at the N-terminal, and a resin is bound on the $Xaa_2$; or a linear histamine in which a $Xaa_3$ containing an azide group is connected at the C-terminal, a $Xaa_4$ containing an alkynyl group is connected at the N-terminal, and a resin is bound on the $Xaa_4$;
2) Adding a catalyst;
3) Adding a ligand;
4) Blowing with nitrogen;
5) Covering the container tightly and sealing the container, allowing the container to stand, and stirring;
6) Washing with disodium ethylene diamine tetraacetate to remove a washing liquid;
7) Washing with water, and washing with an organic solvent to remove a washing liquid;
8) Subjecting to vacuum drying;
9) Adding a mixed cleaving solution to cleave the polypeptide from the resin; and
10) purifying the polypeptide comprising any one of SEQ ID NOs: 1-13.

21. The preparation method according to claim 20, wherein the solvent in the step 1) is a mixture of acetonitrile and dimethyl sulfoxide; and the resin is Rink Amide MBHA Resin.

22. The preparation method according to claim 21, wherein the catalyst in the step 2) Is cuprous iodide; and the ligand in the step 3) is 2,6-lutidine.

23. The preparation method according to claim 22, wherein the step 4)-step 5) are a reaction process with a pH of 4-12, a reaction temperature of room temperature to 100° C., and a reaction time of 10 min to 100 h.

24. The preparation method according to claim 23, comprising the following steps:

1) placing 500 mg of a linear peptide comprising any one of SEQ ID NOs: 1-13 which was prepared by a solid-phase peptide synthesis process in a container, and adding 20 ml of a mixed solution of acetonitrile and dimethyl sulfoxide formulated in a ratio of 1:1-10:1;
2) Adding 500 mg of a resin;
3) Adding 20 mM of cuprous iodide;
4) Adding 30 μL of 2,6-lutidine;
5) Blowing with nitrogen for 2-5 minutes;
6) Covering the container tightly and sealing the container;
7) Reacting under stirring at room temperature for 40 minutes;
8) Washing twice with a saturated disodium ethylene diamine tetraacetate solution under shaking, for 10 minutes each time, to remove the washing liquid;
9) Washing once with water, once with acetonitrile, once with dichloromethane, and once with diethyl ether, to remove the washing liquid;
10) Subjecting to vacuum drying for 1 hour;
11) Cleaving: formulating a mixed cleaving solution comprising trifluoroacetic acid: phenol: thioanisole: triisopropylsilane=95.5:2:2:0.5, v/v), taking and adding 20 ml of the mixed cleaving solution into a sample obtained in the step 10), shaking for 3 hours to cleave a polypeptide from the resin, and filtering the polypeptide out with cold diethyl ether, washing for 3 times, and drying; and 12) Purifying with high-performance liquid mass spectrometry.

* * * * *